(12) United States Patent
Guo et al.

(10) Patent No.: US 12,350,303 B2
(45) Date of Patent: Jul. 8, 2025

(54) ONCOLYTIC VIRUS THERAPY

(71) Applicant: University of Pittsburgh—Of the Commonwealth System of Higher Education, Pittsburgh, PA (US)

(72) Inventors: Zong Sheng Guo, Wexford, PA (US); David Bartlett, Pittsburgh, PA (US); Zuqiang Liu, Wexford, PA (US); Mathilde Feist, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 997 days.

(21) Appl. No.: 16/482,623

(22) PCT Filed: Feb. 5, 2018

(86) PCT No.: PCT/US2018/016912
§ 371 (c)(1),
(2) Date: Jul. 31, 2019

(87) PCT Pub. No.: WO2018/145033
PCT Pub. Date: Aug. 9, 2018

(65) Prior Publication Data
US 2020/0000862 A1 Jan. 2, 2020

Related U.S. Application Data

(60) Provisional application No. 62/454,526, filed on Feb. 3, 2017.

(51) Int. Cl.
| | |
|---|---|
| A61K 38/20 | (2006.01) |
| A61K 35/761 | (2015.01) |
| A61K 35/763 | (2015.01) |
| A61K 35/768 | (2015.01) |
| A61K 38/19 | (2006.01) |
| A61K 38/21 | (2006.01) |
| C07K 14/55 | (2006.01) |
| C12N 7/01 | (2006.01) |

(52) U.S. Cl.
CPC .......... *A61K 35/763* (2013.01); *A61K 35/761* (2013.01); *A61K 35/768* (2013.01); *A61K 38/191* (2013.01); *A61K 38/2013* (2013.01); *A61K 38/217* (2013.01)

(58) Field of Classification Search
None
See application file for complete search history.

(56) References Cited

U.S. PATENT DOCUMENTS

| | | | |
|---|---|---|---|
| 6,277,368 B1 | 8/2001 | Hiserodt et al. | |
| 7,208,313 B2 | 4/2007 | McCart et al. | |
| 7,264,820 B2 | 9/2007 | Hiserodt et al. | |
| 8,506,947 B2 | 8/2013 | McCart et al. | |
| 10,086,046 B2* | 10/2018 | Paulsen | A61P 13/12 |
| 2003/0031681 A1 | 2/2003 | McCart et al. | |
| 2003/0105054 A1* | 6/2003 | Wagner | A61K 38/208 |
| | | | 514/44 R |
| 2003/0170238 A1 | 9/2003 | Gruenberg et al. | |
| 2006/0216702 A1 | 9/2006 | Compans et al. | |
| 2007/0154458 A1 | 7/2007 | McCart et al. | |
| 2010/0303714 A1 | 12/2010 | Kirn | |
| 2015/0250837 A1* | 9/2015 | Nolin | A61K 35/761 |
| | | | 435/235.1 |
| 2016/0000842 A1 | 1/2016 | Song et al. | |
| 2016/0235793 A1 | 8/2016 | Thorne | |
| 2016/0250267 A1 | 9/2016 | Uchida et al. | |
| 2017/0291934 A1 | 10/2017 | Reed et al. | |
| 2017/0340687 A1 | 11/2017 | Nakao et al. | |
| 2023/0002465 A1* | 1/2023 | Bartlett | C07K 14/5434 |

FOREIGN PATENT DOCUMENTS

| | | |
|---|---|---|
| CA | 2962099 | 3/2016 |
| CN | 101912421 | 12/2010 |
| CN | 105658795 | 6/2016 |
| CN | 110267978 | 9/2019 |
| JP | 2009-507853 | 2/2009 |
| JP | 2016-512199 | 4/2016 |
| JP | 2016-527920 | 9/2016 |
| WO | WO 1999/006544 | 2/1999 |
| WO | WO 2003/017944 | 3/2003 |
| WO | WO 2008/113078 | 9/2008 |
| WO | WO 2012/142529 | 10/2012 |
| WO | WO 2014/138314 | 9/2014 |
| WO | WO 2015/027163 | 2/2015 |
| WO | WO 2016/174200 | 3/2016 |
| WO | WO 2016/070136 | 6/2016 |
| WO | WO 2016/146894 | 9/2016 |
| WO | WO 2017/044780 | 3/2017 |
| WO | WO 2017/165464 | 9/2017 |
| WO | WO 2017/201350 | 11/2017 |
| WO | WO 2018/145033 | 8/2018 |
| WO | WO 2018/213731 | 11/2018 |
| WO | WO 2020/124274 | 6/2020 |

OTHER PUBLICATIONS

U.S. Appl. No. 17/778,463 filed May 2022, Bartlett, David.*

(Continued)

*Primary Examiner* — Thea D' Ambrosio
(74) *Attorney, Agent, or Firm* — Fish & Richardson P.C.

(57) ABSTRACT

The presently disclosed subject matter relates to tumor infiltrated T cells induced by oncolytic virus ("OV-induced T cells"), methods of making and using said OV-induced T cells for an adoptive T-cell therapy. The presently disclosed subject matter further relates to oncolytic viruses and armed oncolytic viruses, methods of making and using said oncolytic viruses, as well as pharmaceutical compositions and kits comprising said oncolytic viruses.

4 Claims, 45 Drawing Sheets

Figure 2A:
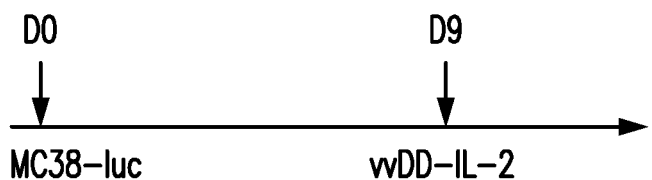

Specification includes a Sequence Listing.

(56) References Cited

OTHER PUBLICATIONS

UniProt Accession No. O75015, 9 pages (first available 1999) (Year: 1999).*
"Anchor", The Free Dictionary, available online at www.thefreedictionary.com/anchoring, 6 pages (accessed on Nov. 1, 2022) (Year: 2022).*
Arai et al., Prot. Eng. 14:529-532 (2001) (Year: 2001).*
GenBank Accession No. CAA25742.1 (2008) (Year: 2008).*
Epstein et al., J. Natl. Cancer Inst. 95:741-749 (2003) (Year: 2003).*
Medof et al., FASEB J. 10:574-586 (1996) (Year: 1996).*
NCBI Database, GenBank Accession No. AAH66254.1, 2 pages (2007) (Year: 2007).*
Kaufman et al., Nat. Rev. 14:642-662 (2015) (Year: 2015).*
EPFL, "Designing Linkers: A comprehensive guide by the EPFL 2021 iGEM team," available online at https://static.igem.org/mediawiki/2021/d/de/T--EPFL--contribution--linkers.pdf, 6 pages (2021) (Year: 2021).*
Chen et al., Adv. Drug Deliv. Rev. 65:1357-1369 (2013) (Year: 2013).*
Vagner et al., Bioconjug. Chem. 17:1545-1550 (2006) (Year: 2006).*
Alvarez-Breckenridge et al., "NK cells impede glioblastoma virotherapy through NKp30 and NKp46 natural cytotoxicity receptors," Nat Med., 2012, 18(12):1827-1834.
Andtbacka et al., "Talimogene laherparepvec improves durable response rate in patients with advanced melanoma," J clin Oncol., Sep. 2015, 33(25):2780-8.
Baluna and Vitetta, "Vascular leak syndrome: a side effect of immunotherapy," Immunopharmacology, Oct. 1997, 37(2-3):117-32.
Bartlett et al., "Oncolytic viruses as therapeutic cancer vaccines," Molecular cancer, 2013 Dec. 2013, 12(1):103.
Bourgeois-Daigneault et al., "Neoadjuvant oncolytic virotherapy before surgery sensitizes triple-negative breast cancer to immune checkpoint therapy," Science Translational Medicine, Jan. 2018, 10(422):eaao1641.
Boyman and Sprent, "The role of interleukin-2 during homeostasis and activation of the immune system," Nature Reviews Immunology, Mar. 2012, 12(3):180-90.
Boyman et al., "Potential use of IL-2/anti-IL-2 antibody immune complexes for the treatment of cancer and autoimmune disease," Expert opinion on biological therapy, Dec. 2006, 6(12):1323-31.
Boyman et al., "Selective stimulation of T cell subsets with antibody-cytokine immune complexes," Science, Mar. 2006, 311(5769):1924-7.
Brandacher et al., "Prognostic value of indoleamine 2, 3-dioxygenase expression in colorectal cancer: effect on tumor-infiltrating T cells," Clinical cancer research, Feb. 2006, 12(4):1144-51.
Chatterjee et al., "The intricate role of CXCR4 in cancer," InAdvances in cancer research, Academic Press, Jan. 2014, 124:31-82.
Chiocca and Rabkin, "Oncolytic viruses and their application to cancer immunotherapy," [published correction appears in Cancer Immunol Res. Jul. 2014;2(7):699], Cancer Immunol Res., 2014, 2(4):295-300.
Dennis et al., Current status of IL-10 and regulatory T-cells in cancer, Current opinion in oncology, Nov. 2013, 25(6):637.
Downs-Canner et al., "Phase 1 study of intravenous oncolytic poxvirus (vvDD) in patients with advanced solid cancers," Molecular Therapy, Aug. 2016, 24(8):1492-501.
Feig et al., "Targeting CXCL12 from FAP-expressing carcinoma-associated fibroblasts synergizes with anti-PD-L1 immunotherapy in pancreatic cancer," Proceedings of the National Academy of Sciences, 2013, 110(50):20212-20217.
Ferguson et al., "Chapter 11: Glycosylphosphatidyl Anchors" in Glycobiology, 2nd Edition, Varki et al., editors, Cold Spring Harbor Press, 2009 Varki A, Cummings RD, Esko JD, Freeze HH, Stanley P, Bertozzi CR, Hart GW, Etzler ME. Nematoda—Essentials of Glycobiology. Cold Spring Harbor Laboratory Press; 2009.

Fridman et al., "The immune contexture in human tumours: impact on clinical outcome," Nature Reviews Cancer, Apr. 2012, 12(4):298-306.
Fukunaga et al., "CD8+ tumor-infiltrating lymphocytes together with CD4+ tumor-infiltrating lymphocytes and dendritic cells improve the prognosis of patients with pancreatic adenocarcinoma," Pancreas, Jan. 2004, 28(1):e26-31.
Galian et al., "Efficient glycosylphosphatidylinositol (GPI) modification of membrane proteins requires a C-terminal anchoring signal of marginal hydrophobicity," Journal of Biological Chemistry, May 2012, 287(20):16399-409.
Galon et al., "Type, density, and location of immune cells within human colorectal tumors predict clinical outcome," Science, Sep. 2006, 313(5795):1960-4.
Gao et al., "Intratumoral balance of regulatory and cytotoxic T cells is associated with prognosis of hepatocellular carcinoma after resection," Journal of clinical oncology, Jun. 2007, 25(18):2586-93.
Gao et al., "Overexpression of PD-L1 significantly associates with tumor aggressiveness and postoperative recurrence in human hepatocellular carcinoma, " Clin. Cancer Res., 2009, 15(3):971-979.
GenBank Accession No. CAA25742.1, "human interleukin 2 [*Homo sapiens*]," dated Oct. 7, 2008, 2 pages.
GenBank Accession No. NM_000594.3, "*Homo sapiens* tumor necrosis factor (TNF), mRNA," dated Jul. 29, 2018, 4 pages.
Guo et al., "Oncolytic immunotherapy: conceptual evolution, current strategies, and future perspectives," Frontiers in immunology, May 2017, 8:555.
Guo et al., "Oncolytic immunotherapy: dying the right way is a key to eliciting potent antitumor immunity," Frontiers in oncology, Apr. 2014, 4:74.
Guo et al., "Oncolytic virotherapy: molecular targets in tumor-selective replication and carrier cell-mediated delivery of oncolytic viruses," Biochim Biophys Acta., 2008, 1785(2):217-231.
Guo et al., "The enhanced tumor selectivity of an oncolytic vaccinia lacking the host range and antiapoptosis genes SPI-1 and SPI-2," Cancer Res., 2005 65(21):9991-9998.
Heo et al., "Randomized dose-finding clinical trial of oncolytic immunotherapeutic vaccinia JX-594 in liver cancer," Nat Med., 2013, 19(3):329-336.
Hu et al., "Generation of low-toxicity interleukin-2 fusion proteins devoid of vasopermeability activity," Blood, Jun. 2003, 101(12):4853-61.
International Preliminary Report on Patentability International Application No. PCT/US2018/016912 dated Aug. 6, 2019, 8 pages.
International Search Report in International Application No. PCT/US2018/016912 dated May 10, 2018, 4 pages.
Ji et al., "Glycoinositol Phospholipid-anchored Interleukin 2 but not Secreted Interleukin 2 Inhibits Melanoma Tumor Growth in Mice 1 Supported by the Oncology Research Endowment of the Greenville Hospital System," Molecular cancer therapeutics, Oct. 2002, 1(12):1019-24.
Katre et al., "Chemical modification of recombinant interleukin 2 by polyethylene glycol increases its potency in the murine Meth A sarcoma model," Proceedings of the national academy of sciences, Mar. 1987, 84(6):1487-91.
Kaufman et al., "Oncolytic viruses: a new class of immunotherapy drugs," Nature reviews Drug discovery, Sep. 2015, 14(9):642-62.
Kirn et al., "Enhancing poxvirus oncolytic effects through increased spread and immune evasion," Cancer research, Apr. 2008, 68(7):2071-5.
Kobayashi et al., "T1365 FOXP3+ Regulatory T Cells and Tumoral Indoleamine 2, 3-Dioxygenase Expression Predicts the Carcinogenesis of the Pancreas," Gastroenterology, May 2010, 138(5):S-546.
Kottke et al., "Subversion of NK-cell and TNFα immune surveillance drives tumor recurrence," Cancer immunology research, Nov. 2017, 5(11):1029-45.
Lazear et al., "Targeting of IL-2 to cytotoxic lymphocytes as an improved method of cytokine-driven immunotherapy," Oncoimmunology, Feb. 2017, 6(2):e1265721.
Lee et al., "Prognostic implications of type and density of tumour-infiltrating lymphocytes in gastric cancer," Br. J. Cancer, 2008, 99(10):1704-1711.

(56) References Cited

OTHER PUBLICATIONS

Lentsch et al., "Interleukin-10 inhibits interleukin-2-induced tumor necrosis factor production but does not reduce toxicity in C3H/HeN mice," Journal of leukocyte biology, Jul. 1996, 60(1):51-7.
Létourneau et al., "IL-2/anti-IL-2 antibody complexes show strong biological activity by avoiding interaction with IL-2 receptor a subunit CD25," Proceedings of the National Academy of Sciences, Feb. 2010, 107(5):2171-6.
Levin et al., "Exploiting a natural conformational switch to engineer an interleukin-2 'superkine'," Nature, Apr. 2012, 484(7395):529-33.
Li et al., "Chemokine expression from oncolytic vaccinia virus enhances vaccine therapies of cancer," Molecular Therapy, Apr. 2011, 19(4):650-7.
Liao et al., "Interleukin-2 at the crossroads of effector responses, tolerance, and immunotherapy," Immunity, Jan. 2013, 38(1):13-25.
Liu et al., "CXCL11-Armed oncolytic poxvirus elicits potent antitumor immunity and shows enhanced therapeutic efficacy," Oncoimmunology, Mar. 2016, 5(3):e1091554.
Liu et al., "Isolation of mouse tumor-infiltrating leukocytes by Percoll gradient centrifugation," Bio-Protocol., 2013, 3(17).
Liu et al., "Rational combination of oncolytic vaccinia virus and PD-L1 blockade works synergistically to enhance therapeutic efficacy," Nature communications, Mar. 2017, 8(1):1-2.
Lotze et al., "In vivo administration of purified human interleukin 2. II. Half life, immunologic effects, and expansion of peripheral lymphoid cells in vivo with recombinant IL 2," J. Immunol., Oct. 1985, 135(4):2865-2875.
Martínez-Bosch et al., "Galectin-1 drives pancreatic carcinogenesis through stroma remodeling and Hedgehog signaling activation," Cancer Res, 2014, 74(13):3512-3524.
Matzinger, "The danger model: a renewed sense of self," Science, Apr. 2002, 296(5566):301-5.
Mayor and Riezman, "Sorting GPI-anchored proteins," Nature reviews Molecular cell biology, Feb. 2004, 5(2):110-20.
McCart et al., "Systemic cancer therapy with a tumor-selective vaccinia virus mutant lacking thymidine kinase and vaccinia growth factor genes," Cancer research, Dec. 2001, 61(24):8751-7.
Medzhitov and Janeway, "Decoding the patterns of self and nonself by the innate immune system," Science, Apr. 2002, 296(5566):298-300.
Melder et al., "Pharmacokinetics and in vitro and in vivo anti-tumor response of an interleukin-2-human serum albumin fusion protein in mice," Cancer immunology, immunotherapy, Jun. 2005, 54(6):535-47.
Nakakubo et al., "Clinical significance of immune cell infiltration within gallbladder cancer," British journal of cancer, Nov. 2003, 89(9):1736-42.
Pagès et al., "Effector memory T cells, early metastasis, and survival in colorectal cancer," New England journal of medicine, Dec. 2005, 353(25):2654-66.
Pan et al., "Cancer immunotherapy using a membrane-bound interleukin-12 with B7-1 transmembrane and cytoplasmic domains," Molecular Therapy, May 2012, 20(5):927-37.
Paulick and Bertozzi, "The glycosylphosphatidylinositol anchor: a complex membrane-anchoring structure for proteins," Biochemistry, Jul. 2008, 47(27):6991-7000.
Puskas et al., "Development of an Attenuated interleukin-2 Fusion Protein That Can Be Activated by Tumour-Expressed Proteases," Immunology, Jun. 2011, 133(2):206-20.
Qin et al., "Gene therapy for head and neck cancer using vaccinia virus expressing IL-2 in a murine model, with evidence of immune suppression, " Molecular Therapy, Dec. 2001, 4(6):551-8.
Quandt et al., "B7-h4 expression in human melanoma: its association with patients' survival and antitumor immune response," Clinical cancer research, May 2011, 17(10):3100-11.
Ribas et al., "Oncolytic virotherapy promotes intratumoral T cell infiltration and improves anti-PD-1 immunotherapy," Cell, Sep. 2017, 170(6):1109-19.
Rintoul et al., "A selectable and excisable marker system for the rapid creation of recombinant poxviruses, " PloS one, 2011, 6(9).
Rosenstein et al., "Extravasation of intravascular fluid mediated by the systemic administration of recombinant interleukin 2," The Journal of Immunology, Sep. 1986, 137(5):1735-42.
Russell et al., "Oncolytic virotherapy," Nature biotechnology, Jul. 2012, 30(7):658.
Saha et al., "Macrophage Polarization Contributes to Glioblastoma Eradication by Combination Immunovirotherapy and Immune Checkpoint Blockade," Cancer Cell, Aug. 2017, 32(2):253-67.
Samson et al., "Intravenous delivery of oncolytic reovirus to brain tumor patients immunologically primes for subsequent checkpoint blockade," Science translational medicine, Jan. 2018, 10(422):eaam 7577.
Sathaiah et al., "Oncolytic poxvirus armed with Fas ligand leads to induction of cellular Fas receptor and selective viral replication in FasR-negative cancer," Cancer gene therapy, Mar. 2012, 19(3):192-201.
Siegal et al., "Cancer statistics," Ca. cancer J. Clin., Jan. 2014, 64(1):9-29.
Simmons and Seed, "The Fcγ receptor of natural killer cells is a phospholipid-linked membrane protein," Nature, Jun. 1988, 333(6173):568-70.
Takagi et al., "Dendritic cells, T-cell infiltration, and Grp94 expression in cholangiocellular carcinoma," Human pathology, Jul. 2004, 35(7):881-6.
Tang et al., "PAMP s and DAMP s: signal Os that spur autophagy and immunity," Immunological reviews, Sep. 2012, 249(1):158-75.
Thorne et al., "Rational strain selection and engineering creates a broad-spectrum, systemically effective oncolytic poxvirus, JX-963," The Journal of clinical investigation, Nov. 2007, 117(11):3350-8.
Vazquez-Lombardi et al., "Potent antitumour activity of interleukin-2-Fc fusion proteins requires Fc-mediated depletion of regulatory T-cells," Nature communications, May 2017, 8(1):1-2.
Written Opinion in International Application No. PCT/US2018/016912 dated May 10, 2018, 7 pages.
Yang et al., "Randomized study of high-dose and low-dose inter leukin-2 in patients with metastatic renal cancer," Journal of clinical oncology: official journal of the American Society of Clinical Oncology, Aug. 2003, 21(16):3127.
Zeh et al., "First-in-man study of western reserve strain oncolytic vaccinia virus: safety, systemic spread, and antitumor activity," Molecular Therapy, Jan. 2015, 23(1):202-14.
Zhang et al., "Eradication of solid human breast tumors in nude mice with an intravenously injected light-emitting oncolytic vaccinia virus," Cancer research, Oct. 2007, 67(20):10038-46.
Zou, "Immunosuppressive networks in the tumour environment and their therapeutic relevance," Nature reviews cancer, Apr. 2005, 5(4):263-74.
Feist et al., "Oncolytic virus promotes tumor-reactive infiltrating lymphocytes for adoptive cell therapy," Cancer Gene Therapy, Jul. 7, 2020, 14 pages.
Keller et al., "Oncolytic viruses-immunotherapeutics on the rise," Journal of Molecular Medicine, Aug. 4, 2016, 94(9):979-991.
Nguyen et al., "Expansion and Characterization of Human Melanoma Tumor-Infiltrating Lymphocytes (TILs)," PLOS One, Nov. 2010, 5(11):e13940, 12 pages.
Poutou et al., "Safety and antitumor effect of oncolytic and helper-dependent adenoviruses expressing interleukin-12 variants in a hamster pancreatic cancer model," Gene Therapy, May 21, 2015, 22(9):696-706.
Rosenberg et al., "Adoptive cell transfer as personalized immunotherapy for human cancer," Science, Apr. 3, 2015, 348(6230):62-68.
Ge et al., "Oncolytic vaccinia virus delivering tethered IL-12 enhances antitumor effects with improved safety," J. Immunother. Cancer, Mar. 2020, 8(1):e000710, 8 pages.
Abastado, "The next challenge in cancer immunotherapy: controlling T-cell traffic to the tumor," Cancer Research, May 2012, 72(9):2159-2161.
Abdi et al., "Free IL-12p40 Monomer Is a Polyfunctional Adaptor for Generating Novel IL-12-like Heterodimers Extracellularly," J. Immunology, Jun. 15, 2014, 192(12):6028-6036.
Atkins et al., "Phase I evaluation of intravenous recombinant human interleukin 12 in patients with advanced malignancies," Clin. Cancer Research, Mar. 1997, 3(3):409-417.

(56) References Cited

OTHER PUBLICATIONS

Berraondo et al., "Revisiting Interleukin-12 as a Cancer Immunotherapy Agent," Clin. Cancer Research, Jun. 15, 2018, 24(12):2716-2718.
Bommareddy et al., "Integrating oncolytic viruses in combination cancer immunotherapy," Nat. Rev. Immunology, Aug. 2018, 18(8):498-513.
Brahmer et al., "Safety and activity of anti-PD-L1 antibody in patients with advanced cancer," N. Engl. J. Medicine, Jun. 28, 2012, 366(26):2455-2465.
Cao et al., "Interleukin 12 stimulates IFN-gamma-mediated inhibition of tumor-induced regulatory T-cell proliferation and enhances tumor clearance," Cancer Research, Nov. 15, 2009, 69(22):8700-8709.
Cervera-Carrascon et al., "TNFa and IL-2 armed adenoviruses enable complete responses by anti-PD-1 checkpoint blockade," Oncoimmunology, Apr. 9, 2018, 7(5):e1412902, 12 pages.
Chen et al., "Elements of cancer immunity and the cancer-immune set point," Nature, Jan. 18, 2017, 541:321-330.
Chen et al., "Oncology meets immunology: the cancer-immunity cycle," Immunity, Jul. 25, 2013, 39(1):1-10.
Chon et al., "Tumor Microenvironment Remodeling by Intratumoral Oncolytic Vaccinia Virus Enhances the Efficacy of Immune-Checkpoint Blockade," Clin. Cancer Research, Mar. 1, 2019, 25(5):1612-1623.
Cohen, "IL-12 deaths: explanation and a puzzle," Science, Nov. 10, 1995, 270(5238):908.
Colombo et al., "Interleukin-12 in anti-tumor immunity and immunotherapy," Cytokine Growth Factor Reviews, Apr. 2002, 13(2):155-168.
Efremova et al., "Targeting immune checkpoints potentiates immunoediting and changes the dynamics of tumor evolution," Nat. Communications, Jan. 2, 2018, 9(1):32, 13 pages.
Essentials of Glycobiology, 2nd ed., Varki et al. (eds.), 2009, Chapter 11, 27 pages.
Extended European Search Report in European Appln. No. 20889840.3, dated Sep. 8, 2023, 12 pages.
Fortin et al., "NK cell response to vaccinia virus is regulated by myeloid-derived suppressor cells," J. Immunology, Aug. 15, 2012, 189(4):1843-1849.
Gajewski, "The Next Hurdle in Cancer Immunotherapy: Overcoming the Non-T-Cell-Inflamed Tumor Microenvironment," Semin. Oncology, Aug. 2015, 42(4):663-671.
GenBank Accession No. BC128562.1, "*Homo sapiens* Fc fragment of IgG, low affinity IIIb, receptor (CD16b), mRNA (cDNA clone MGC:157032 IMAGE:40126686), complete cds," dated Dec. 5, 2006, 2 pages.
Guo et al., "Vaccinia virus-mediated cancer immunotherapy: cancer vaccines and oncolytics," J. Immunother. Cancer, Jan. 9, 2019, 7(1):6, 21 pages.
Hodi et al., "Improved survival with ipilimumab in patients with metastatic melanoma," N. Engl. J. Medicine, Aug. 19, 2010, 363(8):711-723.
Kowalsky et al., "Superagonist IL-15-Armed Oncolytic Virus Elicits Potent Antitumor Immunity and Therapy That Are Enhanced with PD-1 Blockade," Mol. Therapy, Oct. 3, 2018, 26(10):2476-2486.
Leach et al., "Enhancement of antitumor immunity by CTLA-4 blockade," Science, Mar. 22, 1996, 271(5256):1734-1736.
Leonard et al., "Effects of single-dose interleukin-12 exposure on interleukin-12-associated toxicity and interferon-gamma production," Blood, Oct. 1, 1997, 90(7):2541-2548.
Liu et al., "Modifying the cancer-immune set point using vaccinia virus expressing re-designed interleukin-2," Nat. Communications, Nov. 8, 2018, 9(1):4682, 9 pages.
Mariathasan et al., "Tgfβ attenuates tumour response to PD-L1 blockade by contributing to exclusion of T cells, " Nature, Feb. 22, 2018, 554(7693):544-548.
Nagarajan et al., "Glycolipid-anchored IL-12 expressed on tumor cell surface induces antitumor immune response," Cancer Research, May 15, 2002, 62(10):2869-2874.
Naik et al., "Intravenous and isolated limb perfusion delivery of wild type and a tumor-selective replicating mutant vaccinia virus in nonhuman primates," Hum. Gene Therapy, Jan. 2006, 17(1):31-45.
PCT International Preliminary Report on Patentability in International Appln. No. PCT/US2020/061578, mailed on Jun. 2, 2022, 8 pages.
PCT International Search Report and Written Opinion in International Appln. No. PCT/US2020/061578, mailed on Mar. 22, 2021, 11 pages.
Pearl et al., "Oncolytic Virus-Based Cytokine Expression to Improve Immune Activity in Brain and Solid Tumors," Mol. Ther. Oncolytics, Mar. 20, 2019, 13:14-21.
Pelin et al., "Abstract #PR19: Utilizing novel oncolytic vaccinia virus for selective expression of immunotherapeutic payloads in metastatic tumors," Cancer Immunol. Res., Apr. 2020, 8(4_supplement):PR19.
Ribas, "Adaptive Immune Resistance: How Cancer Protects from Immune Attack," Cancer Discovery, Sep. 2015, 5(9):915-919.
Sharma et al., "Primary, Adaptive, and Acquired Resistance to Cancer Immunotherapy," Cell, Feb. 9, 2017, 168(4):707-723.
Smith et al., "PD-1 Blockade Following Isolated Limb Perfusion with Vaccinia Virus Prevents Local and Distant Relapse of Soft-tissue Sarcoma," Clin. Cancer Research, Jun. 1, 2019, 25(11):3443-3454.
Sun et al., "Regulation and Function of the PD-L1 Checkpoint," Immunity, Mar. 20, 2018, 48(3):434-452.
Topalian et al., "Safety, activity, and immune correlates of anti-PD-1 antibody in cancer," N. Engl. J. Medicine, Jun. 28, 2012, 366(26): 2443-2454.
Tugues et al., "New insights into IL-12-mediated tumor suppression," Cell Death Differentiation, Feb. 2015, 22(2):237-246.
Twumasi-Boateng et al., "Oncolytic viruses as engineering platforms for combination immunotherapy," Nat. Rev. Cancer, Jul. 2018, 18(7):419-432.
Van der Woude et al., "Migrating into the Tumor: a Roadmap for T Cells, " Trends Cancer, Nov. 2017, 3(11):797-808.
Wang et al., "Re-designing Interleukin-12 to enhance its safety and potential as an anti-tumor immunotherapeutic agent," Nat. Communications, Nov. 9, 2017, 8:1395, 15 pages.
Yadav et al., "Predicting immunogenic tumour mutations by combining mass spectrometry and exome sequencing," Nature, Nov. 26, 2014, 515:572-576.
Zamarin et al., "Intratumoral modulation of the inducible co-stimulator ICOS by recombinant oncolytic virus promotes systemic anti-tumour immunity," Nat. Communications, Feb. 13, 2017, 8:14340, 14 pages.
Zamarin et al., "Localized oncolytic virotherapy overcomes systemic tumor resistance to immune checkpoint blockade immunotherapy," Sci. Transl. Medicine, Mar. 5, 2014, 6(226):226ra232, 12 pages.
Zhang et al., "Tumor-infiltrating lymphocytes genetically engineered with an inducible gene encoding interleukin-12 for the immunotherapy of metastatic melanoma," Clin. Cancer Research, May 15, 2015, 21(10):2278-2288.
Zou et al., "PD-L1 (B7-H1) and PD-1 pathway blockade for cancer therapy: Mechanisms, response biomarkers, and combinations," Sci. Transl. Medicine, Mar. 2, 2016, 8(328):328rv324.
U.S. Appl. No. 17/778,463, filed May 20, 2022, David Bartlett.
Kobayashi et al., "FOXP3+ regulatory T cells and tumoral indoleamine 2,3-dioxygenase expression predicts the carcinogenesis of intraductal papillary mucinous neoplasms of the pancreas," Pancreatology, 2010, 10(5):631-640.
Nomi et al., "Clinical Significance and Therapeutic Potential of the Programmed Death-1 Ligand/Programmed Death-1 Pathway in Human Pancreatic Cancer," Clin. Cancer Res., Apr. 2007, 13(7):2151-2157.

\* cited by examiner

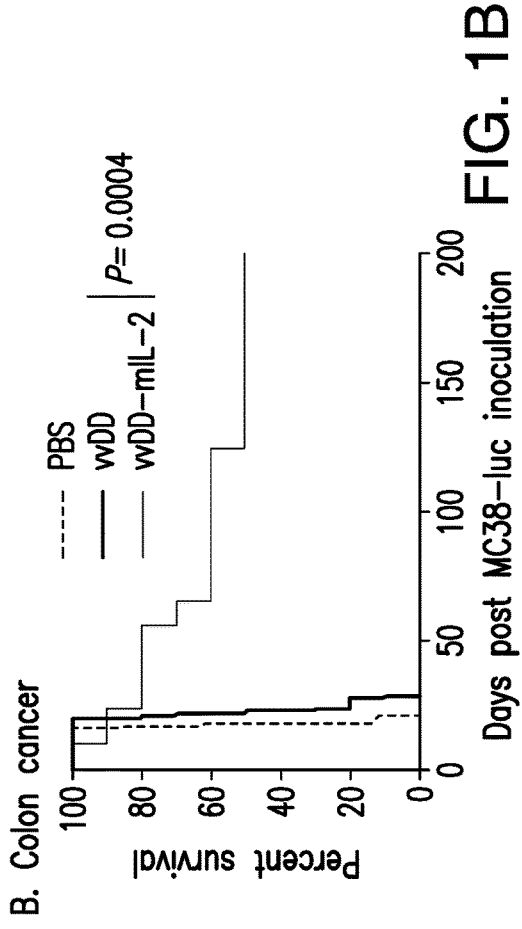
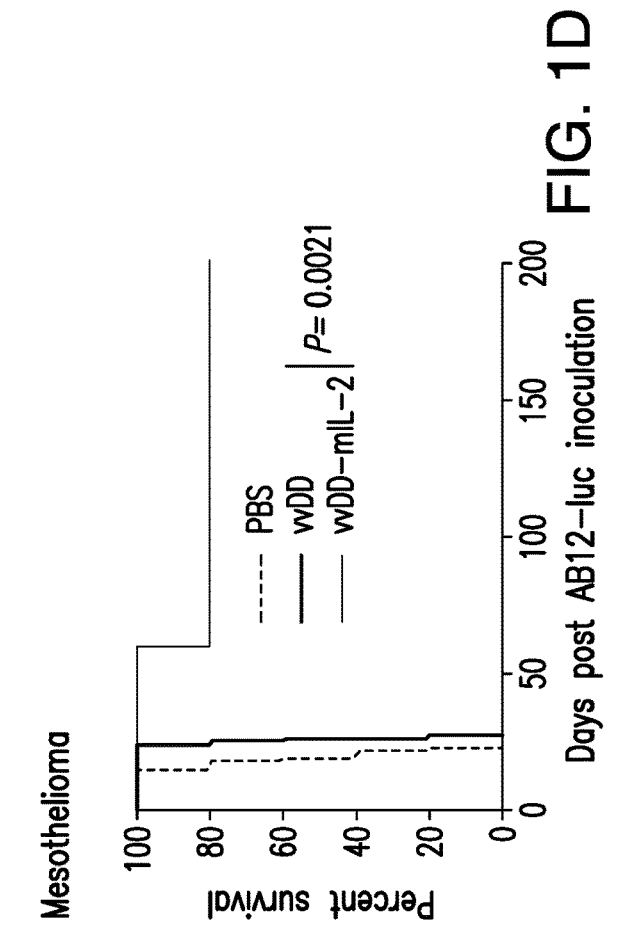
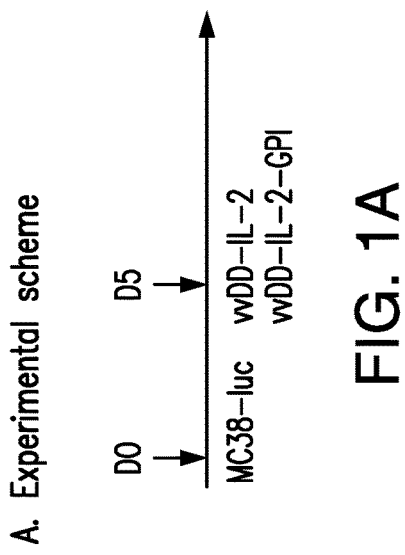
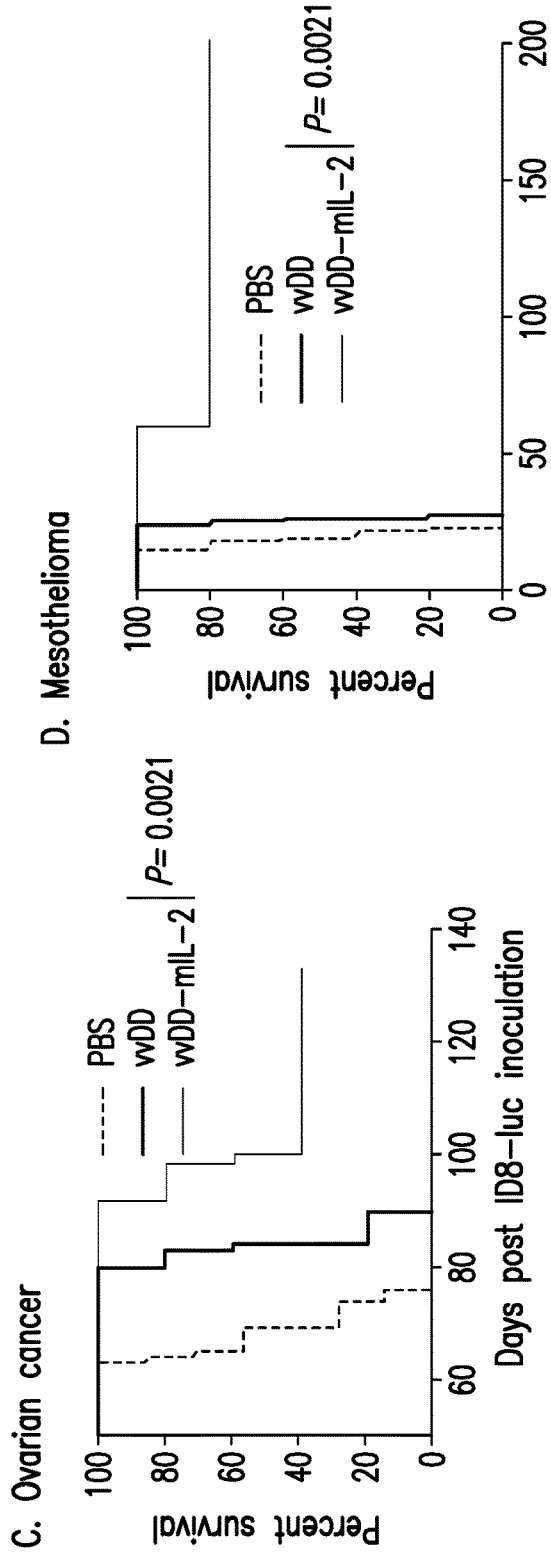
FIG. 1A
FIG. 1B
FIG. 1C
FIG. 1D

A. Experimental scheme

B. Long-term survival of MC38-colon cancer-bearing mice treated on day 9: Mice died due to toxicity of secreted IL-2 vvDD-IL-2 treated group

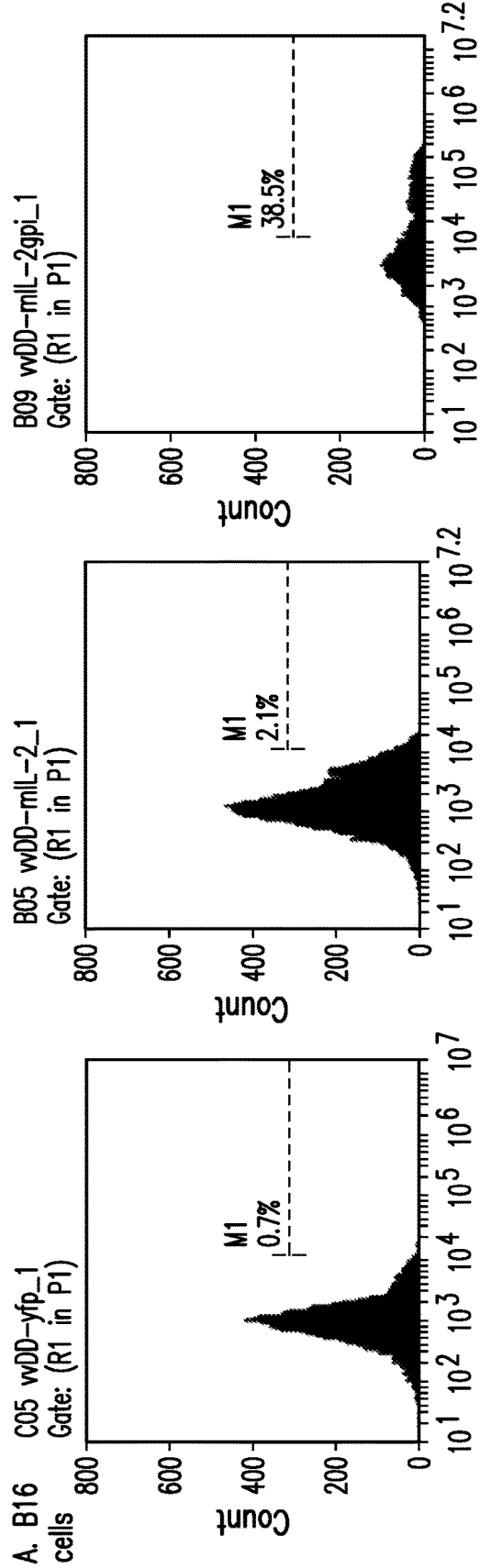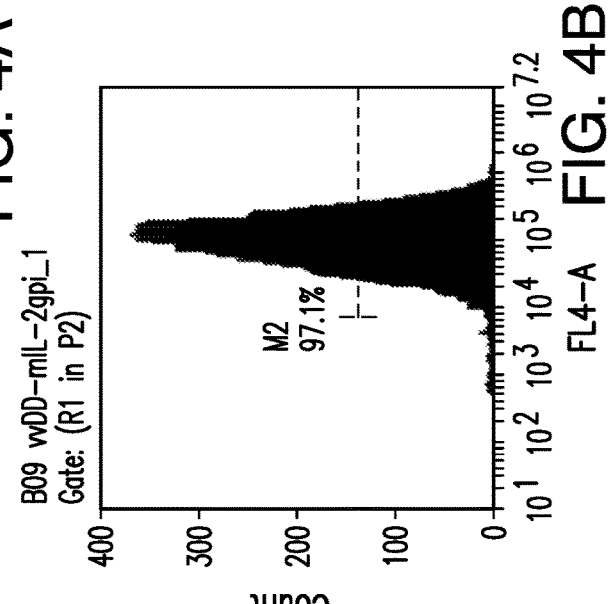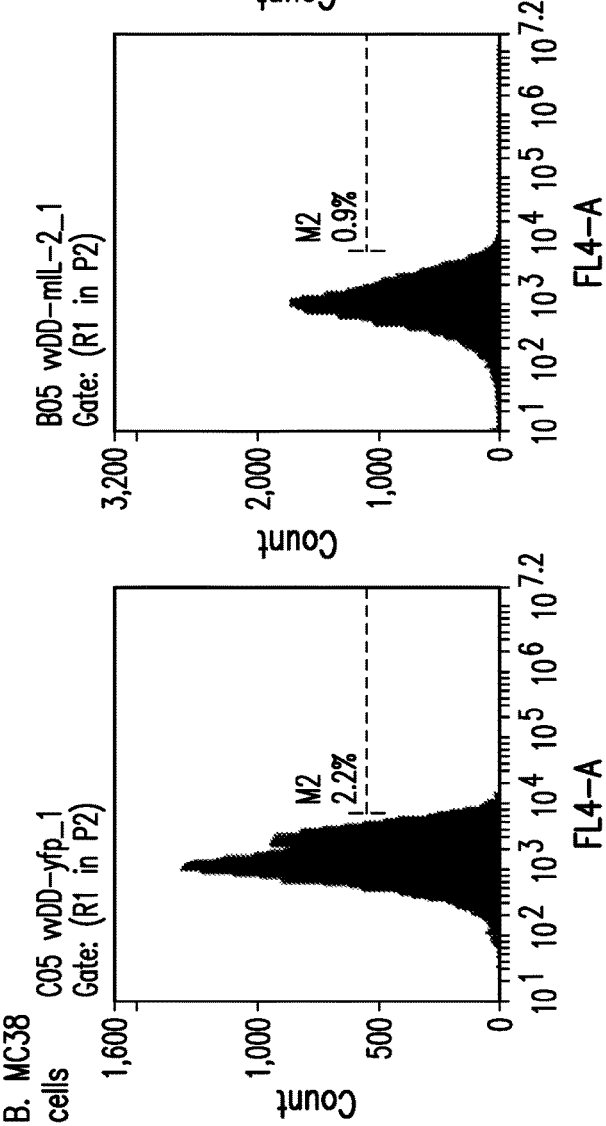
FIG. 4A
FIG. 4B

A. Experimental scheme

B. Survival

A. Experimental scheme

B. Toxity

A. Experimental Scheme

B. Survival

T-cell transfer of vvDD-IL2 induced T-cells

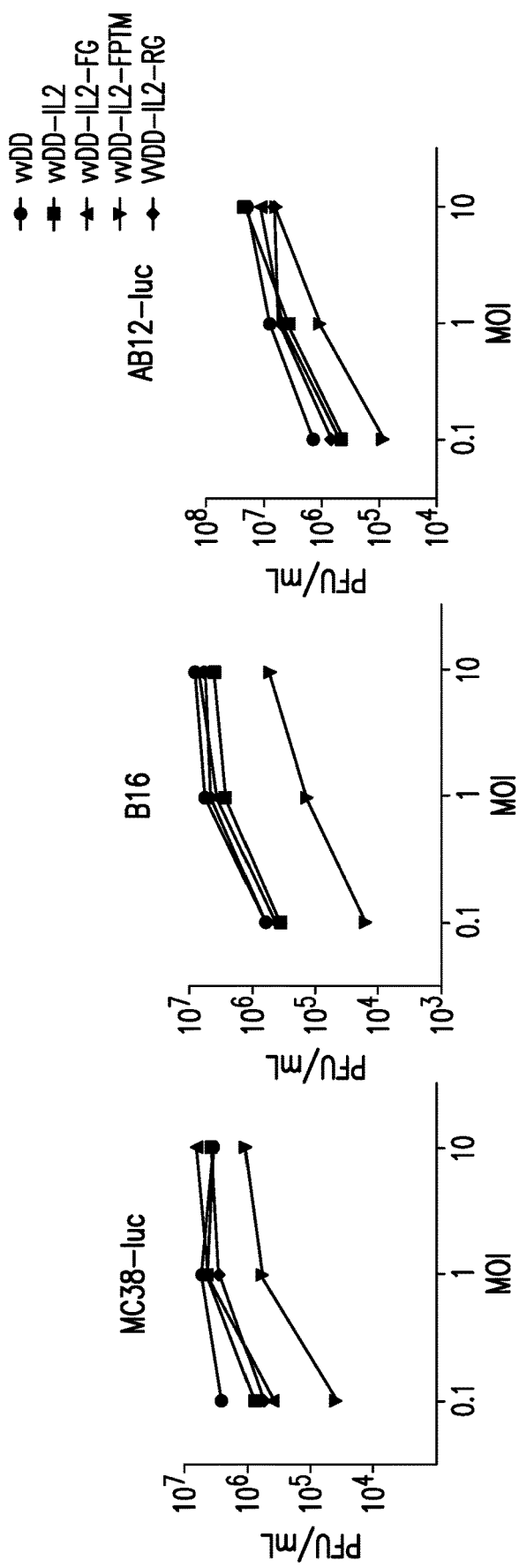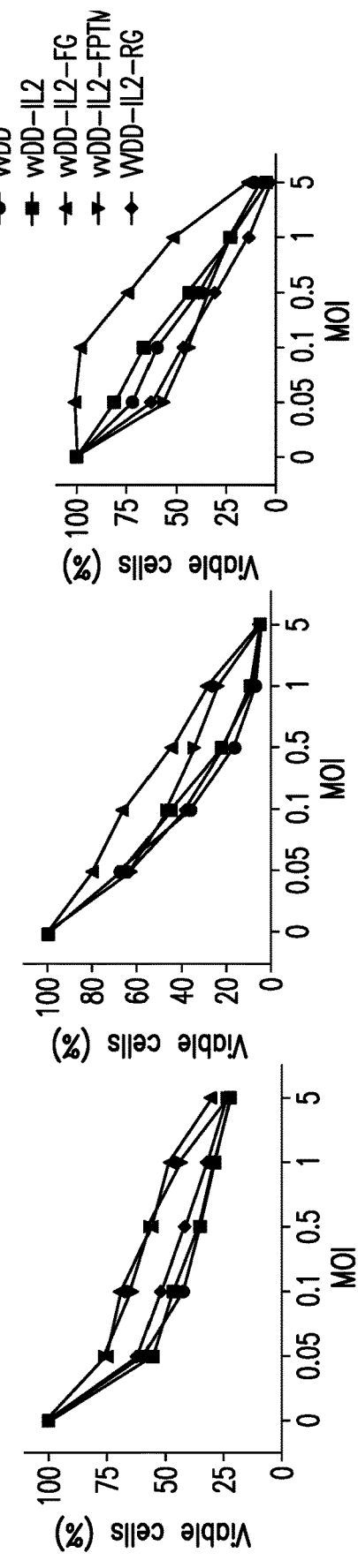
FIG. 10A
FIG. 10B

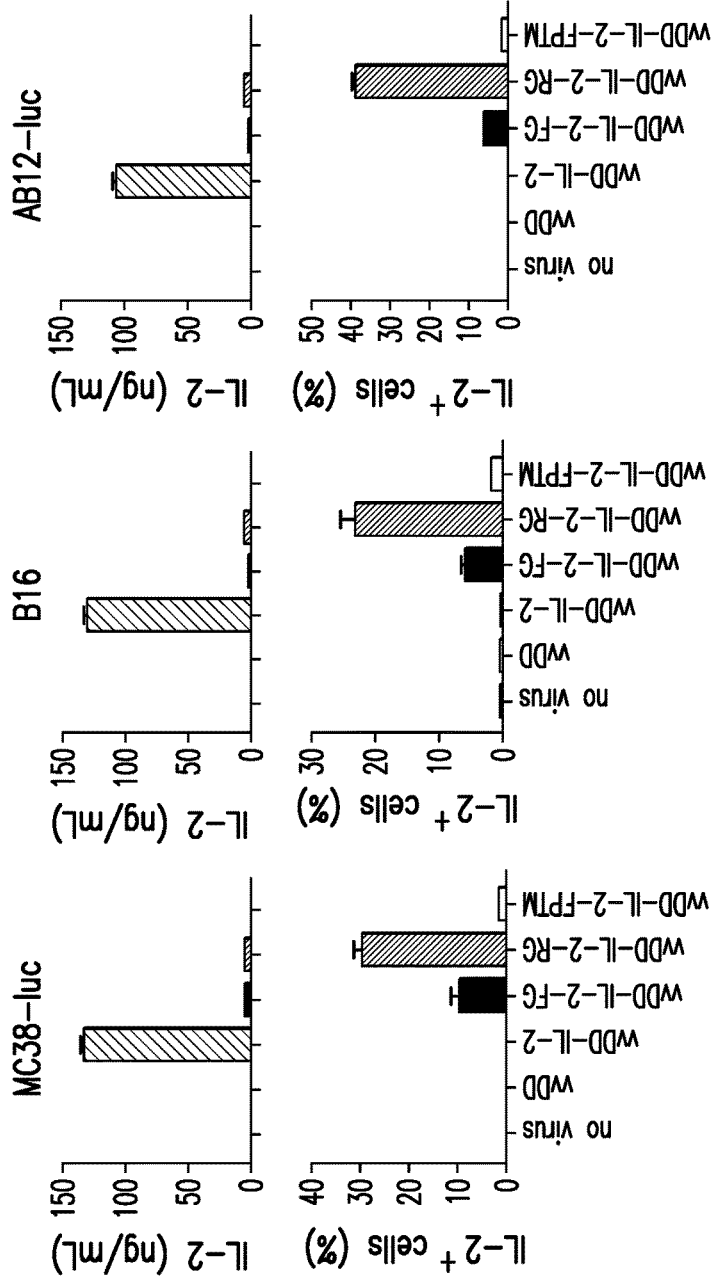
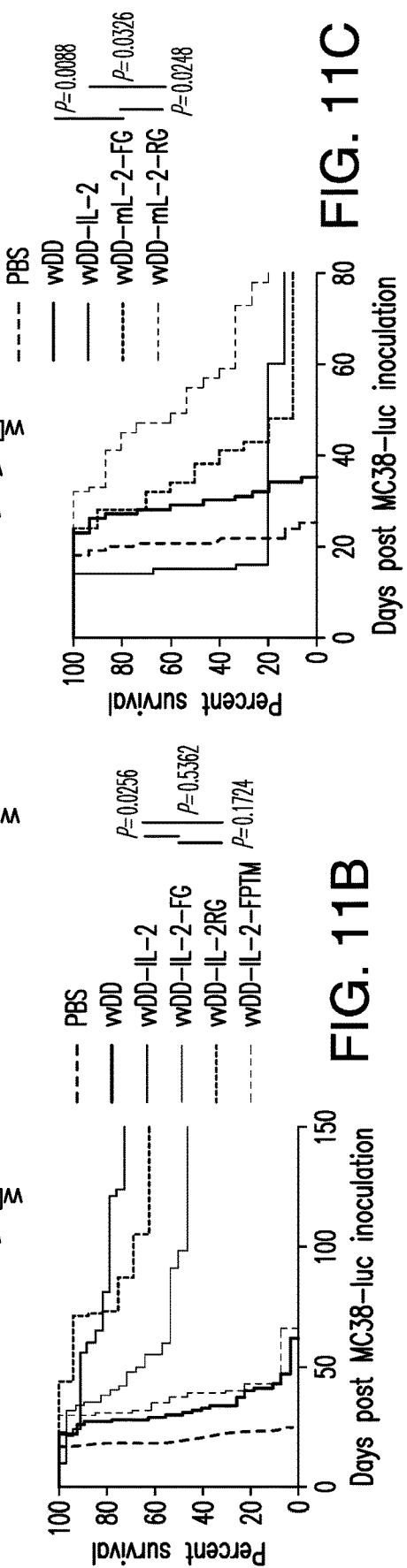
FIG. 11A
FIG. 11B
FIG. 11C

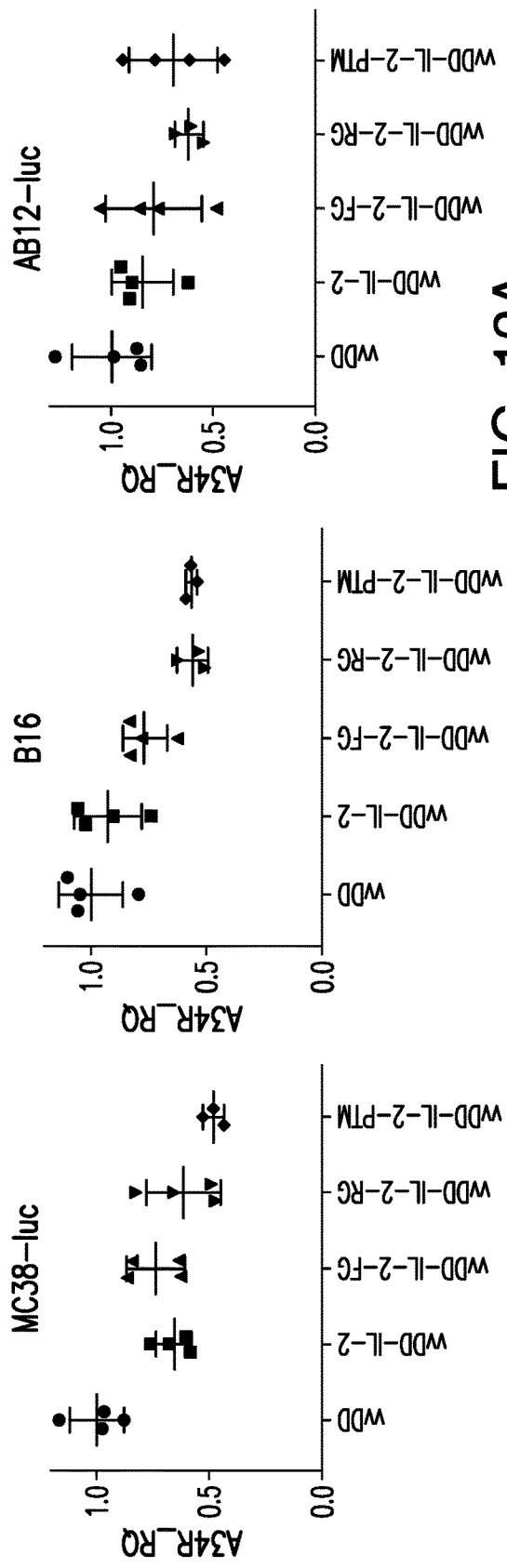
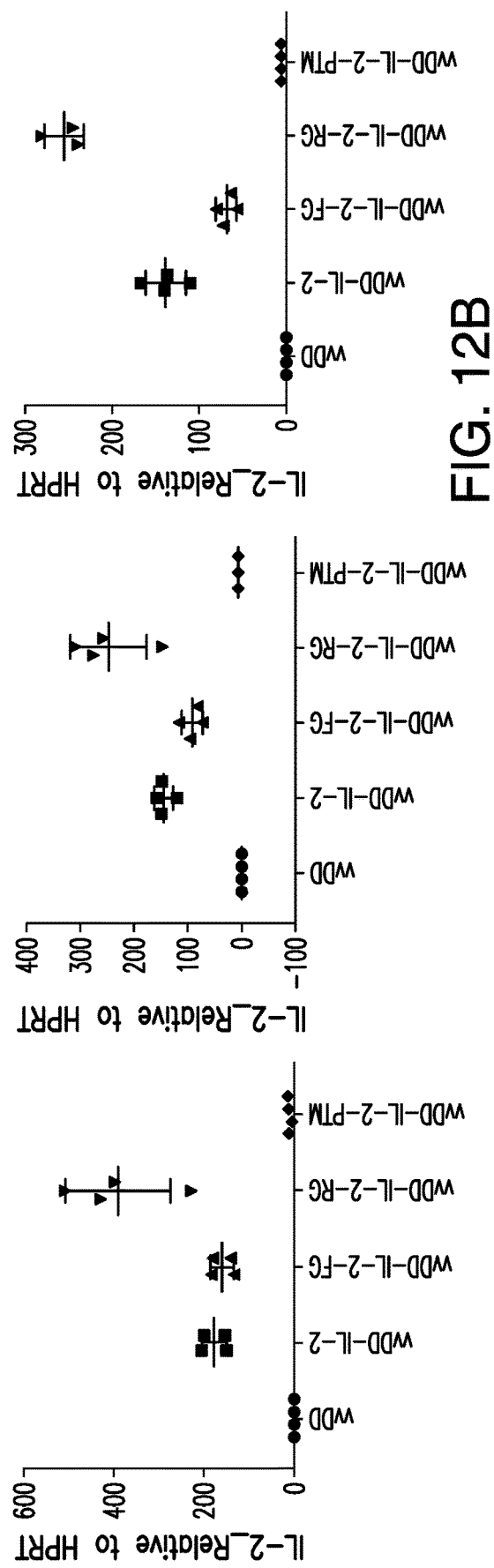
FIG. 12A
FIG. 12B

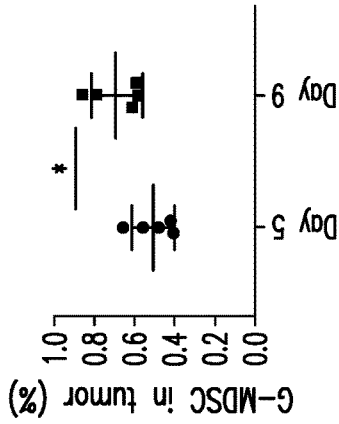
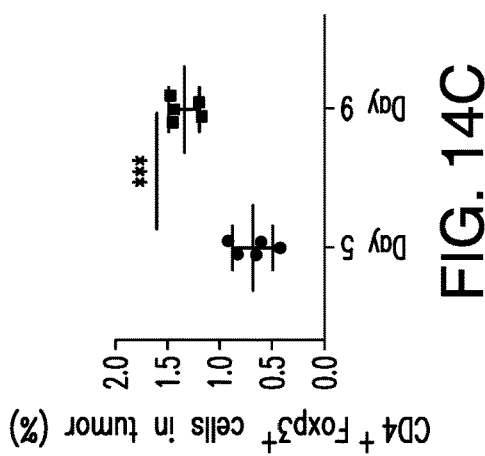
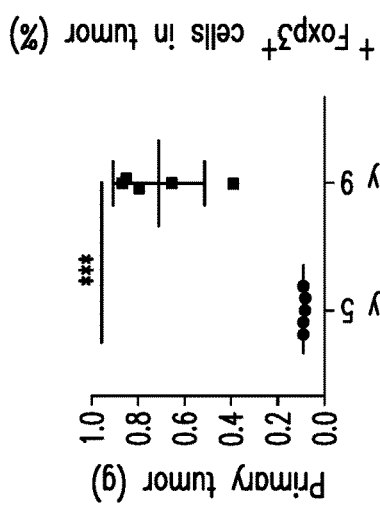
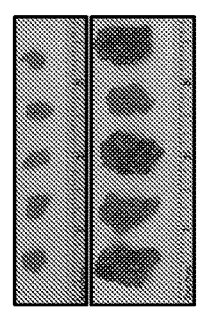
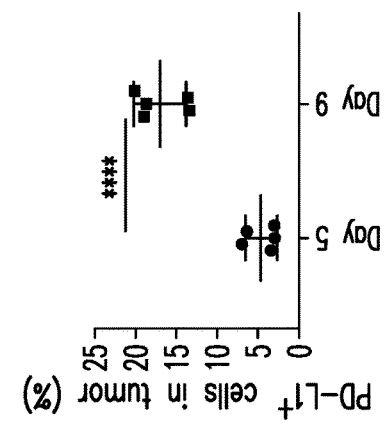
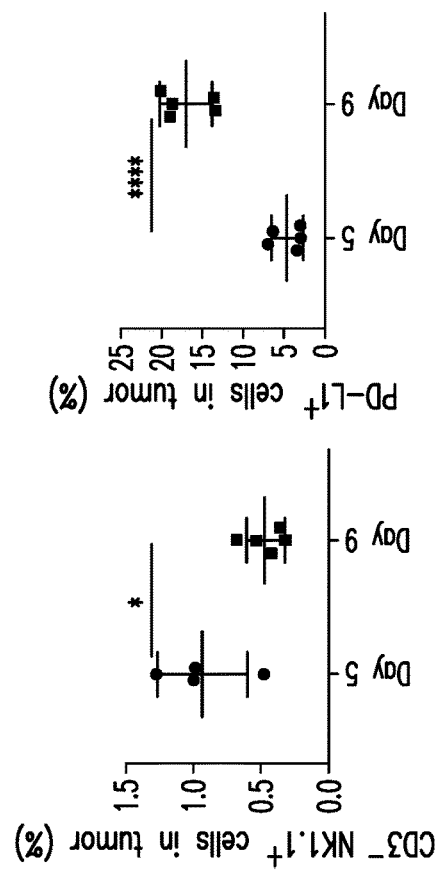
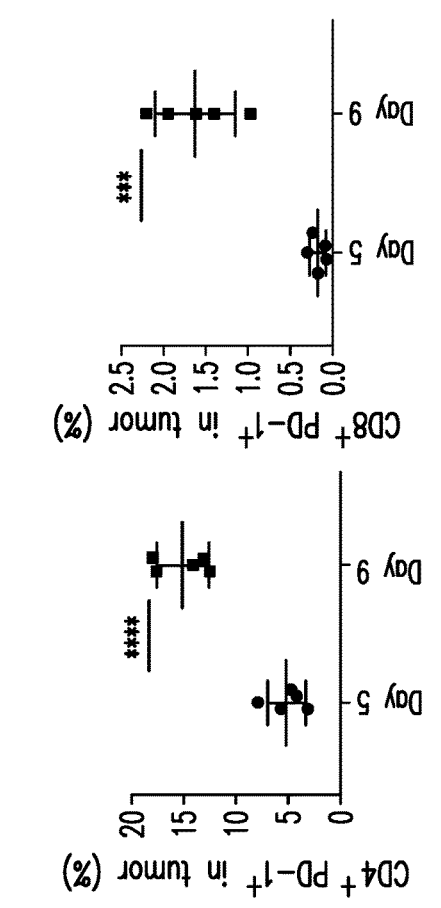
FIG. 14A  FIG. 14B  FIG. 14C  FIG. 14D
FIG. 14E  FIG. 14F  FIG. 14G  FIG. 14H

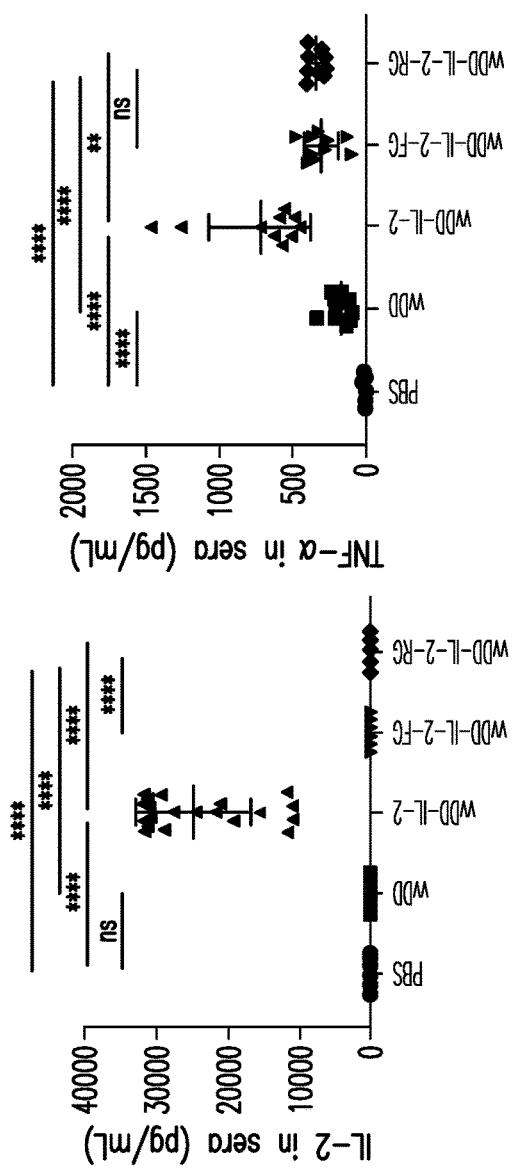
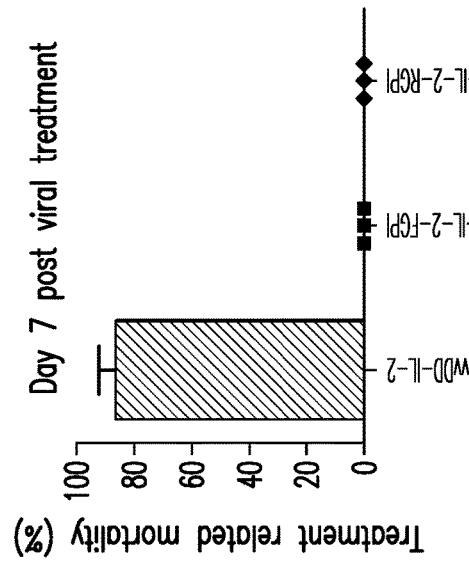
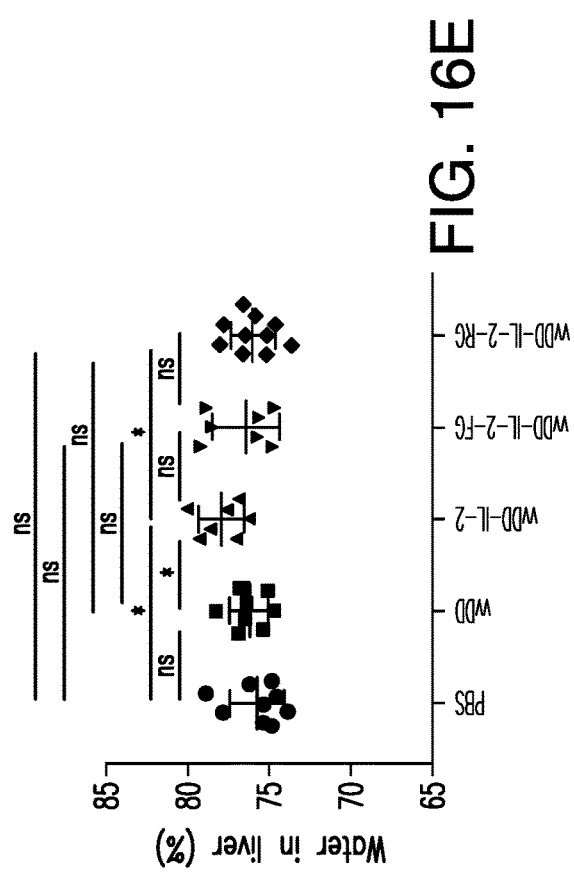
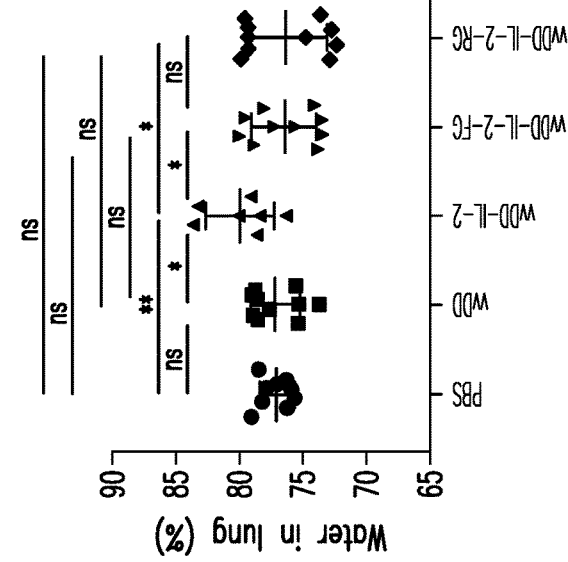
FIG. 16A  FIG. 16B  FIG. 16C  FIG. 16D  FIG. 16E

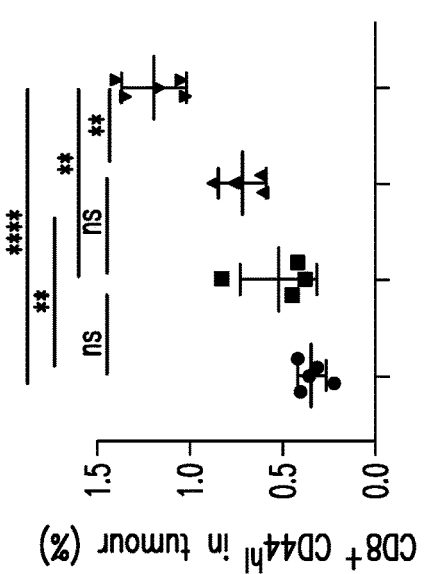
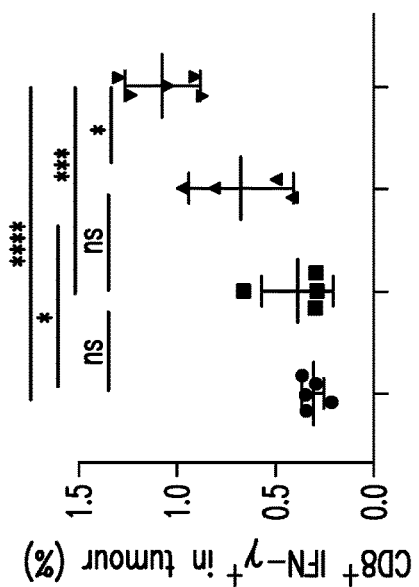
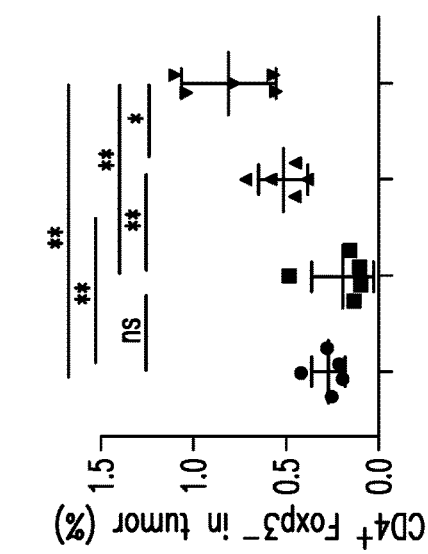
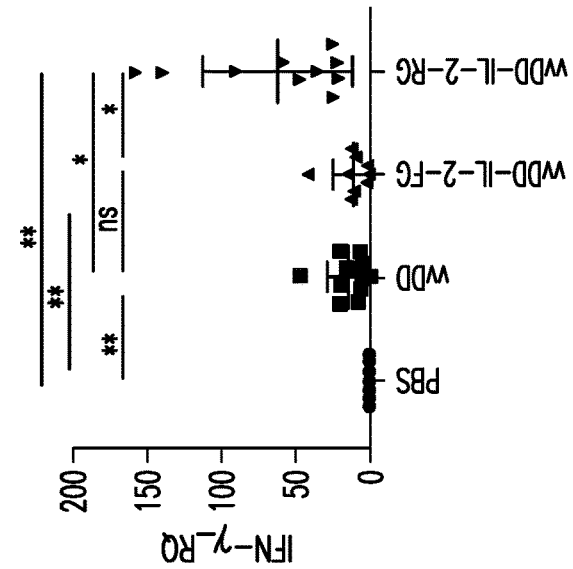
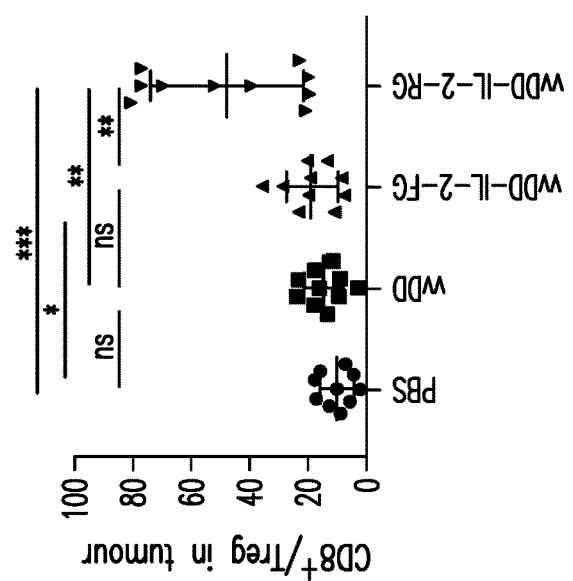
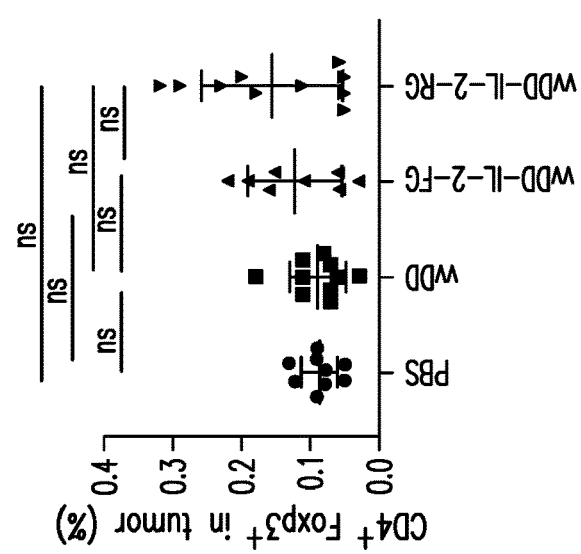
FIG. 18A  FIG. 18B  FIG. 18C
FIG. 18D  FIG. 18E  FIG. 18F

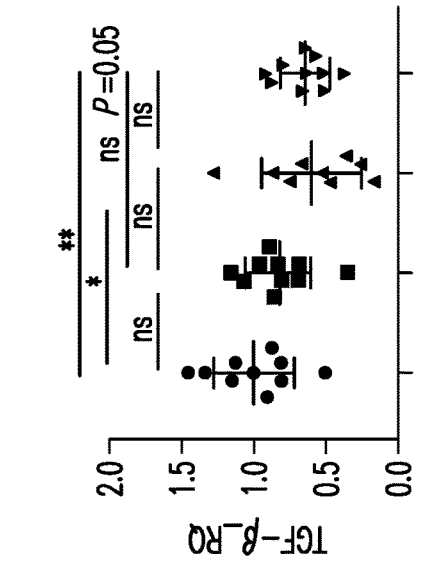
FIG. 18I
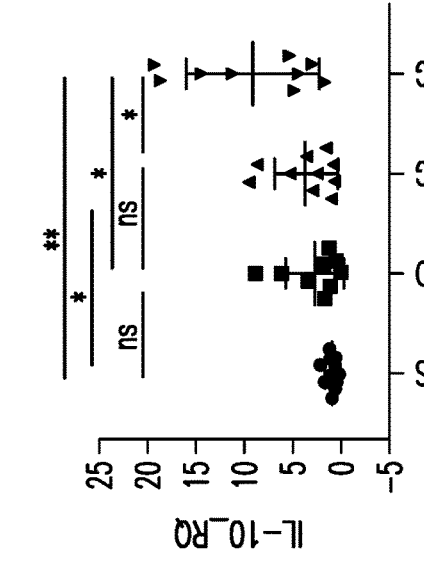
FIG. 18H
FIG. 18G
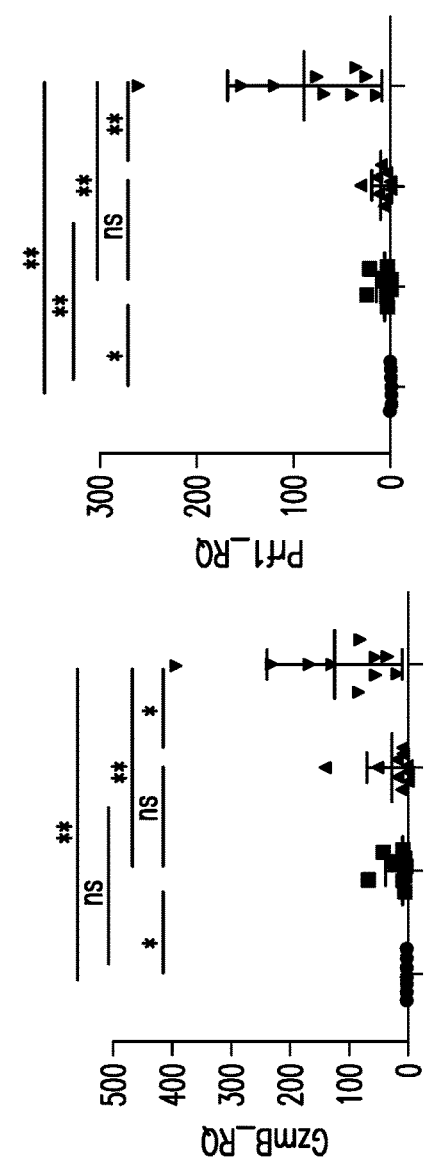
FIG. 18L
FIG. 18K
FIG. 18J

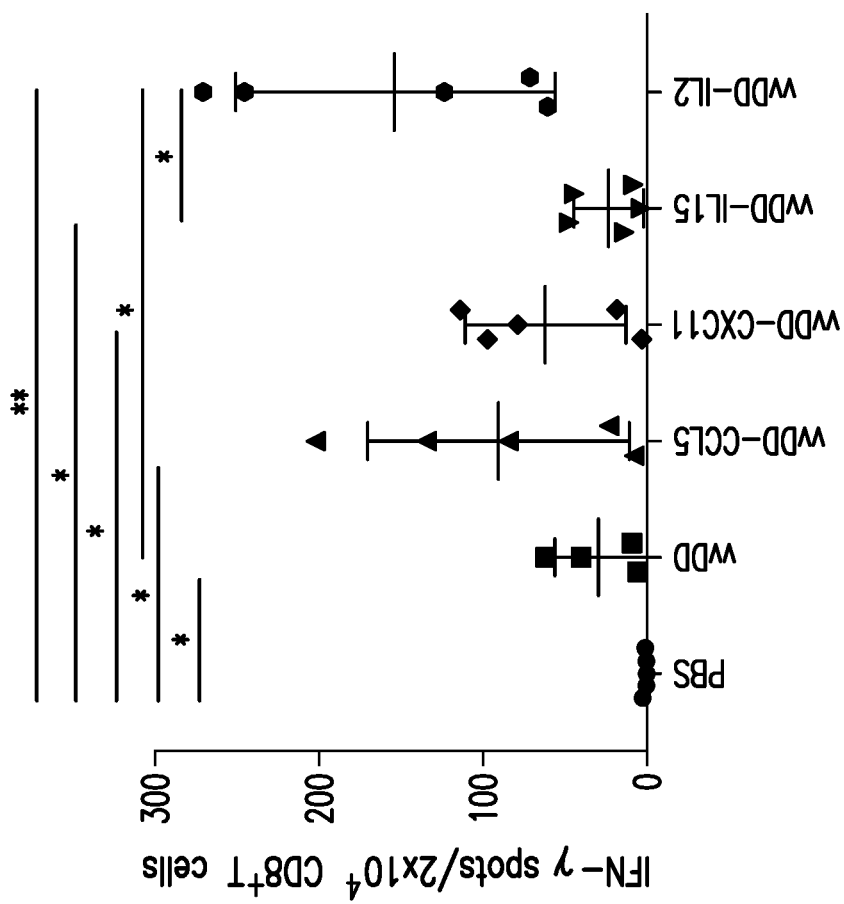
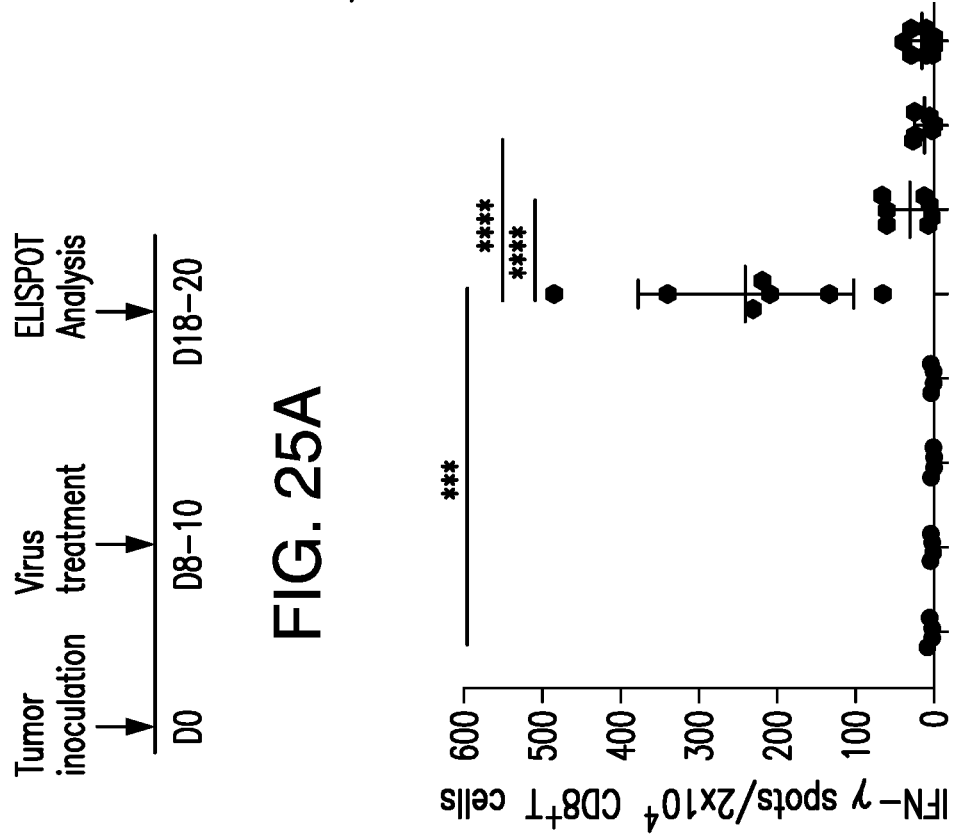
FIG. 25A
FIG. 25B
FIG. 25C

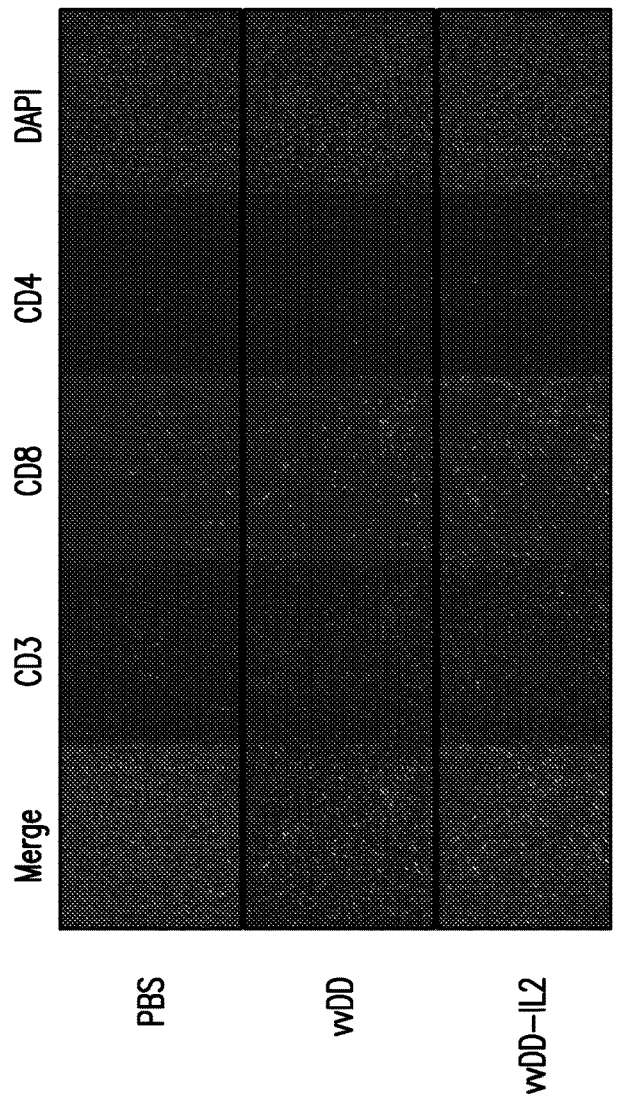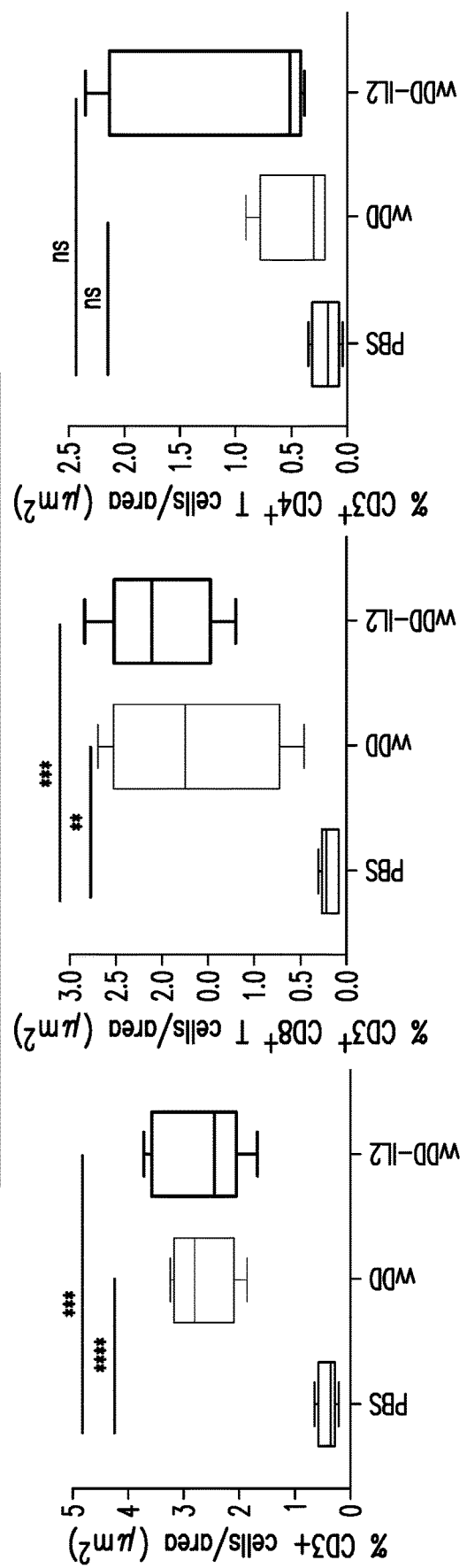
FIG. 27A
FIG. 27B

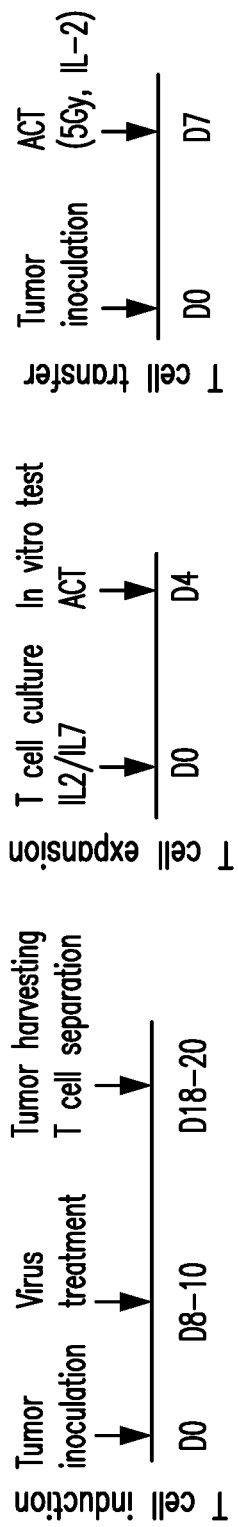
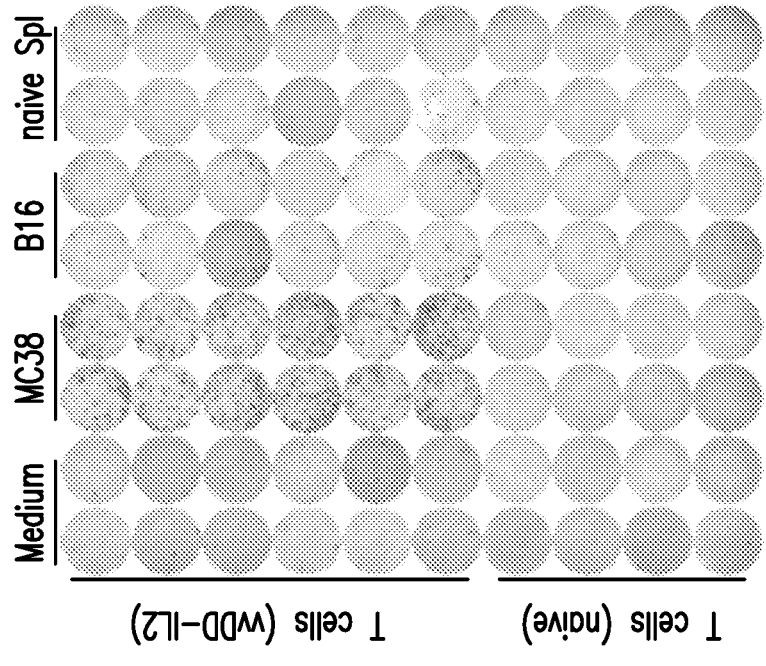
FIG. 31A
FIG. 31B

ONCOLYTIC VIRUS THERAPY

CROSS-REFERENCE TO RELATED APPLICATIONS

This patent application is a National Stage application under 35 U.S.C. § 371 of International Application No. PCT/US2018/016912, having an International Filing Date of Feb. 5, 2018, which claims the benefit of priority to U.S. Provisional Application No. 62/454,526, filed on Feb. 3, 2017. The disclosures of the prior applications are considered part of (and are incorporated by reference in) the disclosure of this application.

GRANT INFORMATION

None applicable.

1. INTRODUCTION

The presently disclosed subject matter relates to oncolytic viruses, armed oncolytic viruses encoding, in an expressible form, an immunomodulator molecule, and to compositions of, and methods of making and using said oncolytic viruses. The presently disclosed subject matter also relates to tumor infiltrated T cells—induced by oncolytic virus ("OV-induced T cells"), and to methods of making and using said OV-induced T cells for adoptive T-cell therapy.

2. BACKGROUND OF THE INVENTION

Oncolytic viruses, which selectively replicate in and kill cancer cells, exert their anti-cancer effects through a number of modalities (Bartlett D L et al., 2013, Molecular Cancer 12:103-120). The first, as their name implies, is cell lysis, which can be achieved through apoptosis, necrosis, pyroptosis, autophagy, or a combination of these (Guo Z S et al., 2014, Front Oncol 4:74). Further, oncolytic viruses can attack a cancer's blood supply, leading to apoptosis and necrosis of infected as well as non-infected cells. Finally, oncolytic viruses induce immunogenic cell death (ICD) of cancer cells, release and present danger signal molecules (signal 0), along with inflammatory cytokines, and cross-present tumor-associated antigens (TAAs) to naïve T cells, leading to elicitation of anti-tumor immunity (Guo Z S et al., 2014, Front Oncol 4:74). The potent oncolytic viruses not only elicit potent and systemic adaptive antitumor immunity, but also promote the trafficking of tumor-specific CD8+ T cells into the tumor tissues (Bartlett D L et al., 2013, Mol Cancer 12:103; Guo Z S et al., 2017, 8:555).

This immune response against the cancer is not restricted to infected cancer cells, but extends to metastatic lesions. The approval of the first-in-class drug, T-VEC, by the FDA to treat advanced melanoma in 2015, showcased the potential of this type of novel treatment for cancer (Andtbacka R H et al., 2015, J Clin Oncol 33:2780-8). Despite their advantages, oncolytic viruses have, to date, faced challenges, including gaining access to cancer cells within tumor nodules in adequate numbers, anti-virus immune responses, and a highly immunosuppressive tumor environment (Zou W., 2005, Nat Rev Cancer 5:263-74). In addition, infiltration of tumor-specific T cells, if they indeed are generated and activated, encounter hurdles, the major one being to infiltrate to tumor tissue where they exert their cytotoxicity to cancer cells and associated stromal cells.

These challenges would be desirably improved by agents that modulate the immune system—for example agents that increase anti-cancer immunity and/or decrease anti-virus immunity. However, agents capable of such immunomodulation—cytokines and the like—can have profound, potentially dangerous effects on a treated subject when systemically dispersed.

3. SUMMARY OF THE INVENTION

The presently disclosed subject matter relates to compositions and methods which promote anti-cancer immunity in the context on oncolytic virus therapy. In certain embodiments, adoptive T cell therapy is used as part of an anti-cancer regimen employing oncolytic virus to promote an immune response against cancer cells, and the oncolytic virus is optionally administered with an immunomodulator. In certain embodiments, the immunomodulator is linked to the oncolytic virus.

In certain embodiments, the presently disclosed subject matter provides a method for generating tumor infiltrating oncolytic-virus induced T cells, comprising:

(a) administering, to a subject having a cancer, an effective amount of an oncolytic virus to induce the infiltration of one or more T cells into the cancer;

(b) isolating the tumor-infiltrated T cells from the cancer of the subject; and (c) expanding the tumor-infiltrated T cells ex vivo.

In certain embodiments, the presently disclosed subject matter provides a method of treating a subject suffering from cancer, comprising administering to the subject one or more tumor infiltrating oncolytic-virus induced T cells disclosed herein.

In certain embodiments, the presently disclosed subject matter provides a method of treating a subject suffering from cancer, comprising:

(a) administering, to the subject, an effective amount of an oncolytic virus to induce the infiltration of one or more T cells into the cancer;

(b) isolating the tumor-infiltrated T cells from the cancer of the subject;

(c) expanding the tumor-infiltrated T cells ex vivo; and (d) transferring the expanded tumor-infiltrated T cells to the subject suffering from cancer.

In certain embodiments, the oncolytic virus is a vaccinia virus. In certain embodiments, the oncolytic virus is a recombinant vaccinia virus with an inactivating mutation of its thymidine kinase gene, vaccinia growth factor gene, or both. In certain embodiments, the oncolytic virus is a herpes simplex virus. In certain embodiments, the oncolytic virus is an adenovirus.

In certain embodiments, the tumor-infiltrated T cells are expanded ex vivo in the presence of IL-2 and IL-7. In certain embodiments, expanding the tumor-infiltrated T cells comprises co-culturing the tumor-infiltrated T cells with dendritic cells and cancer cells. In certain embodiments, expanding the tumor-infiltrated T cells comprises culturing the tumor-infiltrated T cells with cytokines and/or agents. In certain embodiments, the cytokines and/or the agents comprise one or more of IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, IFN-alpha, IFN-alpha2, IFN-beta, or IFN-gamma, TNF-alpha, TNF-beta, and GM-CSF. In certain embodiments, expanding the tumor-infiltrated T cells comprises culturing the tumor-infiltrated T cells with IL-2, IL-7, and/or GSK3b.

In certain embodiments, the subject suffering from cancer is treated with a cancer therapy before transferring the tumor-infiltrated T cells to the subject suffering from cancer.

In certain embodiments, the subject suffering from cancer is further treated with a cancer therapy. In certain embodiments, the subject suffering from cancer is further with one or more exogenous cytokine and/or agent. In certain embodiments, the subject suffering from cancer is further provided with exogenous IL-2, after transferring the tumor-infiltrated T cells.

In certain embodiments, the tumor-infiltrated cells are transferred intraperitoneally or intratumorally. In certain embodiments, the presently disclosed subject matter is directed to the use of an oncolytic virus for treating a subject having cancer.

In certain embodiments, the presently disclosed subject matter is directed to the use of an oncolytic virus for generating tumor infiltrating oncolytic-virus induced T cells. In certain embodiments, the presently disclosed subject matter is directed to the use of tumor infiltrating oncolytic-virus induced T cells for treating a subject having cancer.

In certain embodiments, the tumor infiltrating oncolytic-virus induced T cells are generated by a method comprising:
(a) administering, to a subject having a cancer, an effective amount of an oncolytic virus to induce the infiltration of one or more T cells into the cancer;
(b) isolating the tumor-infiltrated T cells from the cancer of the subject; and
(c) expanding the tumor-infiltrated T cells ex vivo.

In various embodiments, the presently disclosed subject matter provides for the oncolytic viruses, the induced tumor-infiltrated T cells, therapeutic compositions comprising said viruses and T cells, and methods of treating subjects suffering from conditions that would benefit from immunomodulation, including patients suffering from various cancers.

In certain embodiments, the presently disclosed subject matter provides an oncolytic virus encoding a membrane-associated protein comprising an immunomodulator molecule linked to an anchoring peptide. In certain embodiments, the presently disclosed subject matter provides an oncolytic virus comprising, in its genome, a nucleic acid encoding a membrane-associated protein comprising an immunomodulator molecule linked to an anchoring peptide.

In certain embodiments, the oncolytic virus is a vaccinia virus. In certain embodiments, the oncolytic virus is a recombinant vaccinia virus with an inactivating mutation of its thymidine kinase gene, vaccinia growth factor gene, or both. In certain embodiments, the nucleic acid encoding the immunomodulatory molecule linked to the anchoring peptide is operably linked to the p7.5 e/l promoter.

In certain embodiments, the anchoring peptide comprises a GPI-anchor acceptor peptide or a PD-L1 transmembrane domain. In certain embodiments, the immunomodulator molecule is joined to the anchoring peptide via a linker peptide. In certain embodiments, the linker is a flexible linker or a rigid linker. In certain embodiments, the immunomodulator molecule is interleukin-2 and/or interferon-gamma, and/or tumor necrosis factor-alpha.

In certain embodiments, an oncolytic virus is administered as a therapeutic composition. In certain embodiments, the presently disclosed subject matter provides a therapeutic composition comprising an oncolytic virus together with a physiologic buffer. In certain embodiments, the therapeutic composition is in lyophilized form. In certain embodiments, the presently disclosed subject matter provides a syringe comprising an effective amount of the therapeutic composition.

In certain embodiments, the presently disclosed subject matter provides a method of treating a subject suffering from a cancer, comprising administering, to the subject, an effective amount of an oncolytic virus encoding an immunomodulator molecule. In certain embodiments, the immunomodulator molecule is interleukin-2. In certain embodiments, the cancer is locally invasive. In certain embodiments, the cancer is metastatic. In certain embodiments, the oncolytic virus is administered intratumorally. In certain embodiments, a therapeutically effective amount of an immunomodulatory agent is further administered to the subject suffering from a cancer. In certain embodiments, the immunomodulatory agent is an anti-PD-1 or an anti-PD-L1 antibody. In certain embodiments, an additional therapy is provided to the subject suffering from cancer.

4. BRIEF DESCRIPTION OF THE DRAWINGS

FIG. 1A-D. Anti-tumor immunity elicited by viral delivered IL-2. The antitumor effect of vvDD-mIL-2 in murine tumor models: anti-tumor effects of oncolytic vaccinia virus armed with secretable IL-2 on various types of cancer in syngeneic mice. (A) Experimental scheme. (B-D) Percent survival of immunocompetent mice treated with either phosphate buffered saline (PBS; dotted line), unarmed vvDD virus (black line) or mIL-2 "armed" vvDD-mIL-2 (gray line) five days after inoculation with (B) MC38-luc colon cancer cells; (C) ID8-luc ovarian cancer cells; or (D) AB12-luc mesothelioma cells. Specifically, B6 mice were intraperitoneally inoculated with $5 \times 10^5$ MC38-luc cells (MC38 colorectal cancer model in C57BL/6 (B6) mice) (B) or $3.5 \times 10^6$ ID8-luc (ID8 ovarian cancer model in B6 mice) (C) or BALB/c mice were intraperitoneally inoculated with $4 \times 10^5$ AB12-luc (AB12 mesothelioma model in BALB/c mice) (D), and treated with PBS, vvDD and vvDD-IL-2 5 days post tumor inoculation. The survival of tumor-bearing mice was shown by Kaplan-Meier analysis. In all of the figures, the standard symbols for P values are, * $P<0.05$;  $P<0.01$; * $P<0.001$; and **** $P<0.0001$.

Figure 2B:
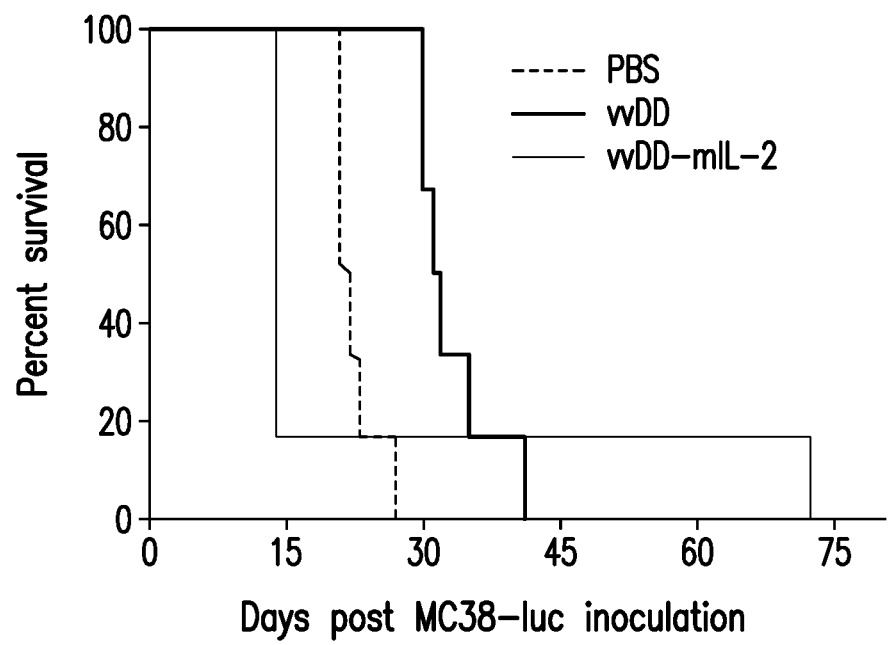

FIG. 2A-B. The toxicity of vvDD-mIL-2 in a late stage murine tumor model: vvDD-mIL-2 elicits strong toxic effects when treating more advanced MC38 colon cancer model in B6 mice. (A) Experimental scheme. (B) Percent survival of mice treated with either phosphate buffered saline (PBS; dotted line), unarmed vvDD virus (black line) or mIL-2 "armed" vvDD-mIL-2 virus (gray line) nine days after inoculation with MC38-luc colon cancer cells. MC38 tumor model is normally treated on day 5. However, when treated on day 9, the expression of secreted IL-2 caused fatal effects in tumor-bearing mice.

Figure 3A:
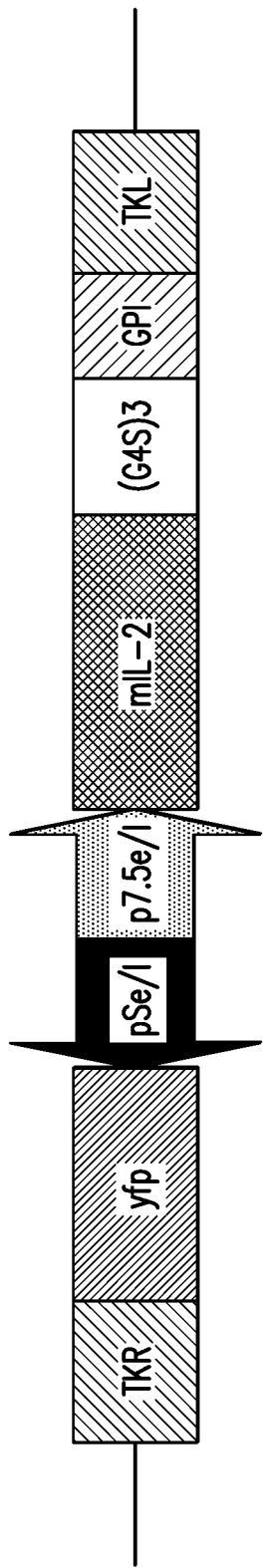
Figure 3B:
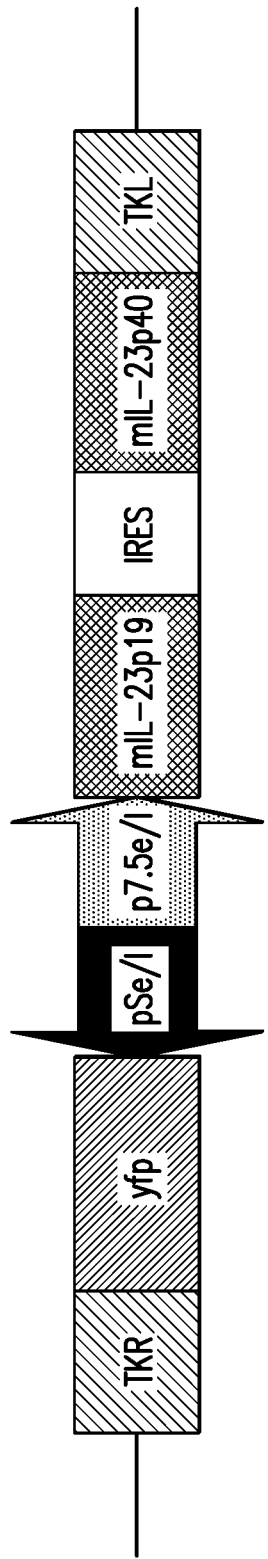

FIG. 3. Examples of oncolytic viruses armed with immune-stimulatory molecules for elicitation of potent adaptive antitumor immunity. The examples include, but not limited to, vvDD-mIL-2-GPI and vvDD-IL-23. (A) Diagram of insertion, in vvDD thymidine kinase (tk) gene, of p7.5 e/l viral promoter operably linked to murine IL-2-encoding nucleic acid fused to (G4S)3 linker and GPI anchor-encoding sequences, in virus denoted vvDD-mIL-2-GPI. This construct also contains nucleic acid encoding yellow fluorescent protein ("yfp") operably linked to the pSe/l promoter as a detectable marker. (B) Diagram of insertion, in vvDD thymidine kinase (tk) gene, of p7.5 e/l viral promoter operably linked to murine IL-23p19-encoding nucleic acid fused to IRES linker and murine IL-23p40 anchor-encoding sequences, in virus denoted vvDD-mIL-23p19-IRES. This construct also contains nucleic acid encoding yellow fluorescent protein ("yfp") operably linked to the pSe/l promoter as a detectable marker.

FIG. 4A-B. Flow cytometry data. (A) B16 melanoma cells infected with either vvD virus (left-most panel), vvDDmIL-2 virus (center panel) or vvDD-mIL-2-GPI virus (rightmost panel). (B) MC38 colon cancer cells infected with either vvD virus (left-most panel), vvDD-mIL-2 virus (center panel) or vvDD-mIL-2-GPI virus (right-most panel).

Figure 5B:
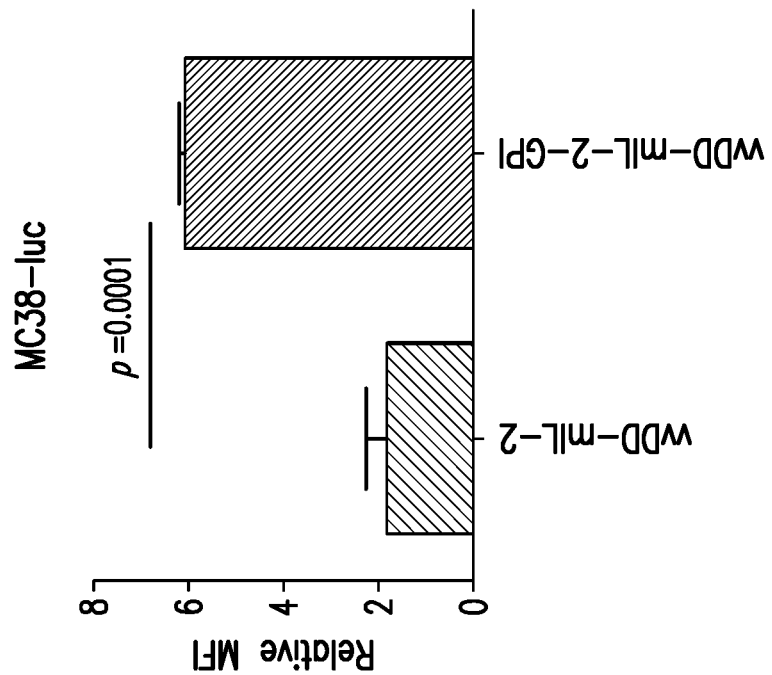
Figure 5A:
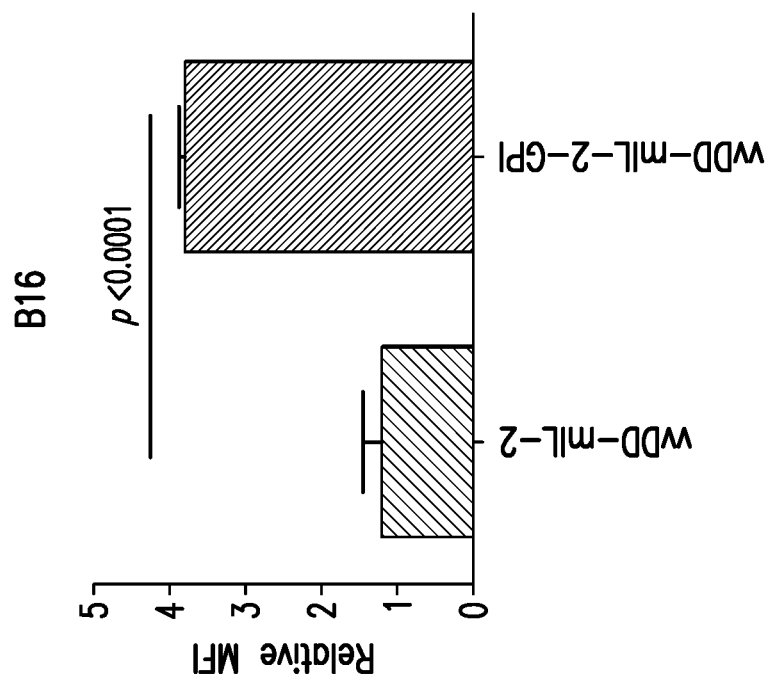

FIG. 5A-B. The expression intensity of IL-2 on cell membrane (A) in B16 cells infected with vvDD-mIL-2 or vvDD-mIL-2-GPI; (B) in MC38-luc cells infected with vvDD-mIL-2 or vvDD-mIL-2-GPI.

Figure 6A:
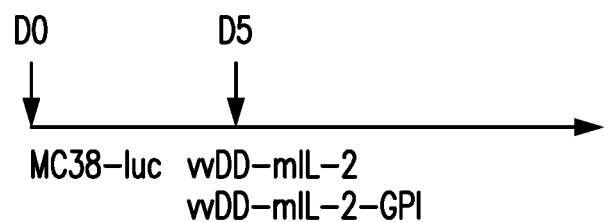
Figure 6B:
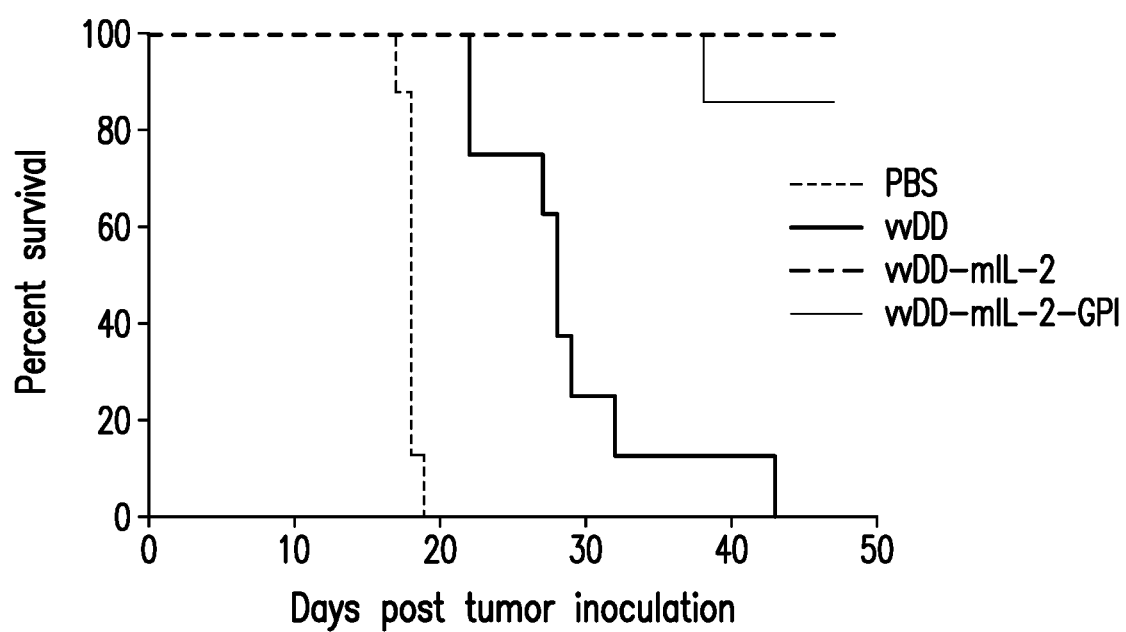

FIG. 6A-B. The oncolytic viruses expressing IL-12 display significant therapeutic effect in early colon cancer model (day 5). (A) Experimental scheme. (B) Percent survival of mice treated with either phosphate buffered saline (PBS; dotted line), vvDD virus (black line), vvDD-mIL-2 virus (thin black line that stays at 100 percent) or IL-2 "anchored" vvDD-mIL-2-GPI (gray line) 5 days after inoculation with MC38-luc colon cancer cells (experimental scheme in upper part of the figure).

Figure 7A:
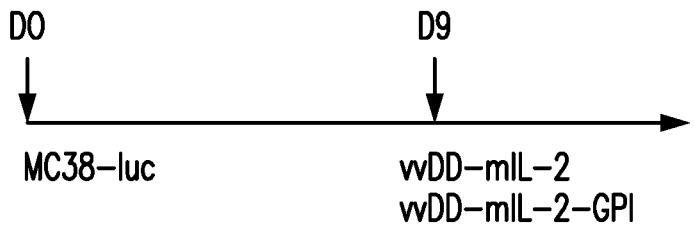
Figure 7B:
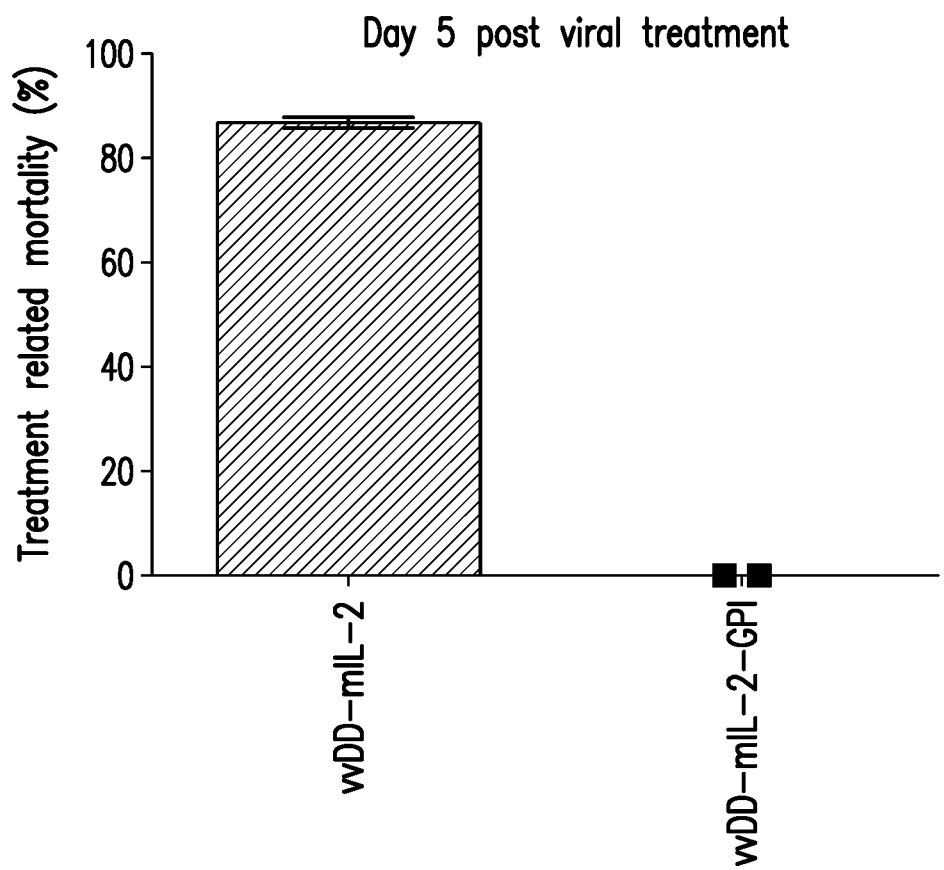

FIG. 7A-B. (A) Experimental scheme. (B) Treatment mortality of MC38-luc tumor-bearing mice treated with either vvDD-mIL-2 (left bar) or vvDD-mIL-2-GPI (right bar) nine days after inoculation with MC38-luc colon cancer cells.

Figure 8A:
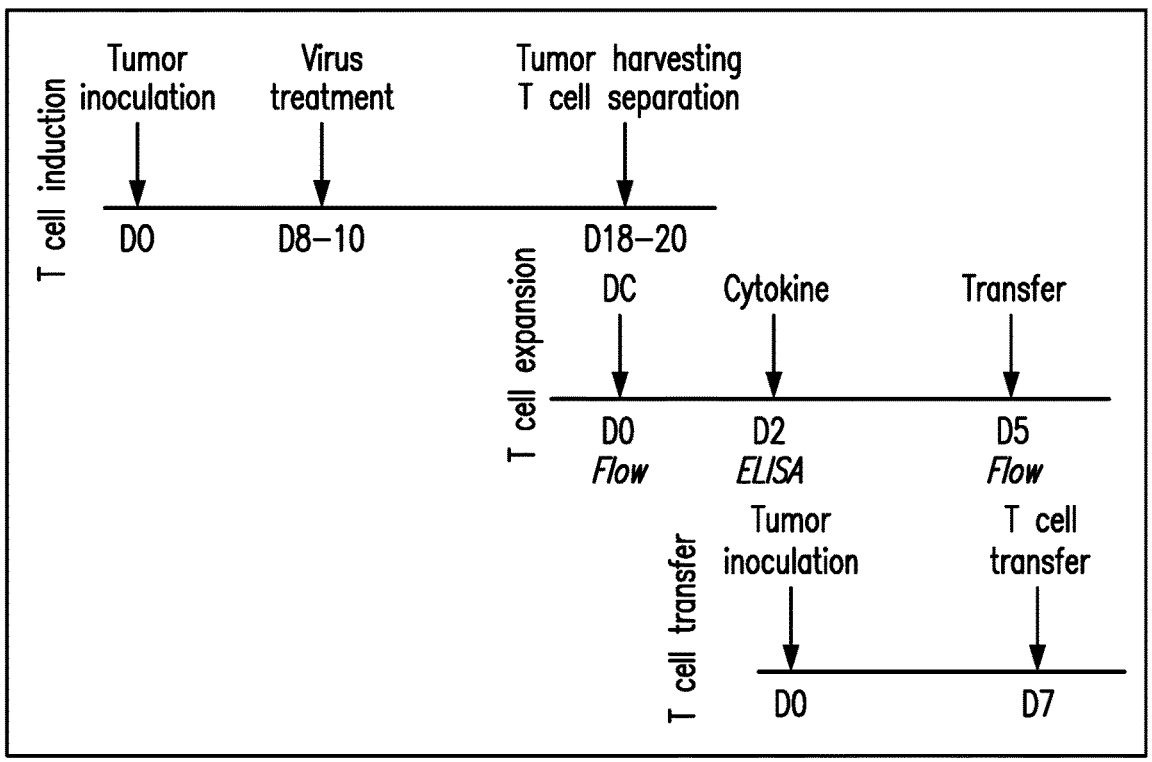
Figure 8B:
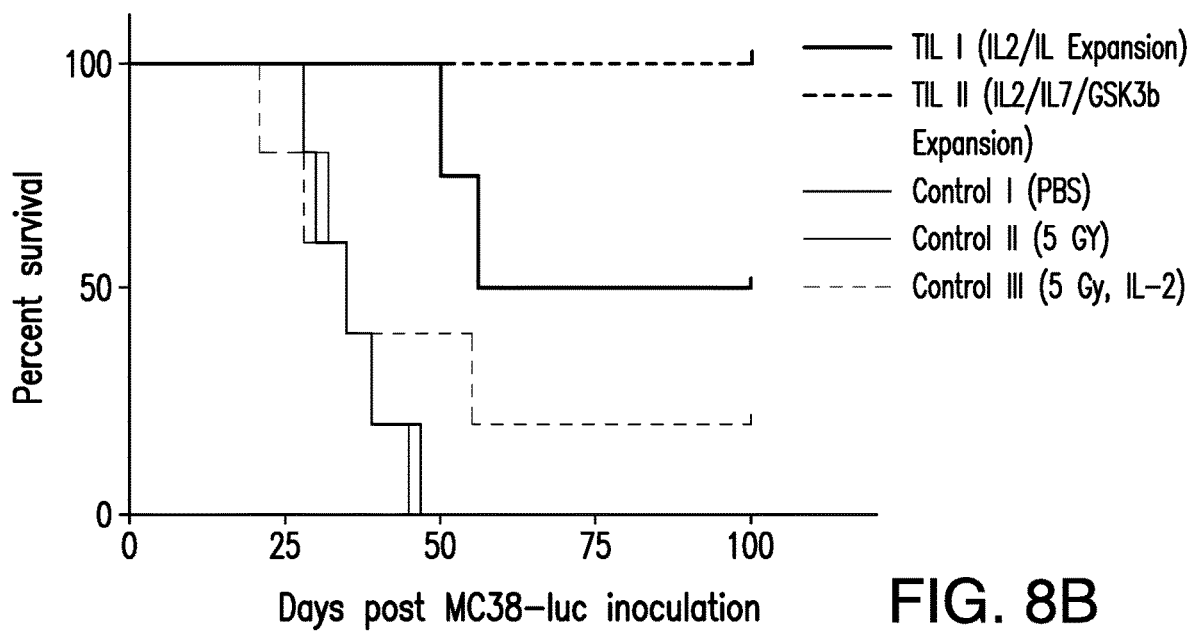
Figure 8C:
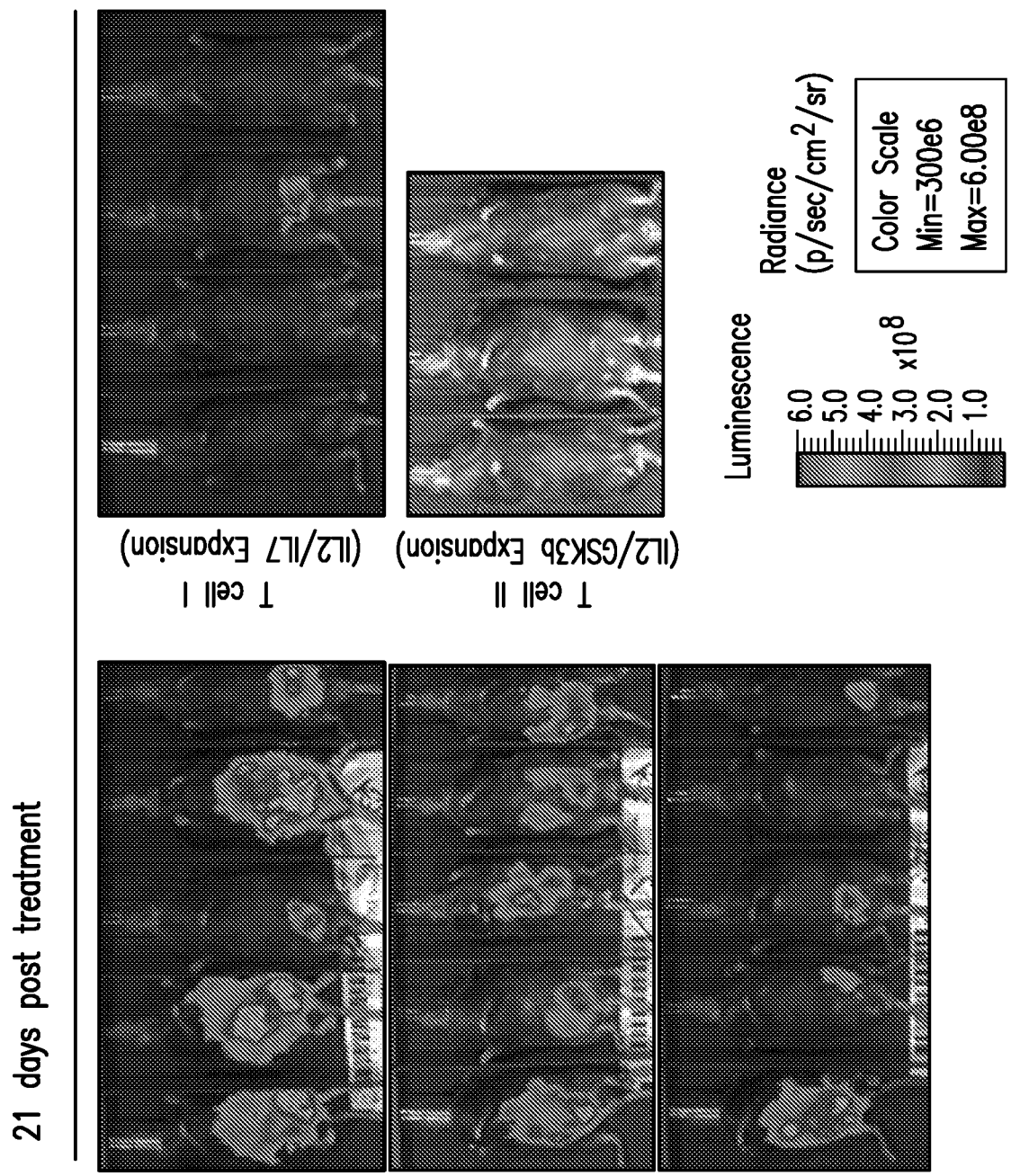
Figure 8D:
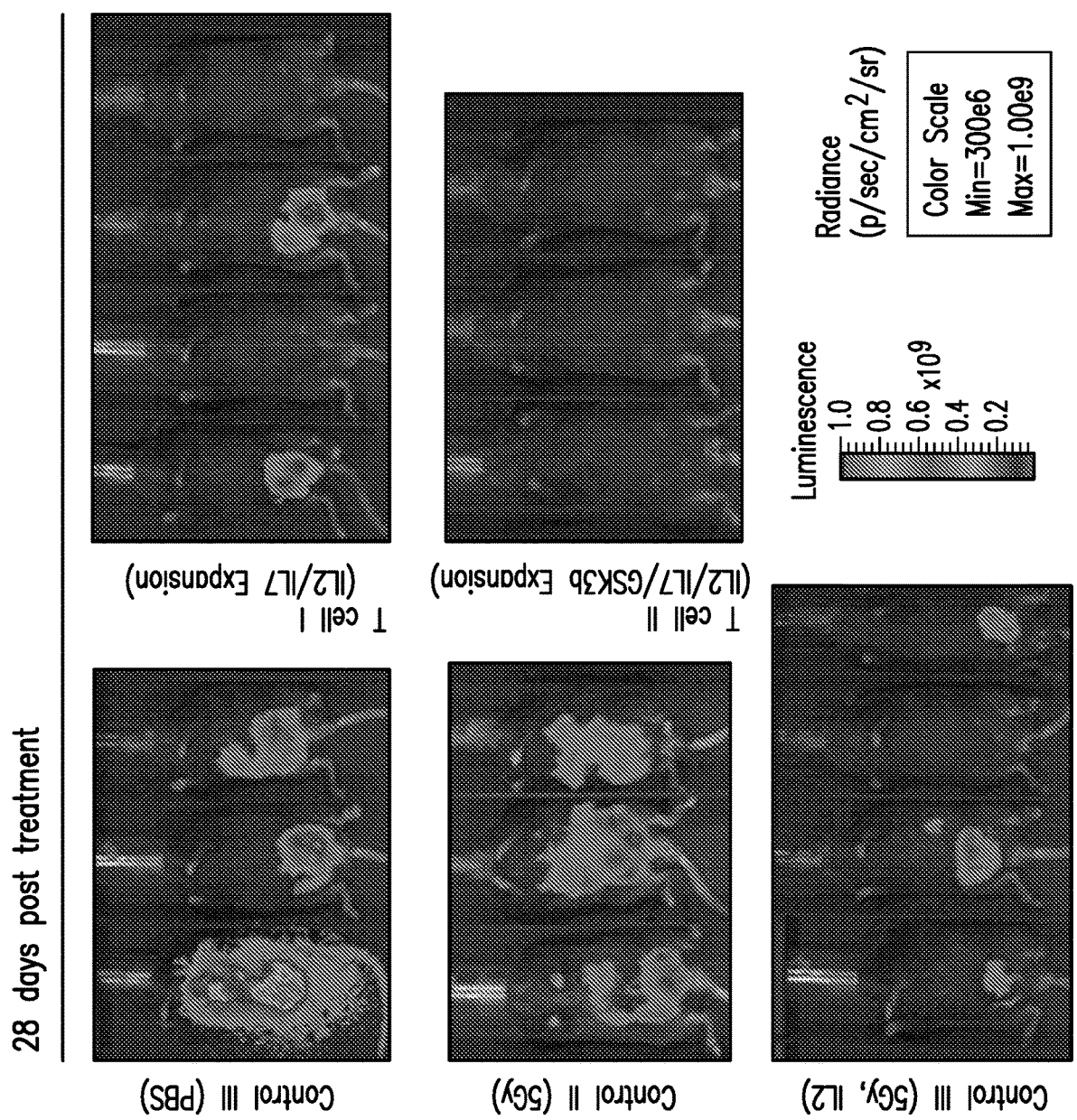

FIG. 8A-C. Adoptive transfer of tumor infiltrated T cells—induced by oncolytic virus ("OV-induced T cells") (isolated from vvDD-IL-2 treated MC38 tumor-bearing mice and ex vivo expanded) led to significant therapeutic effects in syngeneic C57BL/6 mice bearing peritoneal MC38 tumor. (A) Timeline of experimental setup. (B) The survival of tumor-bearing mouse was monitored by Kaplan-Meier analysis. (C) Live imaging of the mice with MC38-luc tumors at day 21 post treatment and (D) at day 28 post treatment.

Figure 9:
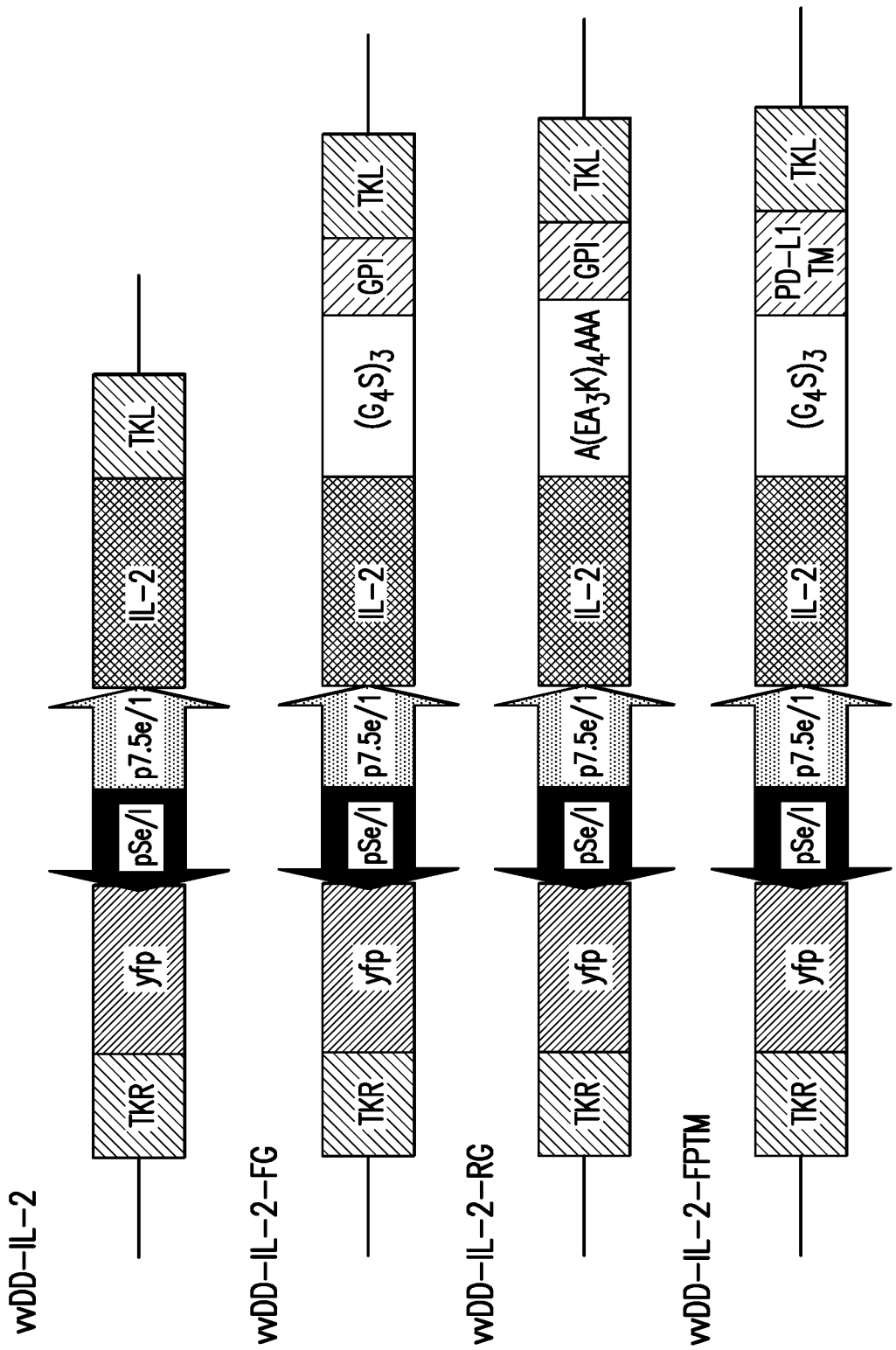

FIG. 9. Schematic diagram of viral IL-2 variants. vvDD-IL-2, vvDD-IL-2-FG, vvDD-IL-2-RG and vvDD-IL-2-FPTM were generated by homologous recombination of murine IL-2 variants into the tk locus of vaccinia viral genome, carrying secreted IL-2, IL-2-flexible linker $(G_4S)_3$-GPI anchor sequence amplified form human CD16b, IL-2-rigid linker A $(EA_3K)_4AAA$-GPI anchor sequence amplified form human CD16b, IL-2-flexible linker $(G_4S)_3$-murine PD-L1 transmembrane domain, respectively. $(G_4S)_3$=SEQ ID NO: 12; $A(EA_3K)_4AAA$ =SEQ ID NO:36.

FIG. 10A-B. Viral replication and cytotoxicity in vitro. Tumor cells MC38-luc, B16 and AB12-luc were mock-infected or infected with indicated viruses. The production of virus progeny from infected cancer cells at 48 h post infection was determined by plaque assay (A), or the viability of viral infected cells was determinate by MTS assay (B).

FIG. 11A-C. The expression and antitumor effect of viral delivered IL-2. (A) Tumor cell MC38-luc ($3\times10^5$ cells), B16 ($2\times10^5$ cells) or AB12-luc ($3\times10^5$ cells) were mock-infected or infected with vvDD, vvDD-IL-2, vvDD-IL-2-FG, vvDD-IL-2-RG and vvDD-IL-2-FPTM at MOI of 1. The culture supernatants were harvested for measuring secreted IL-2 by ELISA or membrane-associated IL-2 by flow cytometry 24 hours post infection. (B) B6 mice were intraperitoneally inoculated with $5\times10^5$MC38-luc cells and treated with PBS, vvDD, vvDD-IL-2, vvDD-IL-2-FG, vvDD-IL-2-RG and vvDD-IL-2-FPTM at $2\times10^8$PFU/mouse 5 days post tumor inoculation. (C) B6 mice were intraperitoneally inoculated with $5\times10^5$MC38-luc cells and treated with PBS, vvDD, vvDD-IL-2, vvDD-IL-2-FG and vvDD-IL-2-RG at $2\times10^8$PFU/mouse 9 days post tumor inoculation. The survival of tumor-bearing mice was shown by Kaplan-Meier analysis. The standard symbols for P values are, * P<0.05;  P<0.01; * P<0.001; and **** P<0.0001.

FIG. 12A-B. Viral delivered IL-2 expression in tumor cells. Tumor cells MC38-luc, B16, or AB12-luc were mock-infected or infected with vvDD, vvDD-IL-2, vvDD-IL-2-FG, vvDD-IL-2-RG and vvDD-IL-2-FPTM at MOI of 1. The infected cells were harvested 24 h post infection for RNA purification. Purified total RNAs were subject to RT-qPCR for quantitative detection of A34R mRNA (viral gene) (A) or IL-2 (B).

Figure 13:
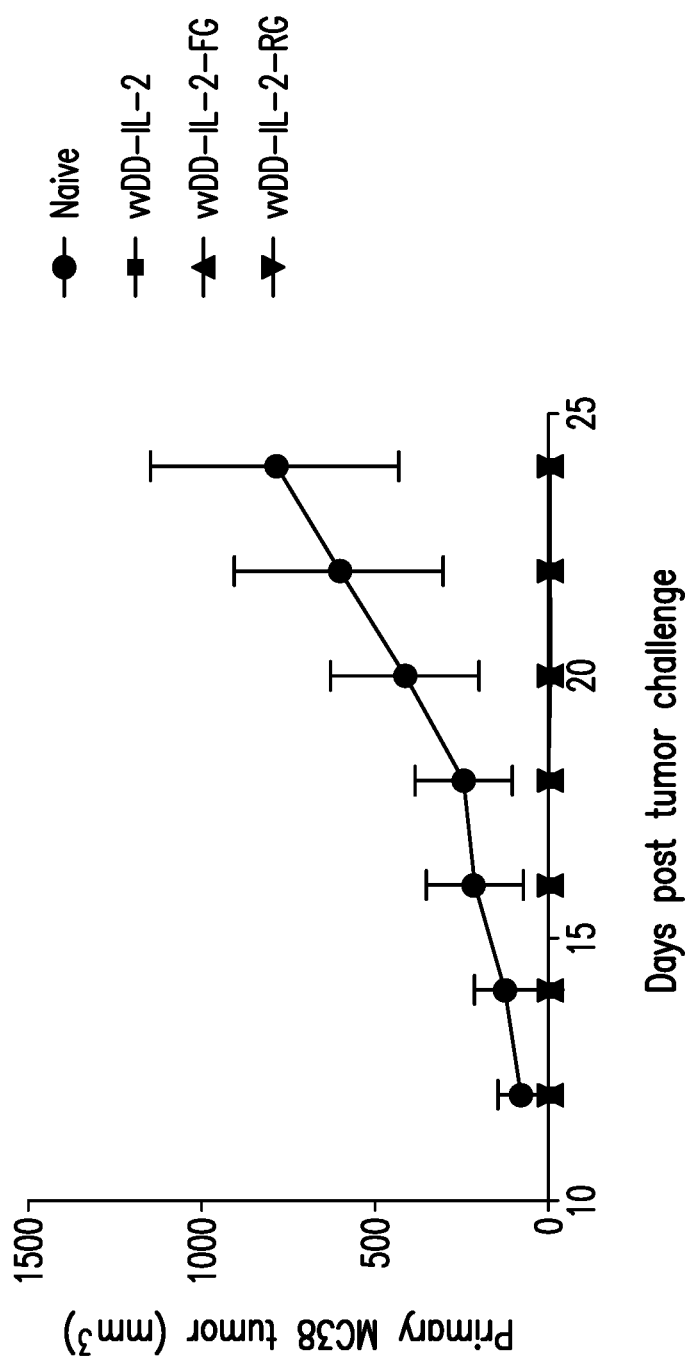

FIG. 13. Systemic antitumor immunity elicited by viral IL-2 variants. MC38-luc-tumor-bearing B6 mice treated with indicated vaccinia viruses, which survived more than 60 days, were subcutaneously rechallenged with $5\times10^5$MC38-luc cells per mouse. And naïve B6 mice received same dose tumor challenge as a control. The growth curves of primary tumors were shown.

FIG. 14A-H. The more immunosuppressive microenvironment in 9-day-tumor-bearing mice. B6 mice were intraperitoneally inoculated with $5\times10^5$MC38-luc cells and tumor tissues were harvested 5 days or 9 days post tumor inoculation. Primary tumors were photoed (A), weighed (B), and lysed to make single cells and stained to determine the presence of $CD4^+Foxp3^+$ (C), G-MDSC ($CD11b^+Ly6G^+Ly6C^{lo}$) (D), $CD4^+PD-1^+$ (E), $CD8^+PD-1^+$ (C), $CD3^-NK1.1^+$ (G), and $PD-L1^+$ (H) cells in the tumor microenvironment.

Figure 15A:
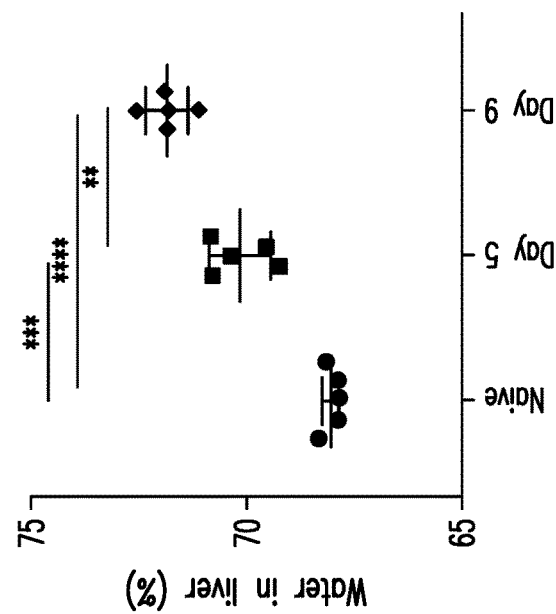
Figure 15B:
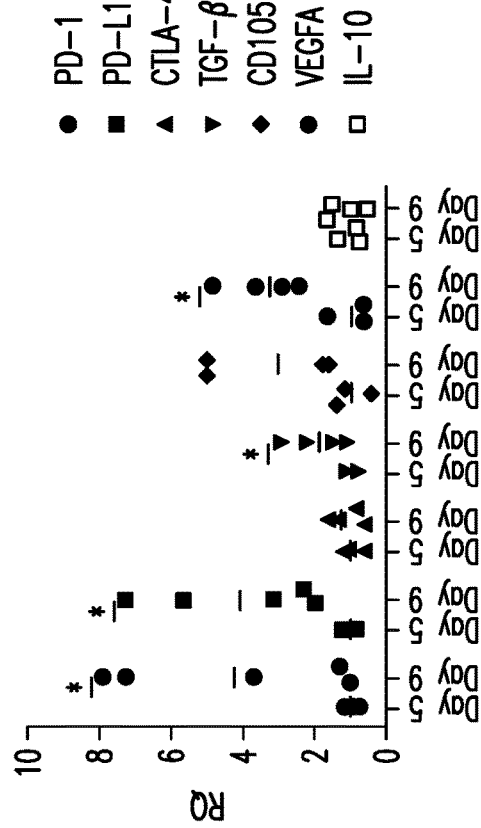
Figure 15C:
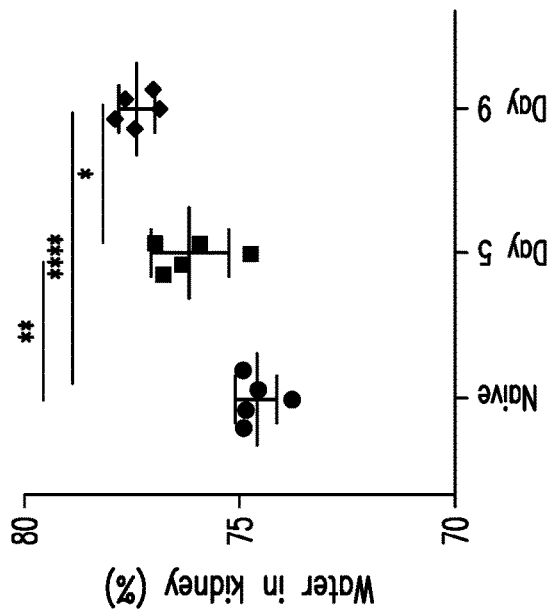
Figure 17A:
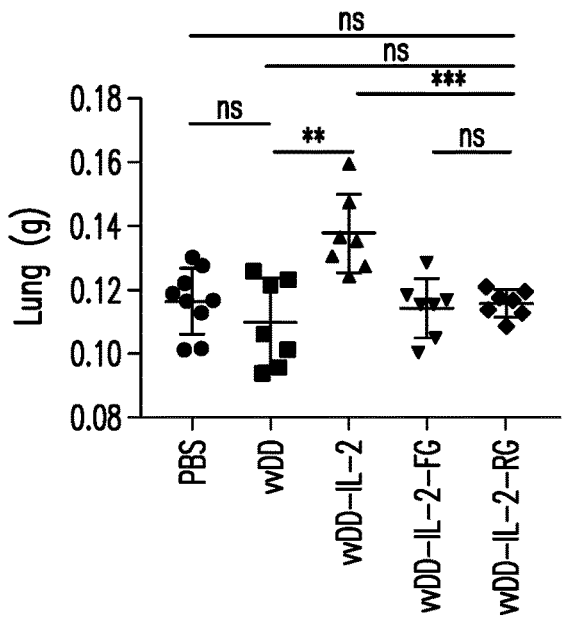
Figure 17B:
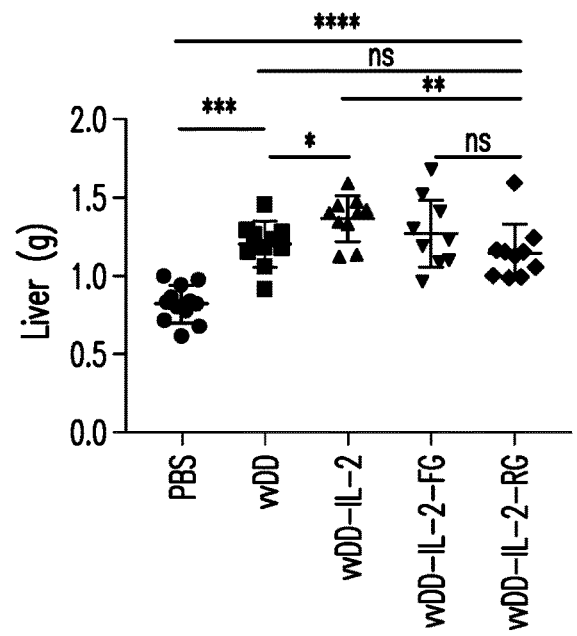
Figure 17C:
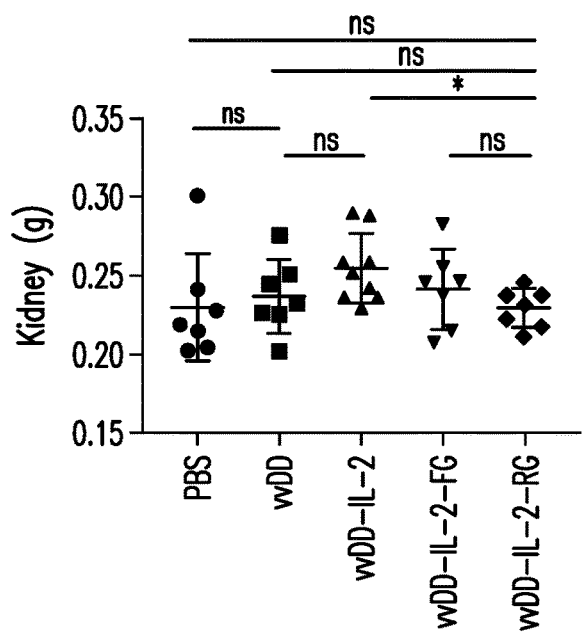
Figure 17D:
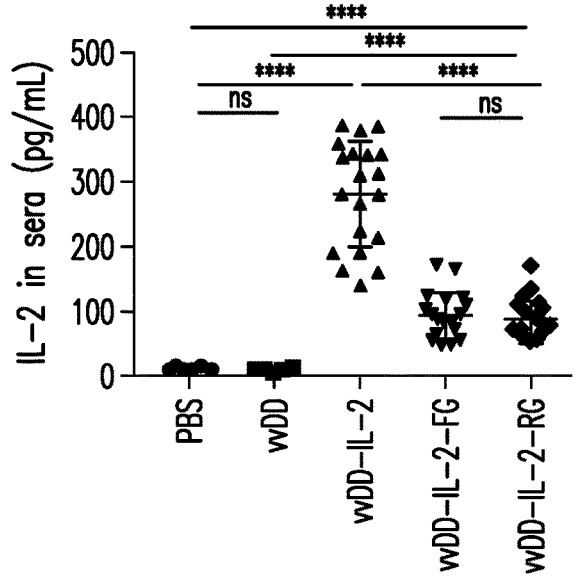

FIG. 15A-C. The elevated expression of immunosuppressive factors and edema in 9-day-tumor-bearing mice. B6 mice were intraperitoneally inoculated with $5\times10^5$ MC38-luc cells and mouse tissues were harvested 5 days or 9 days post tumor inoculation. (A) Primary tumors were applied to extract RNA for RT-qPCR to determine the expression of immunosuppressive factors. Livers and kidneys were harvested, weighed and dried to measure water content to determine liver edema (B) and lung edema (C).

FIG. 16A-E. Toxicity profile of viral delivered IL-2. B6 mice were intraperitoneally inoculated with $5\times10^5$MC38-luc cells and treated with PBS, vvDD, vvDD-IL-2, vvDD-IL-2-FG and vvDD-IL-2-RG at $2\times10^8$ PFU/mouse 9 days post tumor inoculation. The mice died earlier than PBS-treated mice, generally within 7 days post viral treatment, were counted as IL-2-induced death. The treatment related mortality was shown in (A). The treated mice were sacrificed 4 to 5 days post treatment for collecting blood to measure IL-2 (B) and TNF-α (C) in sera, and for monitoring lung edema (D) and liver edema (E). The standard symbols for P values are, * P<0.05;  P<0.01; * P<0.001; and **** P<0.0001.

FIG. 17A-D. The toxicity profile of vaccinia virus delivered IL-2 in early-stage-tumor-model. B6 mice were intraperitoneally inoculated with $5\times10^5$ MC38-luc cells and treated with vvDD, vvDD-IL-2, vvDD-IL-2-FG, vvDD-IL-2-RG, or PBS 5 days post tumor inoculation. The treated mice were sacrificed 8 days post treatment to harvest tissues to measure water content to determine edema in lung (A), liver (B) and kidney (C), or to harvest blood to measure IL-2 (D) in sera.

Figure 18M:
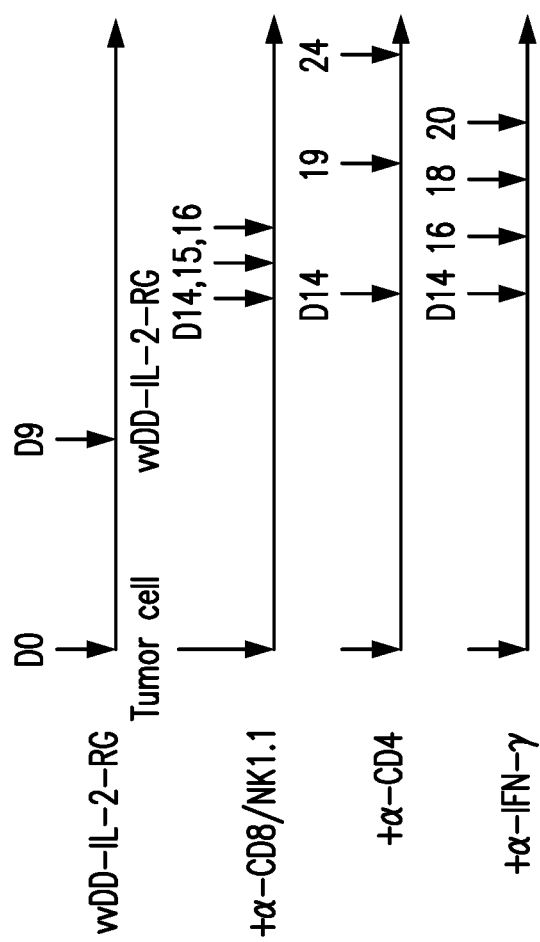
Figure 18N:
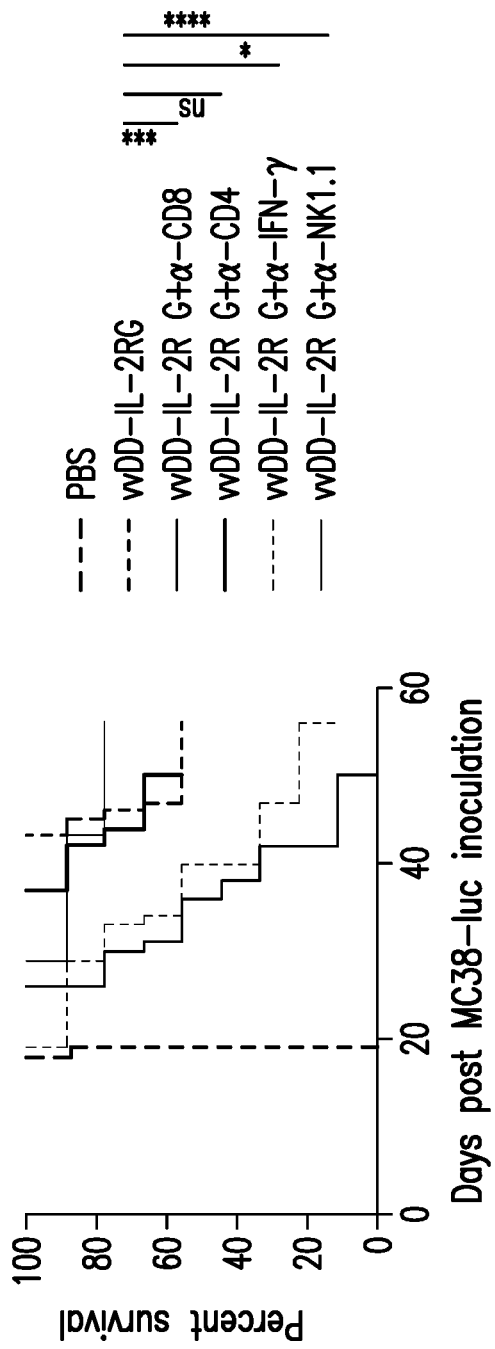

FIG. 18A-N. Immune status change in tumor microenvironment post virus treatments. B6 mice were intraperitoneally inoculated with $5\times10^5$MC38-luc cells and treated with PBS, vvDD, vvDD-IL-2-FG and vvDD-IL-2-RG at $2\times10^8$PFU/mouse 9 days post tumor inoculation. Tumor-bearing mice were sacrificed 5 days post treatment and primary tumors were collected and analyzed by flow cytometry to determine $CD4^+Foxp3^-$ and $CD8^+IFN-\gamma^+$ T cells (A, B), memory-phenotype T cells ($CD8^+CD44^{hi}$) (C), Regulatory T cells ($CD4^+Foxp3^+$) (D), CD8/Treg (E), or by RT-qPCR to determine IFN-γ, Granzyme B, Perforin, TGF-β, CD105, VEGF and IL-10 (F-I). In a separate experiment, B6 mice were inoculated with $5 \times 10^5$ MC38-luc cells i.p. and treated with vvDD-IL-2-RG or PBS 9 days post tumor inoculation. α-CD8 Ab (250 μg/injection), α-NK1.1 Ab (300 μg/injection), α-CD4 Ab (150 μg/injection), or α-IFN-γ Ab (200 μg/injection) were intraperitoneally injected into mice to deplete CD8$^+$ T cells, NK1.1$^+$ cells, CD4$^+$ T cells or neutralize circulating IFN-γ as scheduled (M), and the overall survival was shown by Kaplan-Meier analysis (N).

FIG. 19A-D. The memory-phenotype CD8$^+$ T cells and NK cells in 9-day-tumor-bearing mice. B6 mice were intraperitoneally inoculated with $5 \times 10^5$ MC38-luc cells and treated as described in FIG. 18. Primary tumors and spleens were harvested 5 days post viral treatment and applied to make single cells and stained to determine CD8$^+$ CD44$^{hi}$ in spleen (A), CD3$^-$NK1.1$^+$ in tumor (B) and spleen (C), CD8$^+$ T cells in tumor (D).

Figure 20:
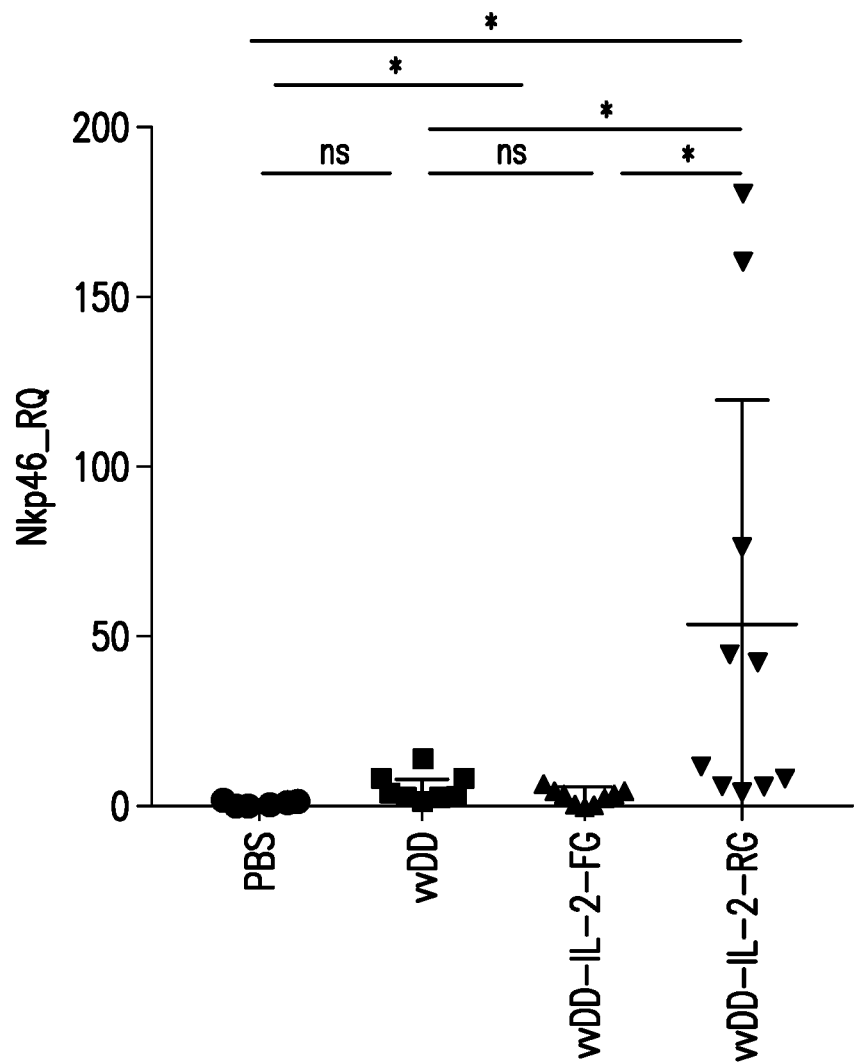

FIG. 20. The elevated NKP46 expression in 9-day-tumor-bearing mice post viral treatment. B6 mice were intraperitoneally inoculated with $5 \times 10^5$ MC38-luc cells and treated as described in FIG. 18. Primary tumors were harvested and applied to extract RNA for RT-qPCR to determine the expression of NKP46.

Figure 21B:
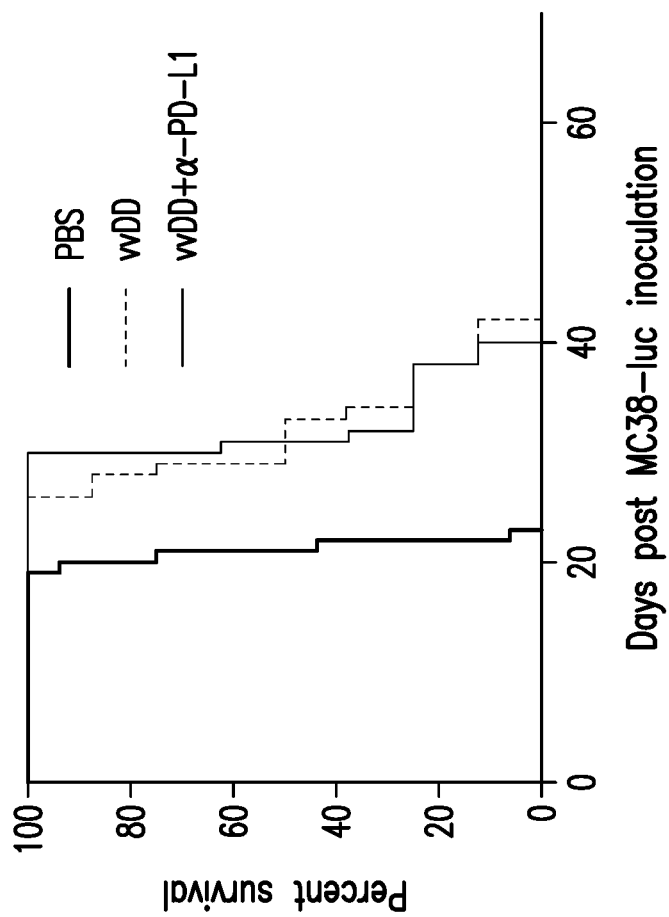
Figure 21A:
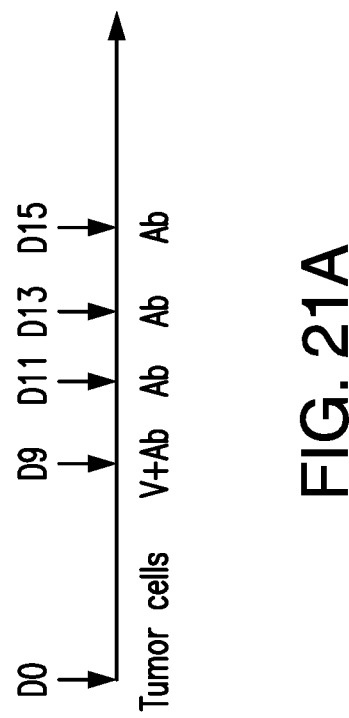

FIG. 21A-B. The antitumor efficacy of vvDD combined with PD-L1 blockade. B6 mice were intraperitoneally inoculated with $5 \times 10^5$ MC38-luc cells and treated as scheduled (A), and the overall survival was shown by Kaplan-Meier analysis (B).

FIG. 22A-E. Viral treatment apt to the combination with immune checkpoint therapy. B6 mice were inoculated with $5 \times 10^5$ MC38-luc cells and treated as described in FIG. 18. Tumor-bearing mice were sacrificed 5 days post treatment and primary tumors were collected and analyzed by RT-qPCR to determine the expression of PD-1, PD-L1, and CTLA-4 (A-C). In a separate experiment, B6 mice were intraperitoneally inoculated with $5 \times 10^5$ MC38-luc cells and treated with vvDD-IL-2-RG or PBS 9 days post tumor inoculation. α-PD-1 Ab (200 μg/injection), α-PD-L1 Ab (200 μg/injection), or α-CTLA-4 Ab (100 μg/injection) were intraperitoneally injected into mice as scheduled (D), and the overall survival was shown by Kaplan-Meier analysis (E).

Figure 23A:
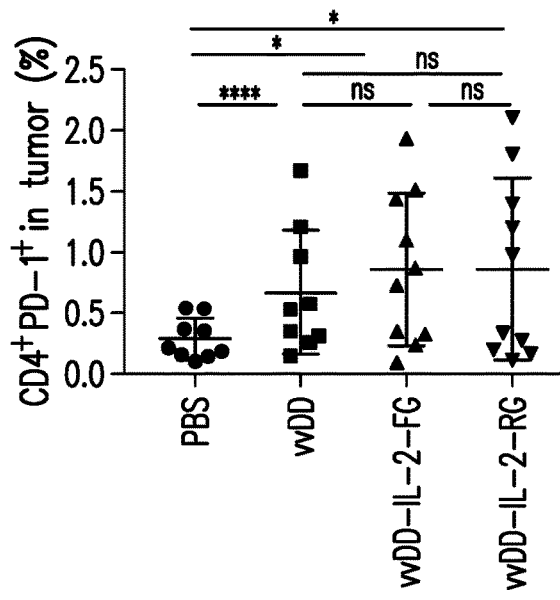
Figure 23B:
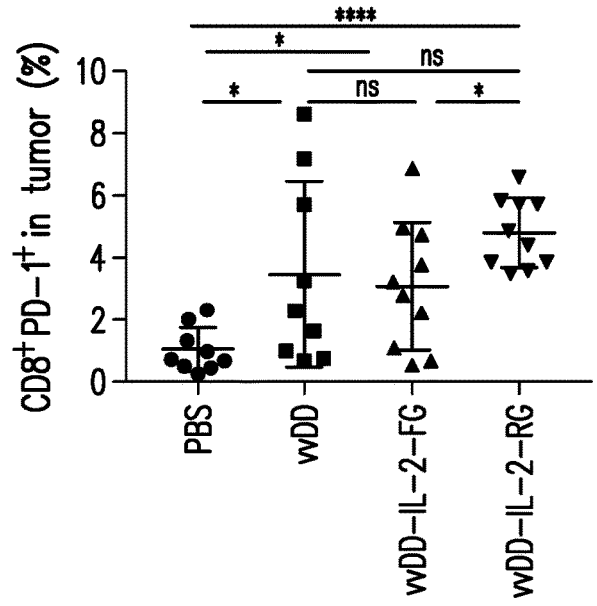
Figure 23C:
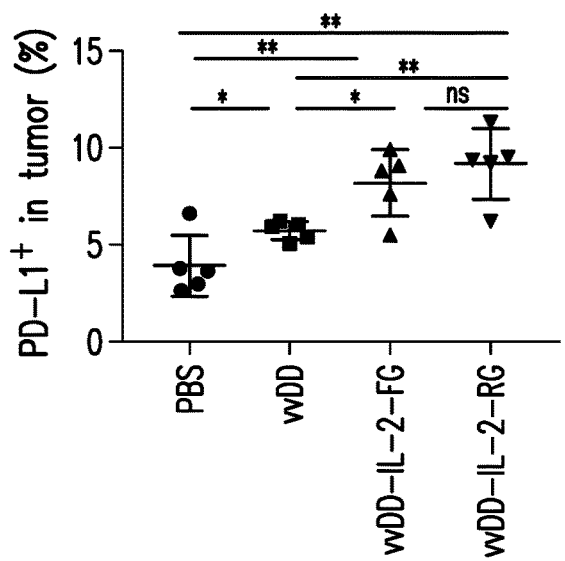

FIG. 23A-C. The elevated exhausted T cells and PD-L1$^+$ cells in 9-day-tumor-bearing mice post viral treatment. B6 mice were intraperitoneally inoculated with $5 \times 10^5$ MC38-luc cells and treated as described in FIG. 18. Primary tumors were harvested and applied to make single cells and stained to determine CD4$^+$PD-1$^+$ (A) and CD8$^+$PD-1+(B) T cells, and PD-L1+ cells (C).

Figure 24A:
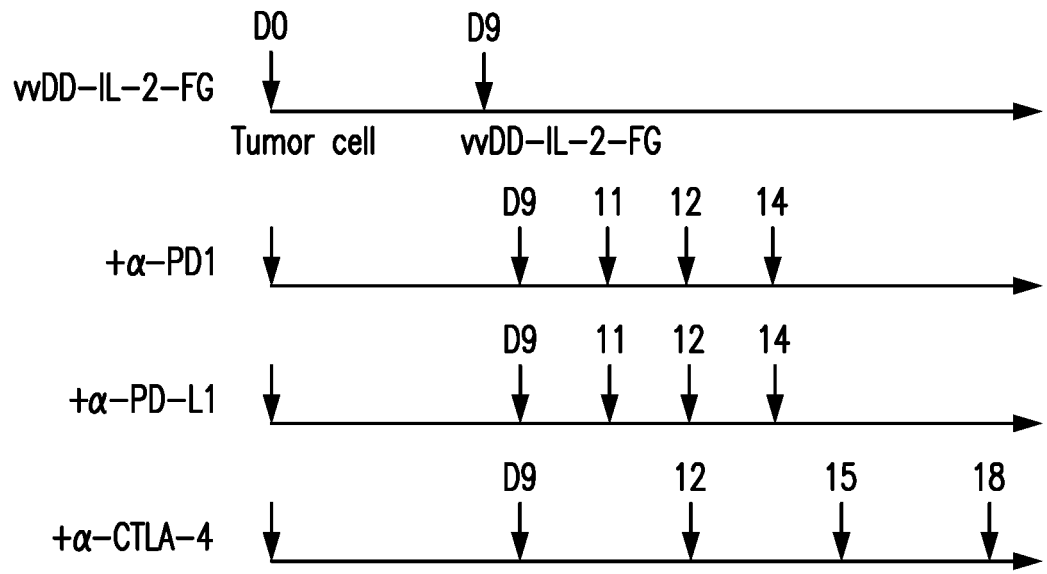
Figure 24B:
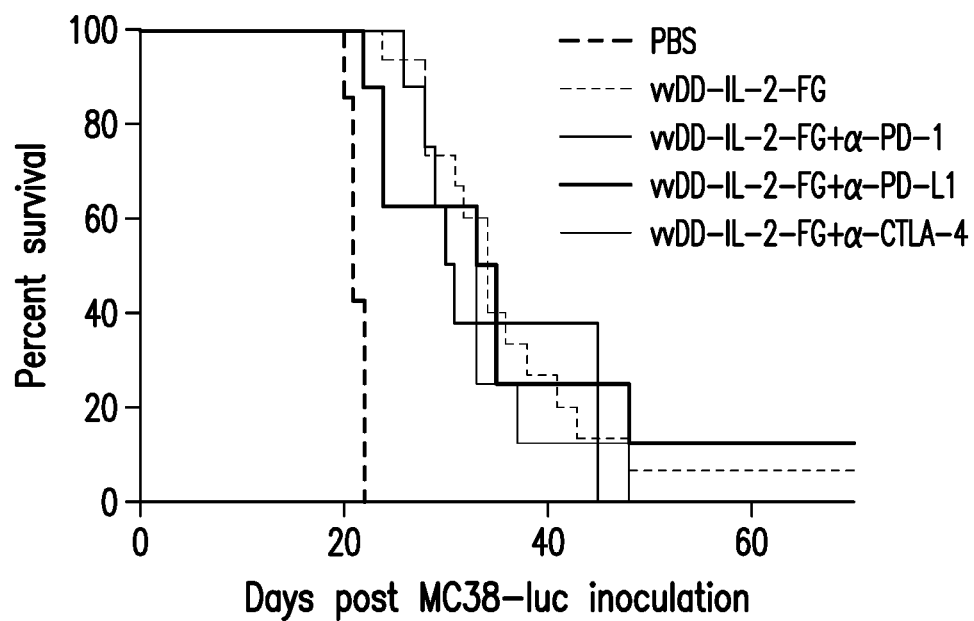

FIG. 24A-B. The antitumor efficacy of vvDD-IL-2-FG combined immune checkpoint therapy. B6 mice were intraperitoneally inoculated with $5 \times 10^5$ MC38-luc cells and treated with vvDD-IL-2-FG or PBS 9 days post tumor inoculation. α-PD-1 Ab (200 μg/injection), α-PD-L1 Ab (200 μg/injection), or α-CTLA-4 Ab (100 μg/injection) were intraperitoneally injected into mice as scheduled (A), and the overall survival was shown by Kaplan-Meier analysis (B).

FIG. 25A-C. CD8$^+$ T cell response in the tumor microenvironment (TME) of MC38 s.c. tumors 10 days post virus treatment. (A) Experimental setup: B6 mice were s.c. inoculated with $5 \times 10^5$ MC38 cancer cells. When the tumor area reached $5 \times 5$ mm$^2$ vvDD, vvDD-IL-2, vvDD-IL-15, vvDD-CXC11, vvDD-CCL5 ($1 \times 10^8$ pfu per tumor) or PBS was intratumorally injected (n=4-5 per group). 10 days later tumors have been collected and proceed to single cell suspension followed by magnetic separation (CD8 negative selection) for IFN-γ ELISPOT. (B) CD8$^+$ T cells have been analyzed for IFN-γ production by ELISPOT. CD8$^+$ T cells ($2 \times 10^4$ per well) were either left unstimulated (control) or challenged with γ-irradiated MC38 tumor cells ($2 \times 10^4$ per well) for 24 h. Results are shown as individual data points (number of spots in each well) and bars (means±standard deviation) of CD8$^+$ T cells from each mouse evaluated in triplicates. To determine MC38 reactive responses the average value of spots from control wells were subtracted from the number of spots in MC38 challenged wells. Data were presented as individuals and means. Student's t-test was used to analyze the statistical significance (*p<0.05). (C) The virus induced CD8$^+$ T cells in the TME are tumor specific. B6 mice were s.c. inoculated with $5 \times 10^5$ MC38 cancer cells. When the tumor area reached $5 \times 5$ mm$^2$ vvDD, vvDD-IL-2 ($1 \times 10^8$ pfu per tumor) or PBS was intratumorally injected (n=7 per group, Data are presented as summary of two independent experiments). 10 days later tumors have been collected and proceed to single cell suspension followed by magnetic separation (CD8 negative selection). CD8$^+$ T cells have been analyzed for IFN-γ production by ELISPOT. CD8$^+$ T cells ($2 \times 10^4$ per well) were either left unstimulated (medium control) or challenged with γ-irradiated MC38 tumor cells ($2 \times 10^4$ per well) or irrelevant target cells as γ-irradiated B16 tumor cells ($2 \times 10^4$ per well) or naïve splenocytes ($2 \times 10^4$ per well) from non-tumor-bearing B6 mouse for 24 h. Results are shown as individual data points (number of spots in each well) and bars (means±standard deviation) of CD8+ T cells from each mouse evaluated in duplicate. Student's t-test was used to analyze the statistical significance (*p<0.05).

Figure 26A:
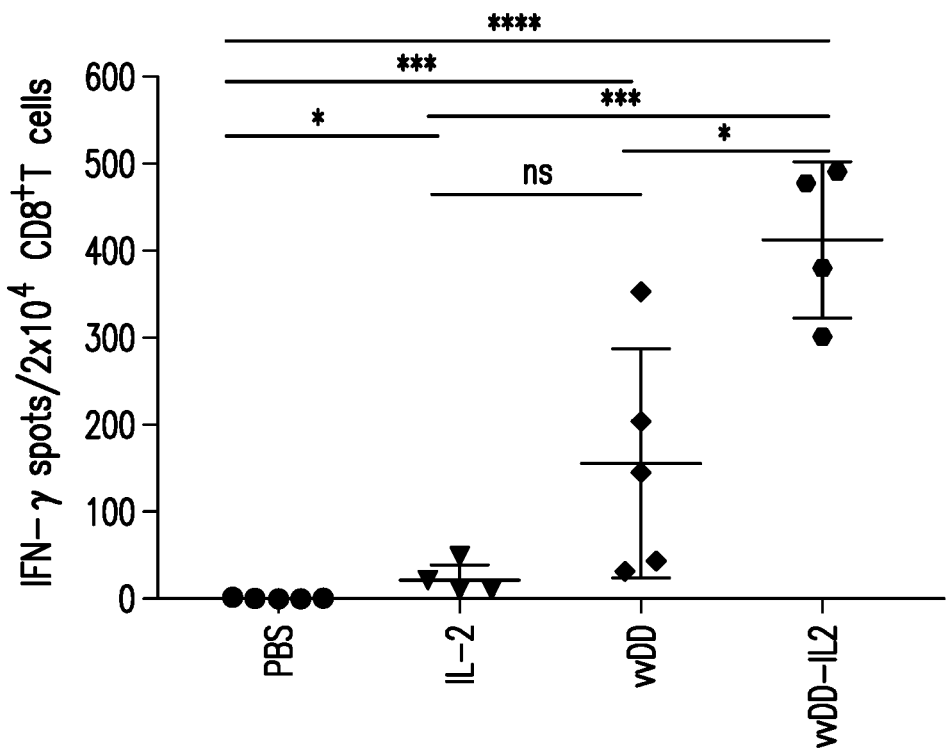
Figure 26B:
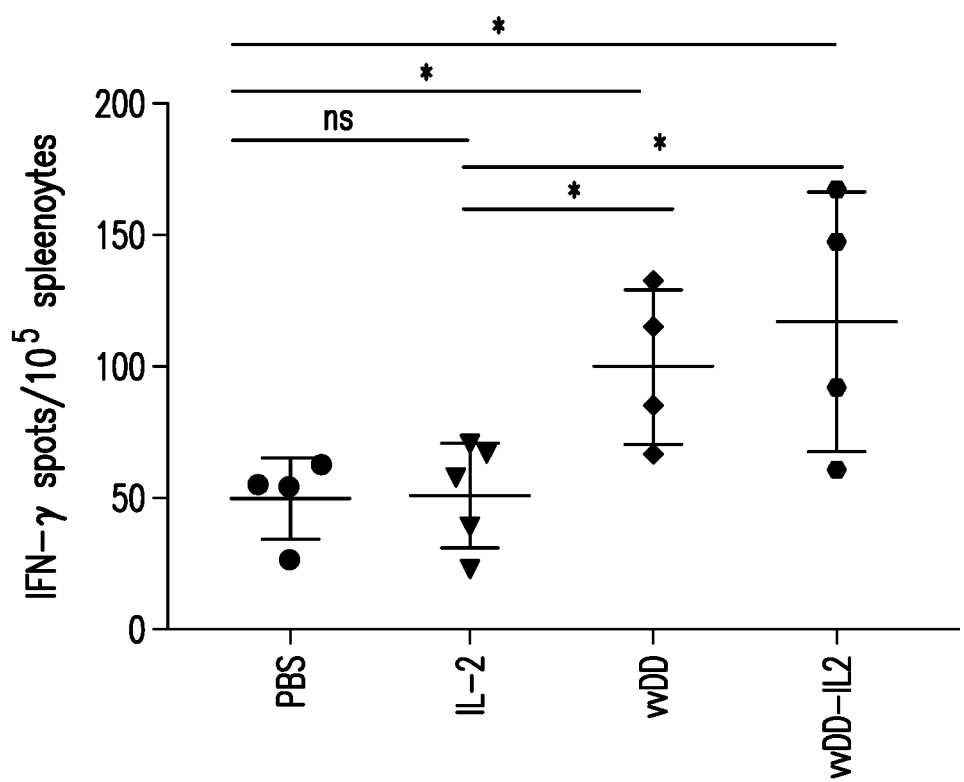

FIG. 26A-B. CD8$^+$ T cell response in the TME of MC38 s.c. tumors induced by vvDD-IL-2 is superior to IL-2 treatment. B6 mice were s.c. inoculated with $5 \times 10^5$ MC38 cancer cells. When the tumor area reached $5 \times 5$ mm$^2$ IL-2 ($1 \times 10^6$ IU per tumor), vvDD, vvDD-IL-2 ($1 \times 10^8$ pfu per tumor) or PBS was intratumorally injected (n=4-5 per group). 10 days later tumors have been collected and proceed to single cell suspension followed by magnetic separation (CD8 negative selection). (A) To determine the local immune response CD8$^+$ T cells have been analyzed for IFN-γ production by ELISPOT. CD8$^+$ T cells ($2 \times 10^4$ per well) were either left unstimulated (control) or challenged with γ-irradiated MC38 tumor cells ($2 \times 10^4$ per well) for 24 h. Results are shown as individual data points (number of spots in each well) and bars (means±standard deviation) of CD8$^+$ T cells from each mouse evaluated in triplicates. To determine tumor reactive responses the average value of spots from control wells were subtracted from the number of spots in MC38 challenged wells. Student's t-test was used to analyze the statistical significance (*p<0.05). (B) For analysis of the systemic immune response additionally the spleen from each mouse has been harvested and proceeded to single cell suspension. Splenocytes have been analyzed for IFN-γ production by ELISPOT. Splenocytes ($1 \times 10^5$ per well) were either left unstimulated (control) or challenged with γ-irradiated MC38 tumor cells ($2 \times 10^4$ per well) for 24 h. Results are shown as individual data points (number of spots in each well) and bars (means±standard deviation) of splenocytes from each mouse evaluated in triplicates. To determine tumor reactive responses the average value of spots from control wells were subtracted from the number of spots in MC38 challenged wells. Student's t-test was used to analyze the statistical significance (*p<0.05).

FIG. 27A-B. vvDD-IL-2 and vvDD treatment increase the number of tumor infiltrating T cells. (A) B6 mice were s.c. inoculated with $5 \times 10^5$ MC38 cancer cells. When the tumor area reached $5 \times 5$ mm$^2$ PBS or vvDD, vvDD-IL-2 ($1 \times 10^8$ pfu per tumor) was intratumorally injected (n=5 per group). 10 days later tumors have been collected, fixed and stained for DAPI, CD3, CD4, CD8. Representative immunofluorescence image of one sample from each group. (B) Summary of the percentage of CD3+ T cells and CD3+CD4+ and CD3+CD8+ T cells per area.

Figure 28:
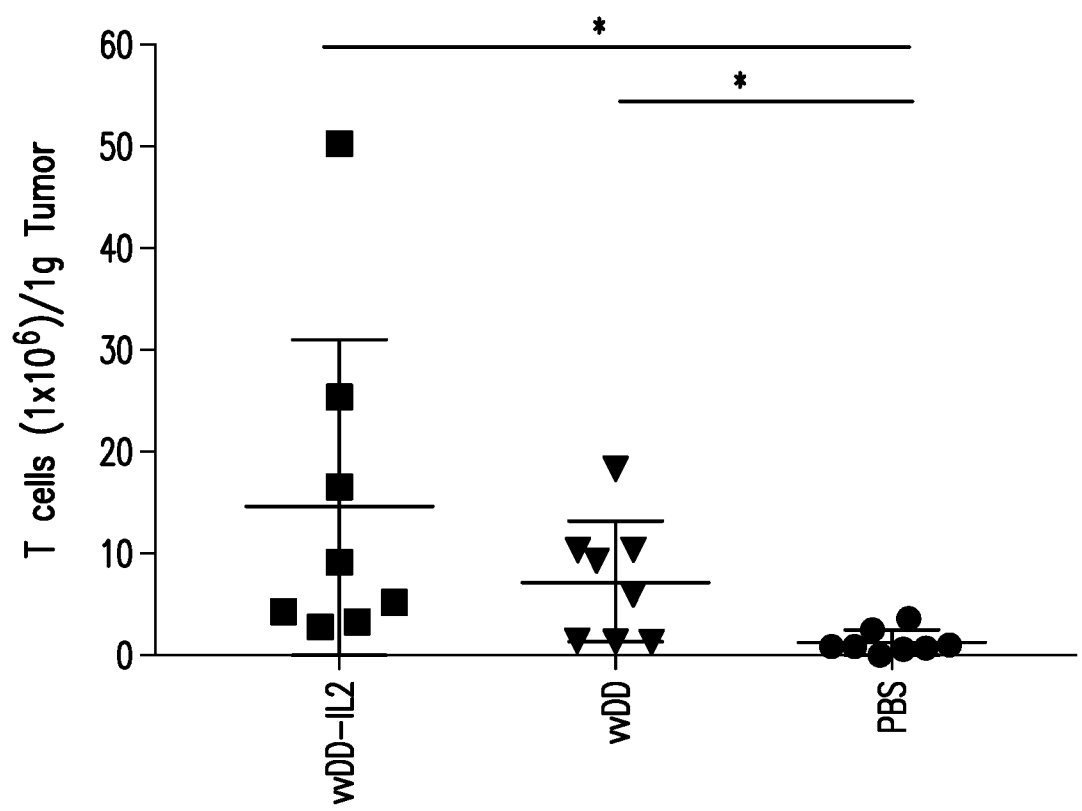

FIG. 28. vvDD-IL-2 and vvDD treatment increases the number of T cells in the tumor. B6 mice were s.c. inoculated with $5 \times 10^5$ MC38 cancer cells. When the tumor area reached $5 \times 5$ mm$^2$ vvDD, vvDD-IL-2 ($1 \times 10^8$ pfu per tumor) or PBS was intratumorally injected (n=8 per group). 10 days later tumors have been collected and proceed to single cell suspension followed by magnetic separation (CD90.2 beads). T cells from each individual mouse have been counted and calculated per gram tumor. Student's t-test was used to analyze the statistical significance (*p<0.05).

Figure 29B:
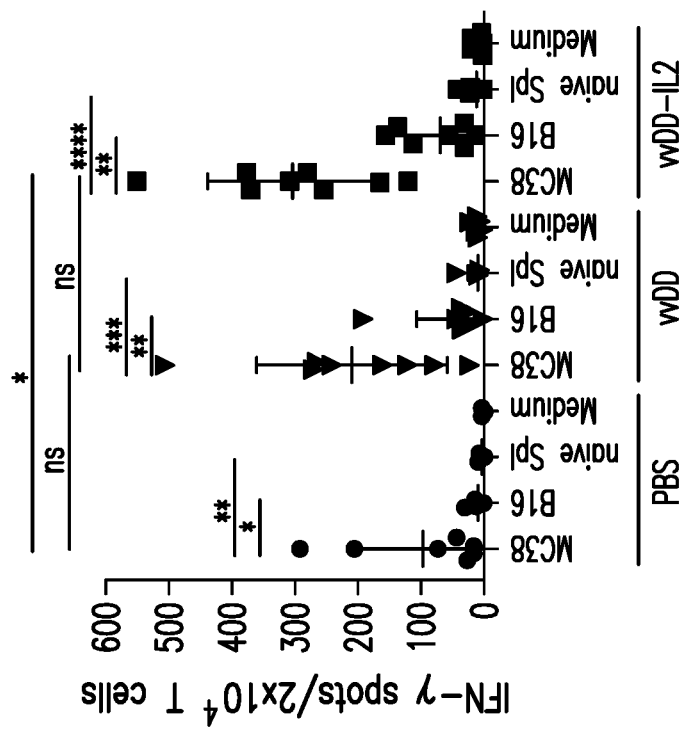
Figure 29A:
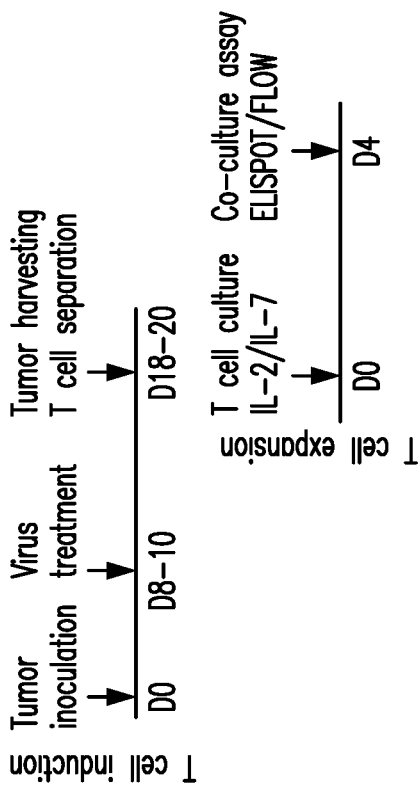
Figure 29C:
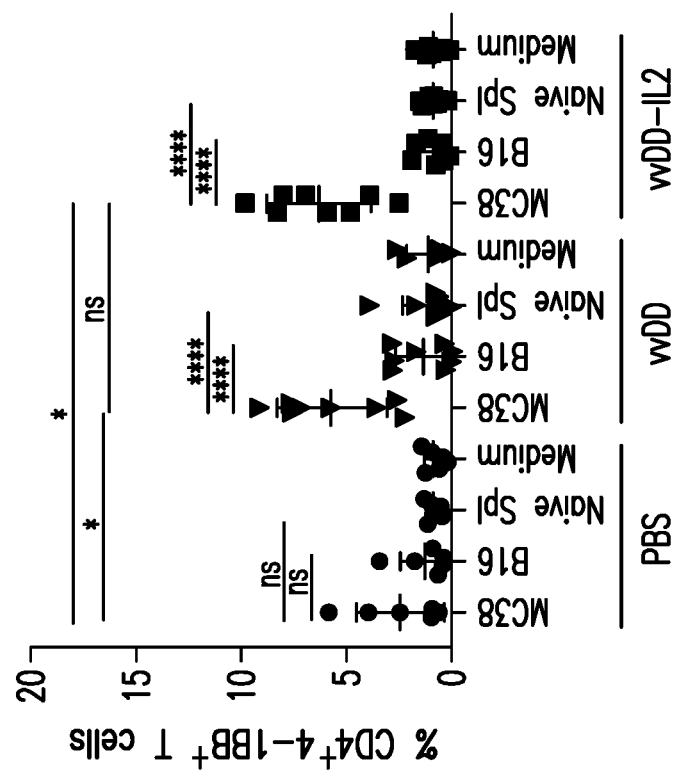
Figure 29C:
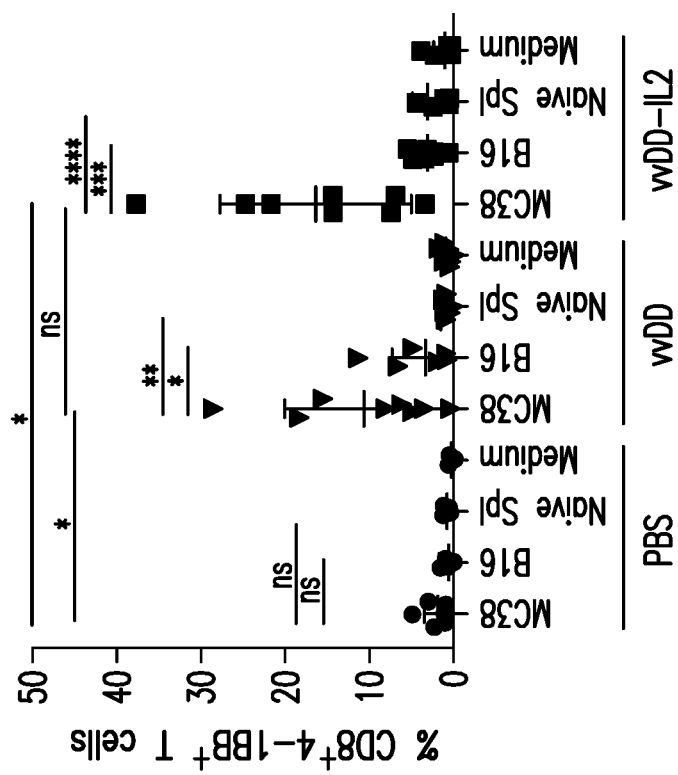

FIG. 29A-C. Tumor Infiltrated T Cells—Induced by Oncolytic Virus ("OV-induced T cells") can be cultured ex vivo and keep their tumor specificity. (A) Experimental setup: B6 mice were s.c. inoculated with $5 \times 10^5$ MC38 cancer cells. When the tumor area reached $5 \times 5$ mm$^2$ vvDD, vvDD-IL-2 ($1 \times 10^8$ pfu per tumor) or PBS was intratumorally injected (n=4 per group, Data are presented as summary of 2 independent experiments). 10 days later tumors have been collected and proceed to single cell suspension followed by magnetic separation (CD90.2 beads). T cells from each individual mouse have been cultured in 24-well plates ($1 \times 10^6$ per well) in RPMI complete media in the presence of IL-2 (30 IU/ml) and IL-7 (5 ng/ml). (B) To determine the tumor specificity of the T cells under culture conditions, T cells from each individual mouse have been tested after 4 days for IFN-γ production by ELISPOT. T cells ($2 \times 10^4$ per well) were either left unstimulated (medium) or challenged with γ-irradiated MC38 tumor cells ($2 \times 10^4$ per well) or irrelevant target cells as γ-irradiated B16 tumor cells ($2 \times 10^4$ per well) or naïve splenocytes ($2 \times 10^4$ per well) from non-tumor-bearing B6 mouse in duplicate for 24 h. Results are shown as individual data points (number of spots in each well) and bars (means±standard deviation) of T cells from each mouse evaluated in duplicate. Student's t-test was used to analyze the statistical significance (*p<0.05; p<0.01; *p<0.001; ****p<0.0001). (C) Besides IFN-γ ELISPOT the T cells have been tested for 4-1BB upregulation by flow cytometry. T cells ($2 \times 10^4$ per well) were either left unstimulated (medium control) or challenged with γ-irradiated MC38 tumor cells ($2 \times 10^4$ per well) or irrelevant target cells as γ-irradiated B16 tumor cells ($2 \times 10^4$ per well) or naïve splenocytes ($2 \times 10^4$ per well) from non-tumor-bearing B6 mouse in duplicate. After 24 h the cells have been stained for flow cytometry analysis against CD3, CD4, CD8, 4-1BB. Results are shown as individual data points (percentage of CD8$^+$4-1BB$^+$ T cells and CD4$^+$4-1BB$^+$ T cells) and bars (means±standard deviation) of T cells from each mouse evaluated in duplicate. Student's t-test was used to analyze the statistical significance (*p<0.05; p<0.01; *p<0.001; ****p<0.0001).

Figure 30:
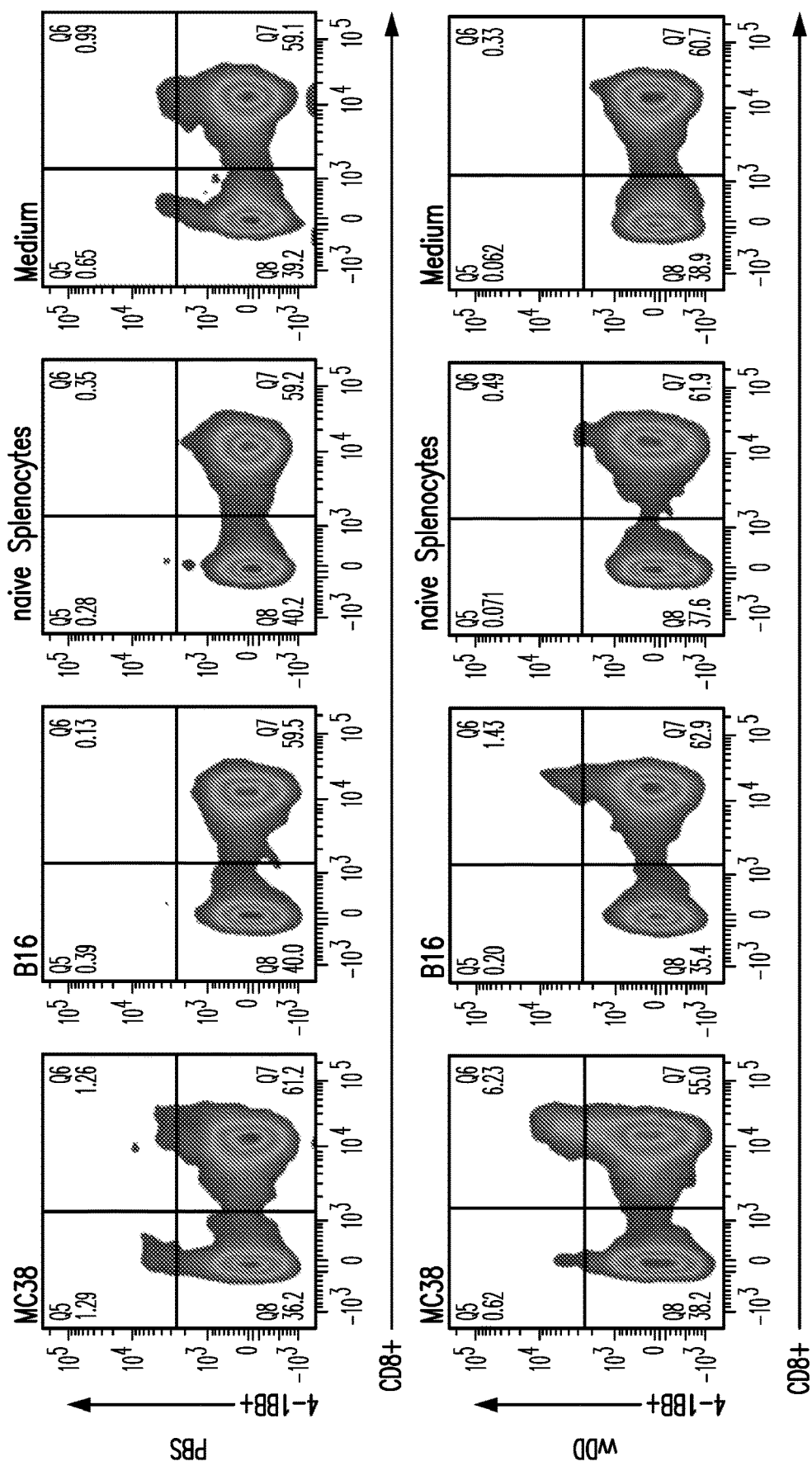
Figure 30:
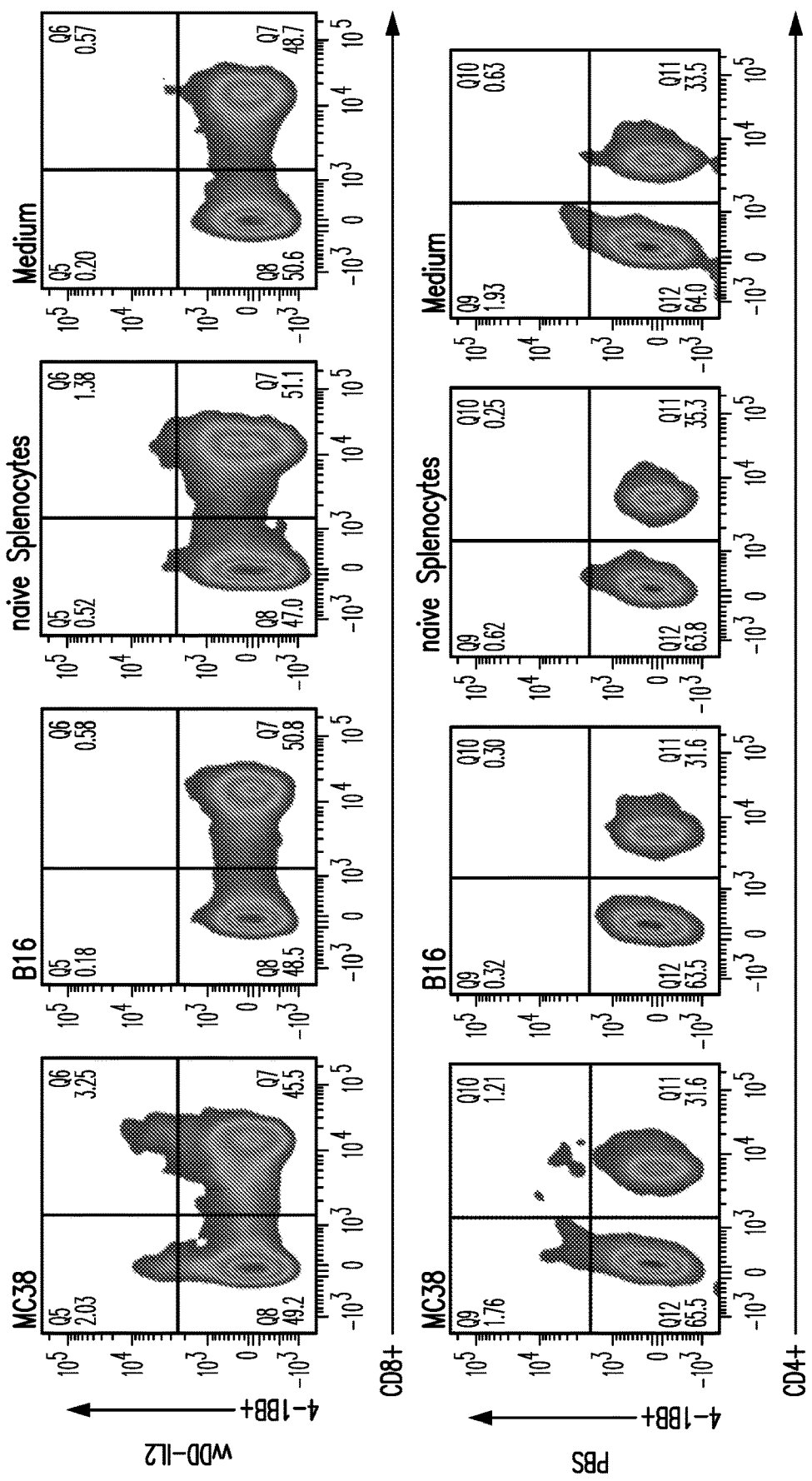
Figure 30:
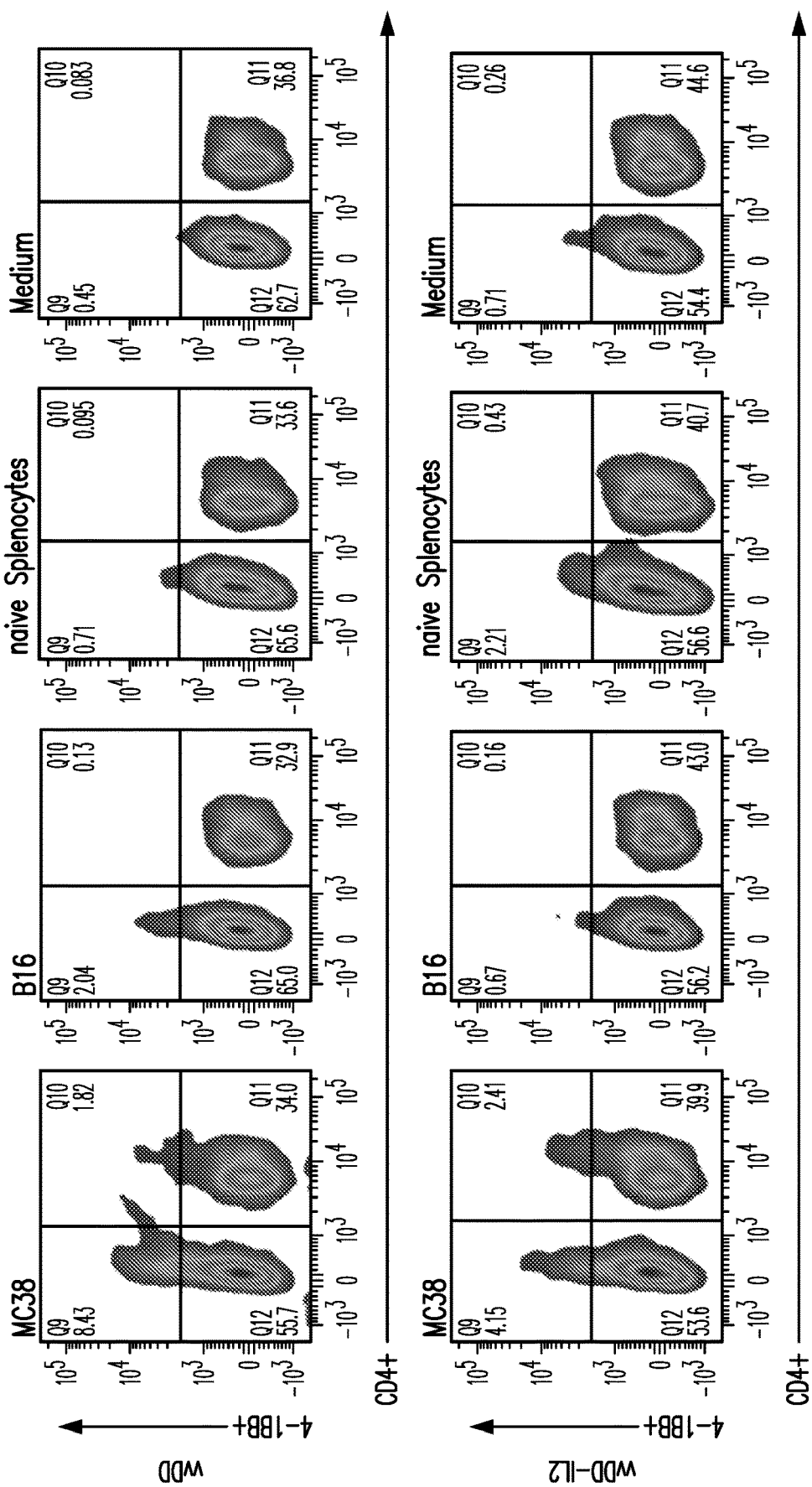

FIG. 30. Representative flow cytometry plot of CD8$^+$4-1BB$^+$ and CD4$^+$4-1BB$^+$ T cells of one sample from each group.

Figure 31C:
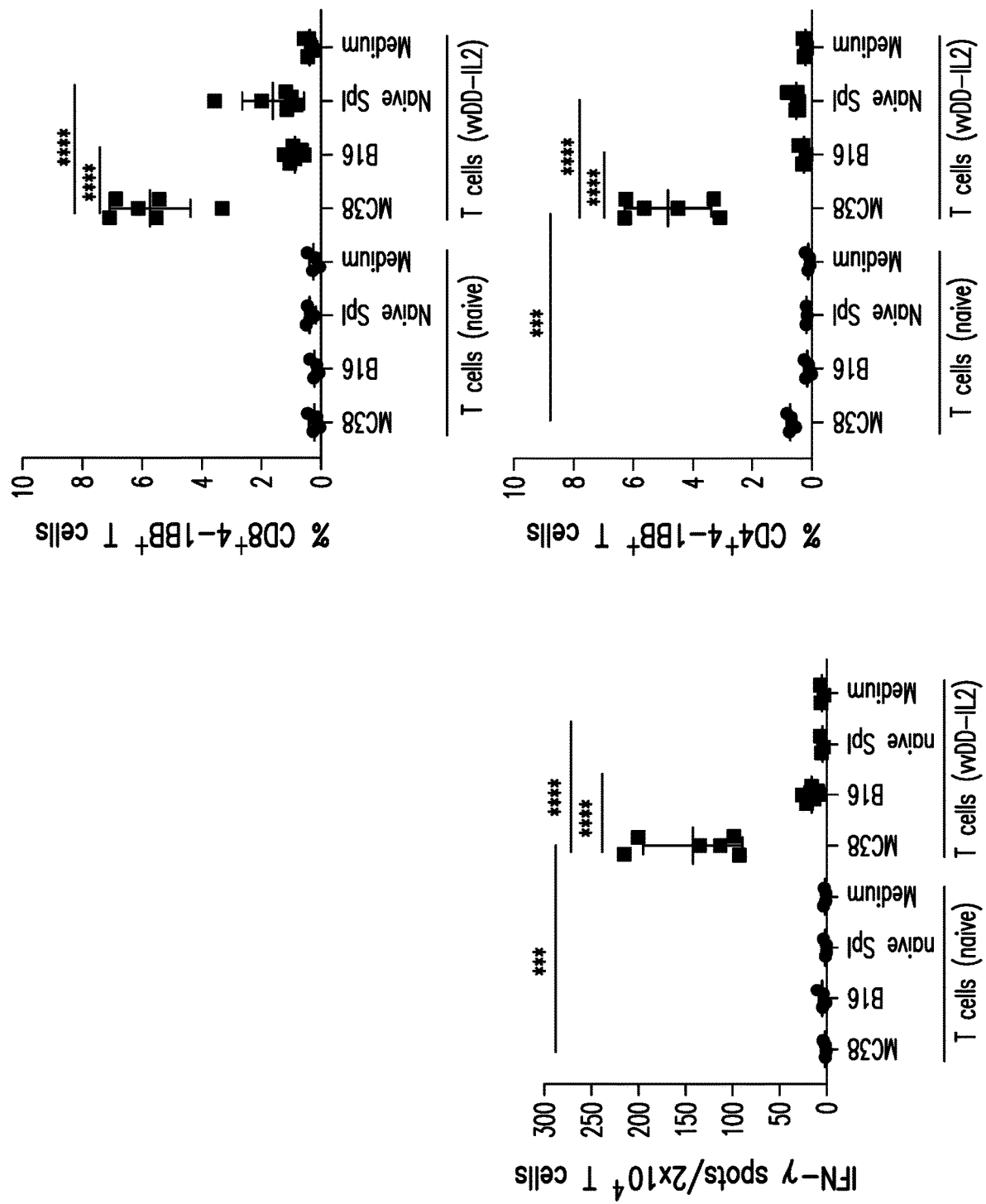

FIG. 31A-C. In vitro analysis of the vvDD-IL-2 induced T cells versus naïve T cells prior to adoptive T cell transfer. Prior to ACT the cultured T cells have been tested for tumor reactivity in vitro using IFN-γ ELISPOT and co-culture assay for flow cytometry staining of 4-1BB expression and IFN-γ ELISA. For ELISPOT and the co-culture assay T cells ($2 \times 10^4$ per well) were either left unstimulated (medium) or challenged with γ-irradiated MC38 tumor cells ($2 \times 10^4$ per well) or irrelevant target cells as γ-irradiated B16 tumor cells ($2 \times 10^4$ per well) or naïve splenocytes ($2 \times 10^4$ per well) from non-tumor-bearing B6 mouse in duplicate for 24 h. (A) ELISPOT Results are shown as individual data points (number of spots in each well) and bars (means ±standard deviation) of T cells from each mouse evaluated in in duplicate. (B and C) Besides IFN-γ ELISPOT the T cells have been tested for 4-1BB Expression by flow cytometry. The cells ($2 \times 10^4$ per well) were either left unstimulated (medium control) or challenged with γ-irradiated MC38 tumor cells ($2 \times 10^4$ per well) or irrelevant target cells as γ-irradiated B16 tumor cells ($2 \times 10^4$ per well) or naïve splenocytes ($2 \times 10^4$ per well) from non-tumor-bearing B6 mouse in duplicate. After 24 h the cells have been stained for FLOW analysis against CD3, CD4, CD8, 4-1BB. Results are shown as individual data points (percentage of CD8$^+$4-1BB$^+$ T cells and CD4$^+$4-1BB$^+$ T cells) and bars (means±standard deviation) of T cells from each mouse evaluated in duplicate. Student's t-test was used to analyze the statistical significance (*p<0.05; p<0.01; *p<0.001; ****p<0.0001).

Figure 32:
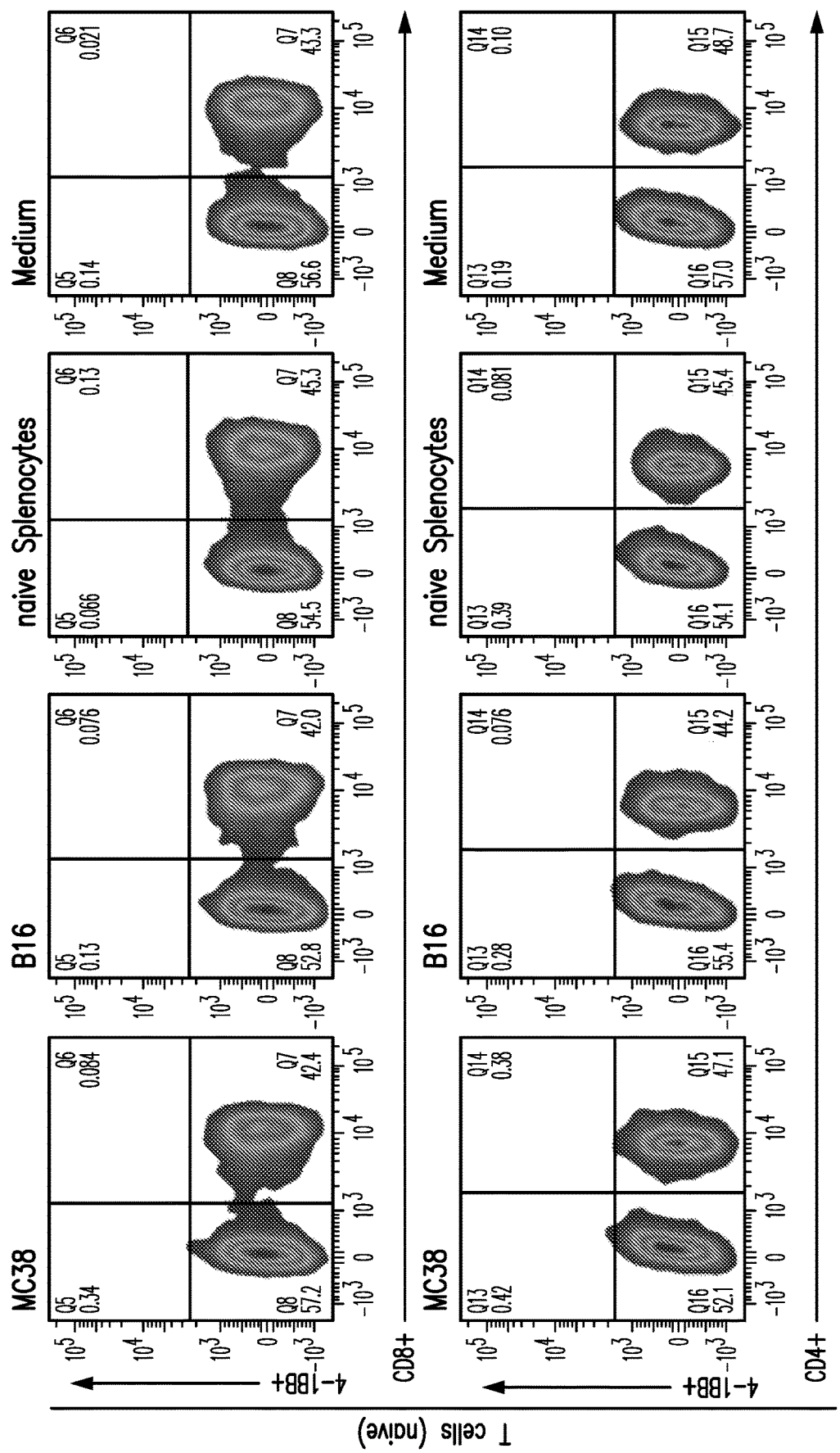
Figure 32:
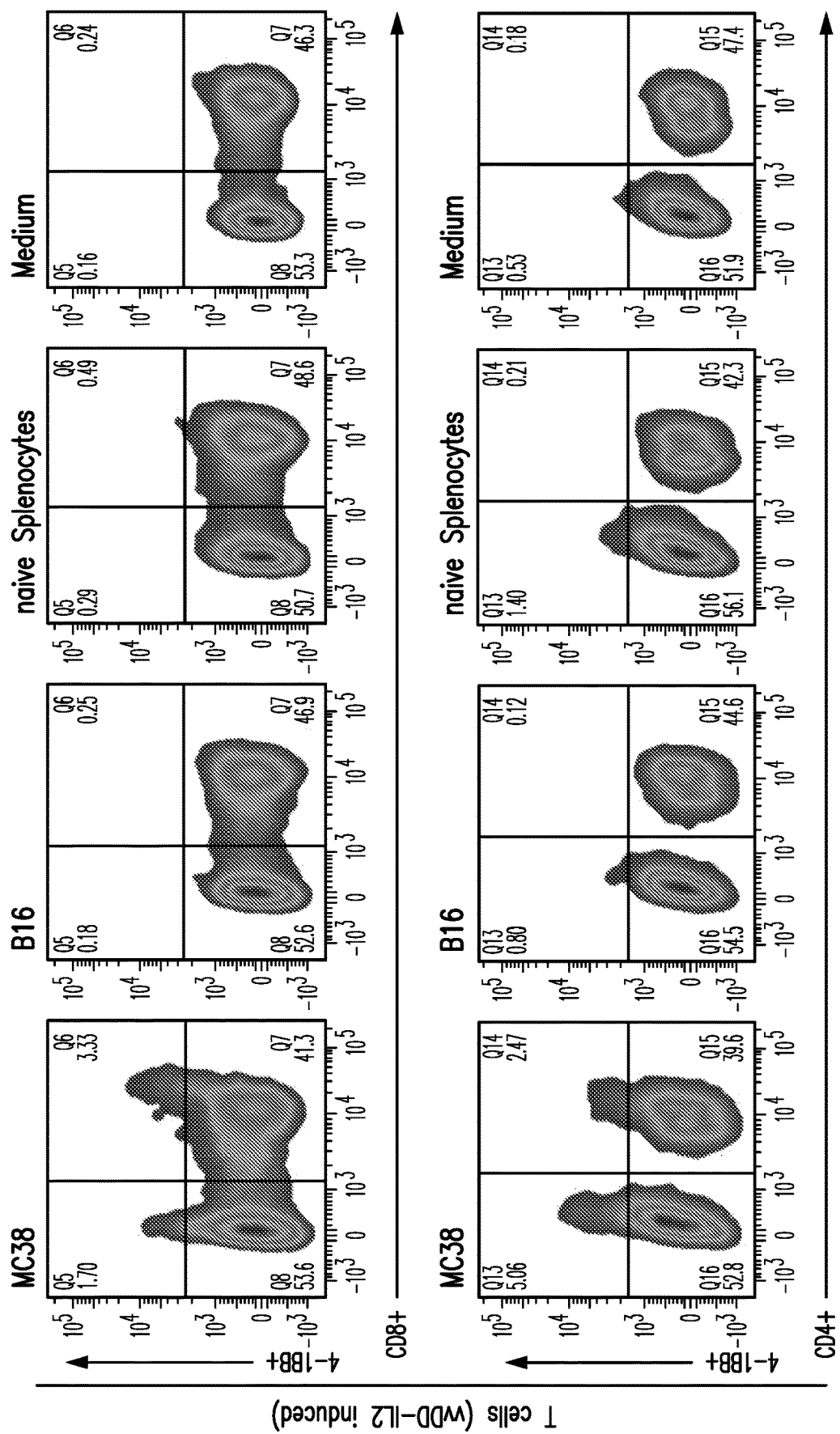

FIG. 32. Representative flow cytometry plot of CD8$^+$4-1BB$^+$ and CD4$^+$4-1BB$^+$ T cells of one sample from each group.

Figure 33B:
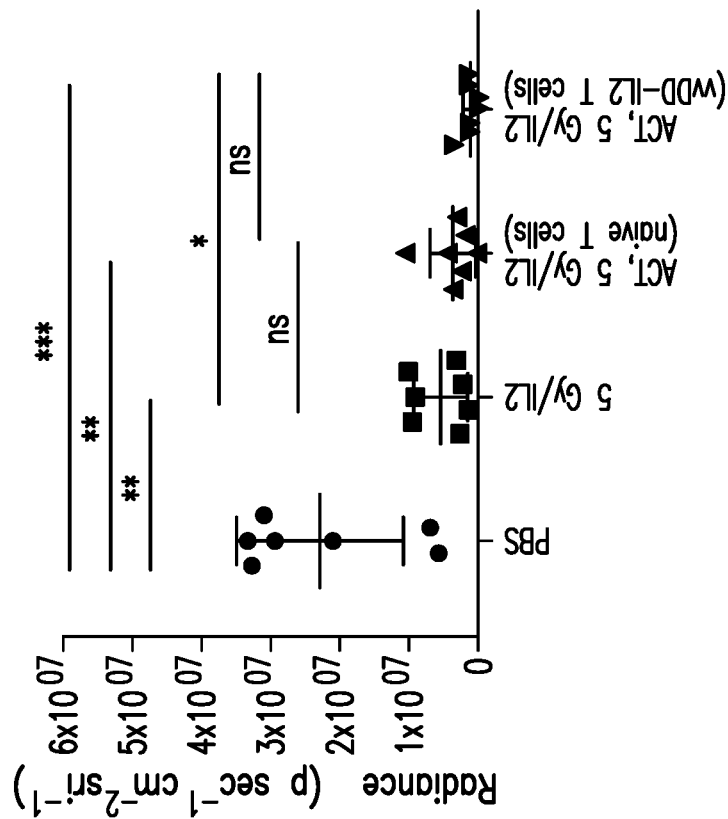
Figure 33A:
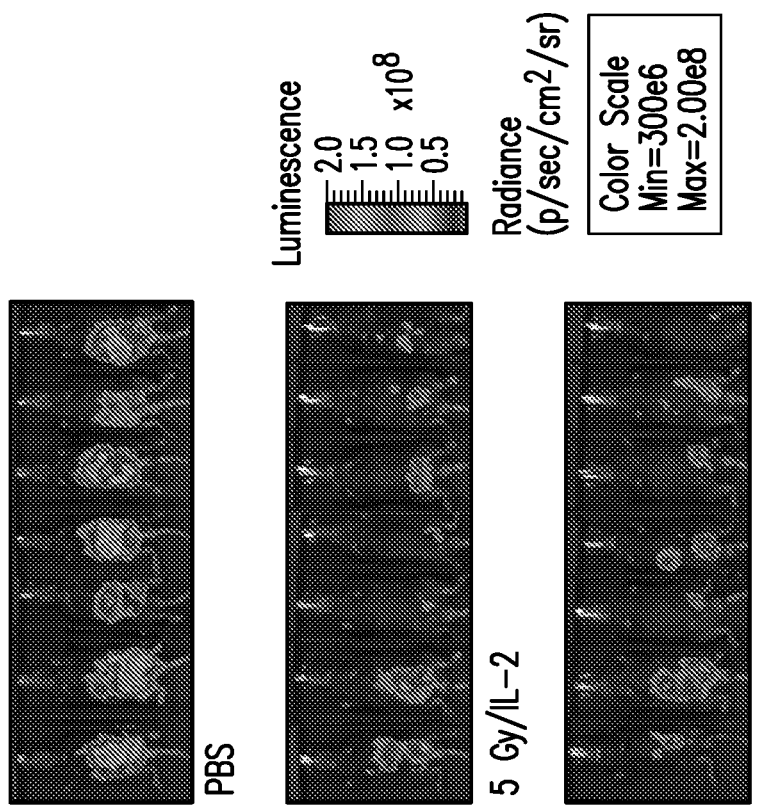
Figure 33C:
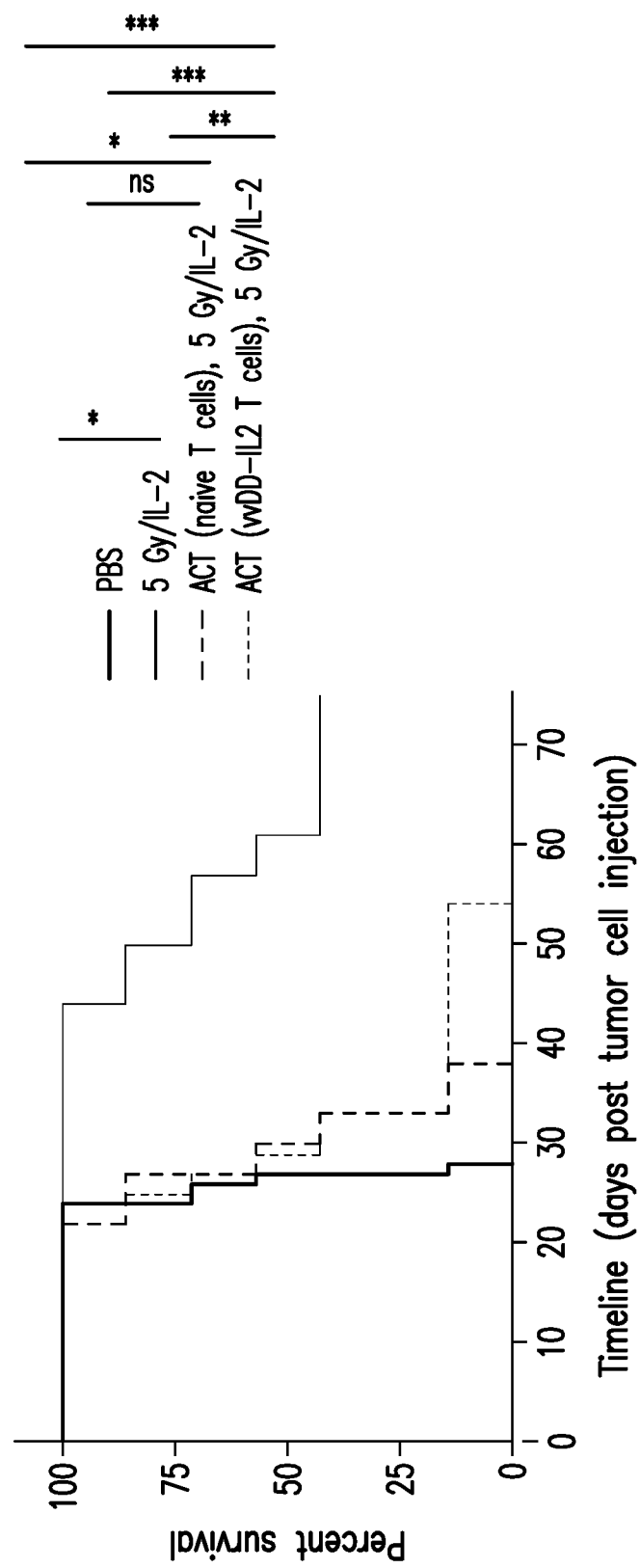

FIG. 33A-C. Adoptive T cell transfer of vvDD-IL-2 induced T cells into MC38 i.p. tumor bearing mouse. (A) Experimental setup: To generate virus induced T cells for adoptive T cell transfer B6 mice were s.c. inoculated with $5 \times 10^5$ MC38 cancer cells (n=12). When the tumor area reached $5 \times 5$ mm$^2$ vvDD-IL-2 ($1 \times 10^8$ pfu per tumor) was intratumorally injected. 10 days later tumors have been collected (2 samples have been pooled together, n=6) and proceed to single cell suspension followed by magnetic separation (CD90.2 beads). T cells have been expanded in 24-well plates ($1 \times 10^6$ per well) in RPMI complete media in the presence of IL-2 (30 IU/ml) and IL-7 (5 ng/ml). As control T cells, spleens from non-tumor bearing untreated mouse (n=4) have been harvested and proceed to single cell suspension followed by magnetic separation (CD90.2 beads). The naïve T cells have been cultured under the same conditions as the virus induced T cells. T cells have been harvested for adoptive transfer ($5 \times 10^6$ T cells per mouse) 4 days later. The ACT treatment mouse have been intraperitoneally inoculated with $5 \times 10^5$ MC38-luc cancer cells 7 days prior to treatment and divided into required groups according to tumor growth condition based on live animal IVIS imaging 7 days post tumor cell injection (n=7). Prior to T cell transfer treated mouse received 5 Gy of sublethal irradiation to mimic lymphodepletion similar to clinical protocols. Grouped mouse were intraperitoneally injected with vvDD-IL-2 induced T cells, naïve T cells or PBS. All treated mouse received exogenous cytokine support of IL-2 (100.000 IU/mouse i.p. for 3 days every 12 h). (B) The survival of tumor-bearing mouse was monitored by Kaplan-Meier analysis. (C) The tumor growth has been monitored by live animal imaging.

Figure 34B:
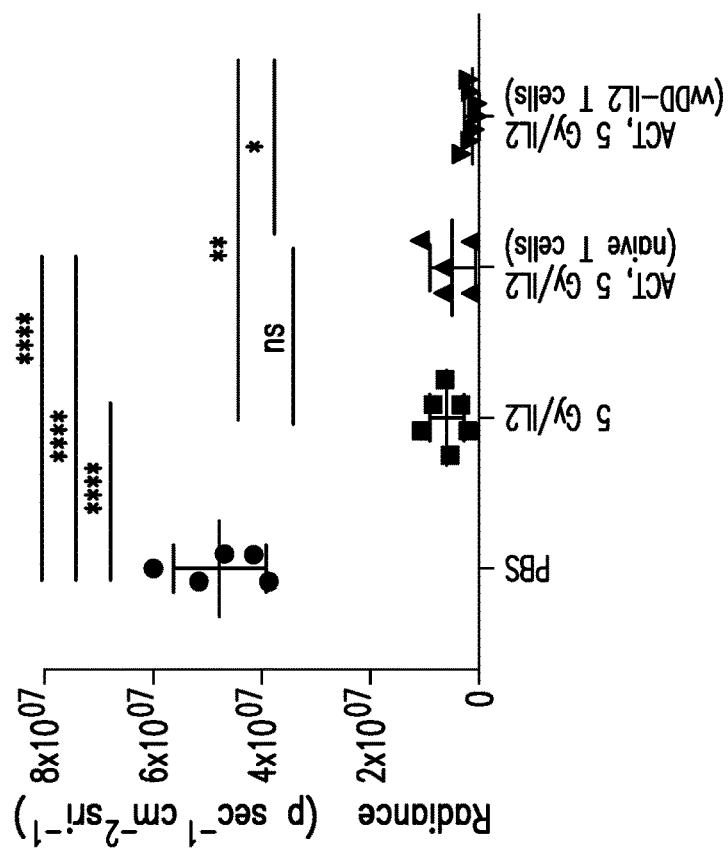
Figure 34A:
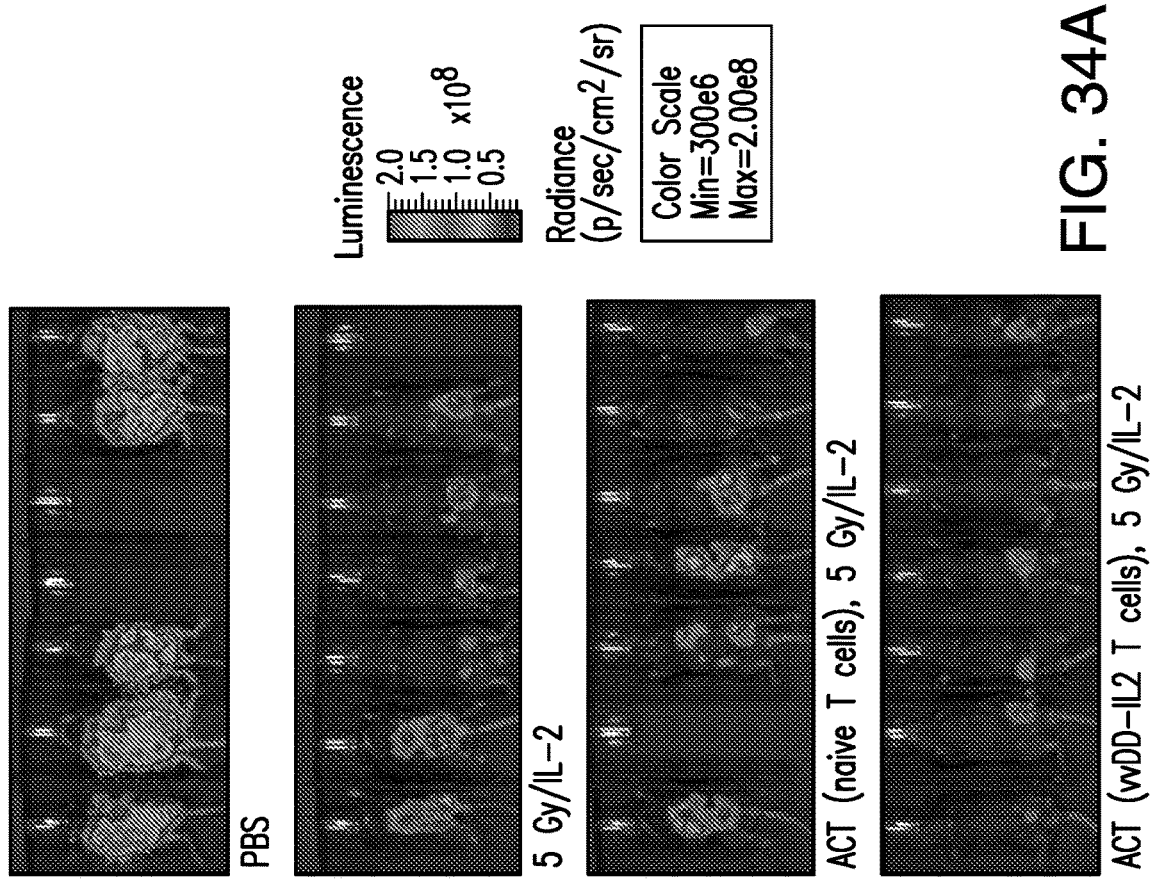

FIG. 34. Imaging Day 17 post ACT.

5. DETAILED DESCRIPTION OF THE INVENTION

For clarity and not by way of limitation, the detailed description of the presently disclosed subject matter is divided into the following subsections:
 (i) Oncolytic viruses;
 (ii) Immunomodulator molecules;
 (iii) Armed oncolytic viruses;
   a. Secreted immunomodulator molecules;
   b. Membrane bound immunomodulator molecules;
     i. Anchoring peptides;
     ii. Linkers;
     iii. Non-limiting embodiments;

(iv) Oncolytic virus administration;
(v) Methods of manufacture;
   a. Isolation and preparation of tumor infiltrated T cells—induced by oncolytic virus ("OV-induced T cells");
(vi) Methods of treatment;
   a. Adoptive T-cell therapy;
   b. Treatment with armed oncolytic viruses;
(vii) Pharmaceutical compositions; and
(viii) Kits.

5.1. Oncolytic Viruses

The presently disclosed subject matter can be applied to any oncolytic virus known in the art. An "oncolytic virus" is a virus that exhibits increased replication in, and lysis of, cancer cells relative to comparable non-cancer cells; see, for example, Bartlett D L et al., 2013, Molecular Cancer 12:103-120; Kaufman H L et al., 2015, Nature Reviews Drug Discovery 14:642-662 and Chiocca EA and Rabkin S D, 2014, Cancer Immunol Res; 2; 295-300. In certain embodiments, the oncolytic virus exhibits selective replication in cancer cells and less or essentially no replication in non-cancer cells. In certain embodiments, less replication means that replication in cancer cells versus comparable non-cancer cells is at least about 30 percent greater, or at least about 50 percent greater, or at least about 80 percent greater.

The term "about" or "approximately," as used herein, can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" can mean an acceptable error range for the particular value, such as ±10% of the value modified by the term "about."

Non-limiting examples of oncolytic viruses include types of (i) adenovirus ("Ad"), for example hTERT-Ad; (ii) herpes simplex virus ("HSV"), for example G207, HSV-1716, T-VEC, and HSV-2 APK mutant; (iii) poxvirus, for example vaccinia virus, for example vSP and vvDD (tk−/vgf−) (and see below); (iv) arbovirus; (v) paramyxovirus, for example, measles virus, mumps and Newcastle disease virus; (vi) rhabdovirus, for example, vesicular stomatitis virus; (vii) picornavirus, for example Coxsackie virus, Seneca Valley Virus, and polio virus; (viii) reovirus; (ix) parvovirus; and (x) recombinant/engineered versions of any one of the above.

In certain embodiments, the oncolytic virus is an oncolytic virus that has been approved by the Food and Drug Administration (FDA) or is undergoing clinical trials. For example, but not by way of limitation, the oncolytic virus can be Talimogene laherparepvec (Imlygic™; Amgen, Inc.), also referred to as T-VEC. In certain embodiments, the oncolytic virus can be pelareorep (Reolysin®; Oncolytics Biotech, Inc.). In certain embodiments, the oncolytic virus can be DNX-2401 (DNAtrix Therapeutics). In certain embodiments, the oncolytic virus can be H101 (Oncorine®; Shanghai Sunway Biotech Co., Ltd.). In certain embodiments, the oncolytic virus can be pexastimogene devacirepvec (JX-594; SillaJen Inc.). In certain embodiments, the oncolytic virus can be CG0070 (Cold Genesys, Inc.). In certain embodiments, the oncolytic virus can be G47Δ (Daiichi-Sankyo Company, Limited).

In certain embodiments, the oncolytic virus is a vaccinia virus. In certain non-limiting embodiments, the oncolytic virus is an engineered (also referred to as "recombinant") vaccinia virus. In certain non-limiting embodiments, the virus is a recombinant vaccinia virus based on the Western Reserve ("WR") strain of vaccinia, for example, the WR strain commercially available from the American Type Culture Collection as ATCC No. VR1354. Other vaccinia virus strains suitable for engineering include, but are not limited, to the Wyeth strain (ATCC VR-1536), the Lederle-Chorioallantoic strain (ATCC VR-325), and the CL strain (ATCC VR-117).

In certain non-limiting embodiments, the oncolytic virus is an engineered vvDD vaccinia viral construct comprising, for example, a modified version of a virus described in U.S. Pat. Nos. 7,208,313, 8,506,947, and United States Patent Application Publications Nos. 2003/0031681 and 2007/0154458, McCart et al., 2001, Cancer Research 61:8751-8757 and/or Thorne S et al., 2007, J. Clin. Invest. 117:3350-3358, all of which are incorporated by reference herein in their entries. For example, but not by way of limitation, the vaccinia virus can have deletions of the thymidine kinase (tk) and/or vaccinia growth factor (vgf) genes.

In certain non-limiting embodiments, a vaccinia virus has an inactivating mutation in one or more gene where the product of said gene or genes functions in viral replication. For example, but not by way of limitation, one or more of the following genes can bear an inactivating mutation: the gene encoding the ribonucleotide reductase-large subunit, the gene encoding the ribonucleotide reductase-small subunit, the gene encoding thymidylate kinase, the gene encoding DNA ligase, the gene encoding dUTPase, the tk gene, and the vaccinia virus growth factor (vgf) gene. In certain embodiments, an inactivating mutation is a mutation that either reduces or eliminates activity of the gene product. In certain embodiments, gene activation can be achieved by mutagenesis, e.g., site-directed mutagenesis or PCR-mediated mutagenesis.

Alternatively or additionally, in certain embodiments, a nucleic acid can be inserted into one or more of the foregoing genes to achieve inactivation. In certain non-limiting embodiments, a nucleic acid encoding a protein can be inserted into one or more of the foregoing genes to achieve inactivation and to further achieve expression of the nucleic acid. In certain embodiments, a nucleic acid encoding an immunomodulator molecule can be inserted within one of the foregoing genes to achieve inactivation. In certain embodiments, a nucleic acid encoding an immunomodulator molecule linked to an anchoring peptide (e.g., an ANCHIM protein) can be inserted within one of the foregoing genes to achieve inactivation and, optionally, the ANCHIM protein can be expressed.

In certain non-limiting embodiments, the oncolytic virus is a vaccinia virus having an inactivating mutation (a mutation that either reduces or eliminates activity of the gene product) in the tk gene. For example, but not limited to, the inactivation of the thymidine kinase gene can be generated by the insertion of a cytosine deaminase (fcy1) gene within the thymidine kinase gene locus of the vaccinia viral genome, resulting in the expression of the fcy1 gene rather than the tk gene. In another non-limiting embodiment, a nucleic acid encoding a detectable protein, for example a fluorescent protein, for example yellow fluorescent protein ("yfp"), can be inserted into the tk gene, thereby inactivating it. In certain embodiments, a nucleic acid encoding an immunomodulator can be inserted into the tk gene. In certain embodiments, a nucleic acid encoding an ANCHIM protein can be inserted into the tk gene.

In additional or alternative embodiments, the recombinant vaccinia virus can have an inactivating mutation in the vaccinia growth factor gene. For example, but not by way of limitation, an insertion of a lacZ gene within the vgf gene locus, resulting in the expression of the lacZ gene rather than vgf. In certain embodiments, a nucleic acid encoding an immunomodulator can be inserted into the vgf gene. For example, but not by way of limitation, a nucleic acid encoding an ANCHIM protein can be inserted into the vgf gene.

5.2. Immunomodulator Molecules

Any immunomodulator molecule known in the art can be utilized according to the presently disclosed subject matter. Certain cytokines have immunomodulatory activity and would be considered immunomodulator molecules (or, simply, "immunomodulators") herein.

In certain embodiments, an immunomodulator molecule can comprise a cytokine. In certain embodiments, an immunomodulator molecule can comprise a chemokine. Non-limiting examples of immunomodulator molecules which can be used according to the presently disclosed subject matter include an interleukin ("IL"), for example IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24 or IL-27, C—X—C motif chemokine 11 (CXCL11), Chemokine (C-C motif) ligand 5 (CCL5), an interferon ("IFN"), for example, IFN-alpha, IFN-alpha2, IFN-beta, or IFN-gamma; or a tumor necrosis factor ("TNF"), for example TNF-alpha or TNF-beta; and granulocyte macrophage colony-stimulating factor (GM-CSF).

The immunomodulator molecule can be a human or non-human immunomodulator molecule. Nucleic acid sequences encoding such immunomodulator molecules, and the encoded protein sequences, are well known in the art. Examples of non-human species include non-human primates, rodents, rabbits, dogs, cats, horses, pigs, sheep, cows, etc.

In certain non-limiting embodiments, the immunomodulator molecule for use in the presently disclosed subject matter is IL-2. In certain embodiments, human IL-2 comprises at least an immune-activating portion of the sequence APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:13; GenBank Acc. No. CAA25742.1, residues 21-153), or conservative substitutions thereof, e.g., said sequence having one or two amino acid variations.

In certain non-limiting embodiments, the immunomodulator molecule for use in the presently disclosed subject matter is TNF-alpha. In certain non-limiting embodiments, the human TNF-alpha comprises at least an immune-activating portion of the sequence MSTESMIRDVELAEE-ALPKKTGGPQGSRRCLFLSLF SFLIVAGATTLFCLL-HFGVI GPQREEFPRDLSLISPLAQAVRSSSRTPSDKP-VAHVVANPQAEGQLQWLNRRANA LLANGVELR-DNQLVVPSEGLYLIYSQVLFKGQGCPSTHVLLTHTIS-RIAVSYQTK VNLLSAIKSPCQRETPEGAEAKPW-YEPIYLGGVFQLEKGDRLSAEINRPDYLDFAE SGQVYFGIIAL (SEQ ID NO:15; NCBI Ref. Sequence No. NM_000594.3) or conservative substitutions thereof, e.g., said sequence having one or two amino acid variations.

In certain non-limiting embodiments, the immunomodulator molecule for use in the presently disclosed subject matter is IL-23, which consists of the two subunits, IL-23A and IL-12B. In certain non-limiting embodiments, the human IL-23A protein comprises at least an immune-activating portion of the sequence MLGSRA-VMLLLLLPWTAQGRAVPGGSSPAWTQCQQLSQ-KLCTLAWSAHPLVG HMDLREEGDEETTNDVPH-IQCGDGCDPQGLRDNSQFCLQRIHQGLIFYEKLLGSD IFTGEPSLLPDSPVGQLHASLLGLSQLLQPEGHH-WETQQIPSLSPSQPWQRLLLRF KILRSLQAFVA-VAARVFAHGAATLSP (SEQ ID NO:18; GenBank Acc. No. XXX, residues 1-189 or amino acid residues 28-184 of SEQ ID NO:18), or said sequence having one amino acid variation.

In certain non-limiting embodiments, the presently disclosed subject matter can also be applied using a non-immunomodulator cytokine where said cytokine is desirably localized to the cancer cell environment, for example where said cytokine exhibits toxic effects when systemically administered.

As used herein, the terms "conservative amino acid substitutions" and "conservative modifications" refer to amino acid modifications that do not significantly affect or alter the function and/or activity of the presently disclosed proteins comprising the amino acid sequence. Such conservative modifications include amino acid substitutions, additions and deletions. Modifications can be introduced into the proteins of this disclosure by standard techniques known in the art, such as site-directed mutagenesis and PCR-mediated mutagenesis. Amino acids can be classified into groups according to their physicochemical properties such as charge and polarity.

Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. In certain embodiments, no more than one, no more than two, no more than three, no more than four, no more than five residues within a specified sequence are altered. Exemplary conservative amino acid substitutions are shown in Table 1 below.

TABLE 1

| Original Residue | Exemplary Conservative Amino Acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gin (Q) | Asn; Glu |
| Glu (E) | Asp; Gln |
| Gly (G) | Ala |
| His (H) | Asn; Gln; Lys; Arg |

TABLE 1-continued

| Original Residue | Exemplary Conservative Amino Acid Substitutions |
|---|---|
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

5.3. Armed Oncolytic Viruses

The presently disclosed subject matter provides for an oncolytic virus that comprises a nucleic acid that encodes an immunomodulator molecule as set forth above. In certain embodiments, the immunomodulator molecule encoding by the nucleic acid can be secreted, e.g., secreted from the cell infected by the oncolytic virus that comprises the nucleic acid. In certain embodiments, the immunomodulator molecule can be linked to an anchoring peptide to become membrane-associated.

5.3.1. Secreted Immunomodulator Molecules

The presently disclosed subject matter provides for an oncolytic virus that comprises a nucleic acid that encodes an immunomodulator molecule that is to be secreted, e.g., secreted from the cell infected by the oncolytic virus that comprises the nucleic acid. Suitable oncolytic viruses and immunomodulator molecules are discussed in the sections above. In certain embodiments, the immunomodulator molecule can be of the same species as the subject intended to be treated (for example a human immunomodulator molecule to treat a human subject) or can be of a different species (for example a mouse immunomodulator molecule to treat a human subject).

In certain non-limiting embodiments, the presently disclosed subject matter provides for an oncolytic virus, comprising, in its genome, a nucleic acid, encoding an immunomodulator molecule. In certain embodiments, the oncolytic virus is a herpes simplex virus, a vaccinia virus, an adenovirus or a vesicular stomatitis virus.

In certain embodiments, the immunomodulator molecule can be IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, CXCL11, CCL5, an IFN, IFN-alpha, IFN-alpha2, IFN-beta, IFN-gamma, a TNF, TNF-alpha, TNF-beta, GM-CSF or a combination thereof. In certain embodiments, the immunomodulator molecule is IL-2. In certain embodiments, the immunomodulator molecule is IL-23. In certain embodiments, the immunomodulator molecule is TNF-alpha.

In certain embodiments, the nucleic acid encoding the immunomodulator molecule can be placed under the control of a promoter that is active or activatable in an oncolytic virus infected cell, for example, a promoter of the oncolytic virus. The encoding nucleic acid can be DNA, RNA or cDNA to conform to the nucleic acid of the viral genome into which it is inserted.

In certain embodiments, the oncolytic virus is a herpes simplex virus. In certain embodiments, the herpes virus comprises, in its genome, a nucleic acid that encodes an immunomodulator molecule, as described above. In certain embodiments, the nucleic acid encoding the immunomodulator molecule can be placed under the control of a promoter that is active or activatable in a herpes simplex virus infected cell, for example, a promoter of the herpes simplex virus. The encoding nucleic acid can be DNA to conform to the nucleic acid of the genome of the herpes simplex virus. In certain embodiments, an oncolytic virus of the present disclosure can be a herpes simplex virus that comprises a nucleic acid that encodes IL-2. In certain embodiments, an oncolytic virus of the present disclosure can be a herpes simplex virus that comprises a nucleic acid that encodes IL-23. In certain embodiments, an oncolytic virus of the present disclosure can be a herpes simplex virus that comprises a nucleic acid that encodes TNF-alpha.

In certain embodiments, the oncolytic virus is a vaccinia virus. In certain embodiments, the nucleic acid encoding the immunomodulator molecule is operably linked to a promoter active or activatable in a vaccinia virus-infected cell, for example, a vaccinia virus promoter. In certain non-limiting embodiments, the nucleic acid encoding the immunomodulator molecule can be operably linked to a vaccinia promoter, for example the p7.5 e/l promoter, or the pSe/l promoter to generate a promoter/immunomodulator molecule-encoding construct. In certain non-limiting embodiments, the promoter/immunomodulator-encoding construct can be inserted into the tk gene. In certain other non-limiting embodiments, the promoter/immunomodulator-encoding construct can be inserted into the vgf gene. In certain embodiments, an oncolytic virus of the present disclosure can be a vaccinia virus that comprises a nucleic acid that encodes IL-2. In certain embodiments, an oncolytic virus of the present disclosure can be a vaccinia virus that comprises a nucleic acid that encodes IL-23. In certain embodiments, an oncolytic virus of the present disclosure can be a vaccinia virus that comprises a nucleic acid that encodes TNF-alpha.

In certain non-limiting embodiments, the presently disclosed subject matter provides for an oncolytic vaccinia virus, comprising, in its genome, a nucleic acid, which is a deoxyribose nucleic acid, encoding IL-2. In a specific, non-limiting embodiment, the nucleic acid can encode human IL-2 (e.g., comprising at least a portion of the amino acid sequence of SEQ ID NO:13 or conservative substitutions thereof). In certain embodiments, the nucleic acid encoding IL-2 is operably linked to a promoter active or activatable in a vaccinia virus-infected cell, for example, a vaccinia virus promoter. For example, but not by way of limitation, the nucleic acid encoding IL-2 can be operably linked to a vaccinia promoter, for example the p7.5 e/l promoter, or the pSe/l promoter to generate a promoter/IL-2-encoding construct. In certain non-limiting embodiments, the promoter/IL-2-encoding construct can be inserted into the tk gene. In certain other non-limiting embodiments, the promoter/IL-2-encoding construct can be inserted into the vgf gene.

In certain non-limiting embodiments, the presently disclosed subject matter provides for an oncolytic vaccinia virus, comprising, in its genome, a nucleic acid, which is a deoxyribose nucleic acid, encoding TNF-alpha. In a specific, non-limiting embodiment, the nucleic acid can encode human TNF-alpha (e.g., comprising the amino acid sequence of SEQ ID NO:15 or conservative substitutions thereof). In certain embodiments, the nucleic acid encoding TNF-alpha is operably linked to a promoter active or activatable in a vaccinia virus-infected cell, for example a vaccinia virus promoter. For example, but not by way of limitation, the nucleic acid encoding TNF-alpha can be operably linked to a vaccinia promoter, for example the p7.5 e/1 promoter, or the pSe/1 promoter to generate a promoter/TNF-alpha-encoding construct. In certain non-limiting embodiments, the promoter/TNF-alpha-encoding construct can be inserted into the tk gene. In certain other non-limiting embodiments, the promoter/IL-2-encoding construct can be inserted into the vgf gene.

In certain non-limiting embodiments, the presently disclosed subject matter provides for an oncolytic vaccinia virus, comprising, in its genome, a nucleic acid, which is a deoxyribose nucleic acid, encoding the subunits of IL-23, e.g., IL-23p19 and IL-23p40. In certain embodiments, the nucleic acid encoding IL-23p19 and IL-23p40 is operably linked to a promoter active or activatable in a vaccinia virus-infected cell, for example, a vaccinia virus promoter. In certain non-limiting embodiments, the oncolytic vaccinia virus, comprising, in its genome, a nucleic acid, which is a deoxyribose nucleic acid, that encodes a human homologue of IL-23p19, e.g., IL-23A, and a human homologue of IL-23p40, e.g., IL-12B, to generate IL-23. In a specific, non-limiting embodiment, the nucleic acid can encode IL-23p19 or a human homologue thereof, for example IL-23A, and/or IL-23p40 or a human homologue thereof, for example IL-12B, and can further be operably linked to a vaccinia promoter, for example the p7.5 e/1 promoter, or the pSe/1 promoter to generate a promoter/IL-23p19/IL-23p40-encoding construct or a promoter/IL-23A/IL-12B-encoding construct. In certain non-limiting embodiments, the promoter/IL-23p19/IL-23p40-encoding construct or a promoter/IL-23A/IL-12B-encoding construct can be inserted into the tk gene. In certain other non-limiting embodiments, the promoter/IL-23p19/IL-23p40-encoding construct or a promoter/IL-23A/IL-12B-encoding construct can be inserted into the vgf gene.

5.3.2. Membrane Bound Immunomodulator Molecules

The presently disclosed subject matter provides for an oncolytic virus encoding a membrane-associated protein comprising an immunomodulator molecule as set forth above linked to an anchoring peptide, where the immunomodulator molecule linked to the anchoring peptide is referred to herein as the "ANCHIM". In certain embodiments, the membrane attachment domain is heterologous. In certain embodiments, the membrane attachment domain is autologous. Suitable oncolytic viruses and immunomodulator molecules are discussed in the sections above. Anchoring peptides are discussed in the sections below.

In certain embodiments, the immunomodulator molecule can be of the same species as the subject intended to be treated (for example a human immunomodulator molecule to treat a human subject) or can be of a different species (for example a mouse immunomodulator molecule to treat a human subject).

In certain non-limiting embodiments, the presently disclosed subject matter provides for an oncolytic virus, comprising, in its genome, a nucleic acid, encoding a membrane-associated protein comprising an immunomodulator molecule linked to an anchoring peptide. In certain embodiments, the oncolytic virus is a herpes simplex virus, a vaccinia virus, an adenovirus or a vesicular stomatitis virus. In certain embodiments, the immunomodulator molecule can be IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, CXCL11, CCL5, an IFN, IFN-alpha, IFN-alpha2, IFN-beta, IFN-gamma, a TNF, TNF-alpha, TNF-beta, GM-CSF or a combination thereof. In certain embodiments, the immunomodulator molecule is IL-2. In certain embodiments, the immunomodulator molecule is IL-23. In certain embodiments, the immunomodulator molecule is TNF-alpha.

5.3.2.1. Anchoring Peptides

In certain embodiments, an anchoring peptide is any protein which, when fused to an immunomodulator molecule, anchors the immunomodulator molecule to the host cell membrane. In certain embodiments, an anchoring peptide can be used according to the presently disclosed subject matter to modify an immunomodulator molecule to bind to the membrane of the host cell (e.g., by adding a GPI or other molecule).

In certain non-limiting embodiments, the anchoring peptide is between about 10 and about 50 amino acids, or between about 15 and about 30, or about 20 amino acids in length.

In certain embodiments, the anchoring peptide is a glycosylphosphatidylinositol (GPI)-anchor acceptor peptide. In certain non-limiting embodiments, the GPI anchor acceptor peptide comprises at least a portion of the C terminus of its native peptide, for example comprises at least a portion of the 100 C-terminal amino acids, or at least a portion of the 50 C-terminal amino acids, of the native peptide, or at least a portion of the 30 C-terminal amino acids.

In certain embodiments, the anchoring peptide can comprise sequences of various proteins as well as portions of cell membrane proteins that would serve essentially the same function. As exemplified by GPI, the anchoring function can be achieved by a modification of an underlying peptide or protein that contains non-peptide elements, including but not limited to carbohydrate, lipid, etc.

In certain embodiments, the anchoring peptide can comprise a glycosylphosphatidylinositol (GPI)-anchor acceptor sequence of human CD16b anchor acceptor peptide. In certain non-limiting embodiments, the anchor is a GPI anchor acceptor peptide from a protein as set forth in Ferguson et al., "Chapter 11: Glycosylphosphatidyl Anchors" in *Glycobiology, 2nd Edition*, Varki et al., editors, Cold Spring Harbor Press, 2009, for example but not limited to alkaline phosphatase, CD58, CD14, NCAM-120 and TAG-1, the contents of which are incorporated in their entirety by reference herein.

In certain non-limiting embodiments, the GPI anchor acceptor peptide comprises a signal peptide portion ("SPP"), which functions during GPI addition and is cleaved in the process. In certain embodiments, a SPP comprises three domains: (1) a first domain comprising three relatively small amino acids (for example, but not limited to, Gly (G), Ala (A), Ser (S), Asn (N), Asp (D), or Cys (C) or any combination thereof) $\omega$, $(\omega+1)$, and $(\omega+2)$, where $\omega$ is attached to the GPI anchor and $(\omega+1)$ and $(\omega+2)$ are the first 2 residues of the cleaved peptide; (2) a relatively polar domain spacer of about 5-10 amino acid residues and (3) a hydrophobic domain of about 15-20 amino acids. In certain embodiments, the anchoring peptide can further comprise a sequence that targets it to the endoplasmic reticulum to facilitate addition of the GPI anchor if that is not a feature viral infection (see Mayor S and Riezman H, 2004, Nature Reviews Molecular Cell Biology 5, 110-120, the contents of which are incorporated in their entirety by reference herein. This signal peptide portion, extending from the protein C terminus, can be diagrammed as: $\omega-(\omega+1)-(\omega+2)$–polar spacer region––hydrophobic domain (see Galian C et al., 2012, J. Biol. Chem. 287(20):16399-16409). In certain non-limiting embodiments, the ω-(ω+1)-(ω+2)-polar spacer region can include a sequence of about ten amino acids of which at least about 2 or at least about 3 residues are G and at least about 2 or at least about 3 or at least about 4 or at least about 5 residues are S. In particular non-limiting embodiments, the sequence can be NSTGSGSSGS (SEQ ID NO:17; Galian, supra). In certain non-limiting embodiments, the hydrophobic domain can include between about 15 and about 20 amino acids comprising at least about 10 residues selected from the group of A, Leu (L), Val (V), Phe (F) and combinations thereof. Non-limiting examples of SPPs are provided in Table 1 or FIG. 8 of Galian, supra, and include:

```
                        (SEQ ID NO: 2; from human CD24)
GGALQSTASLFVVSLSLLHLYS;

(SEQ ID NO: 3; from human EFNA2)
NNSCSSPGGCRLFLSTIPVLWTLL;

(SEQ ID NO: 4; from human PPB1)
DAAHPGRSVVPALLPLLAGTLLLLETAT;

(SEQ ID NO: 5; from human EFNA1)
SAAPRLFPLAWTVLLLPLLLLQT;

(SEQ ID NO: 6; from human LSAMP)
NGSISLAVPLWLLAASLLCLLSCK;

(SEQ ID NO: 7, from human CNTN1)
SGAPTLSPSLLGLLLPAFGILVYLEF;

(SEQ ID NO: 8, from rat NTRI)
NGTSRRAGCIWLLPLLVLHLLLKF;

(SEQ ID NO: 9)
NSTGSGSSGSAAAAVAAAAVAAAAVAAAA;
or
                        (SEQ ID NO: 10)
NSTGSGSSGSAAAAVVFVFVFVFVVAAAA.
```

In certain embodiments, the GPI anchor acceptor peptide sequence comprises any one of peptides having SEQ ID NO: 2-10 bearing about 1 or about 2 amino acid substitutions, insertions or deletions, or about 1, about 2 or about 3 conservative amino acid substitutions.

In a particular non-limiting embodiment, the GPI anchor acceptor peptide comprises the GPI anchor acceptor peptide sequence of CD16b comprising at least a portion, e.g., at least about 10 or at least about 20 or at least about 25 consecutive residues, of the sequence: SSFSPPGYQVSFCLVMVLLFAVDTGLYFSVKTNI (SEQ ID NO:1) or that sequence bearing about 1 or about 2 amino acid substitutions, insertions or deletions, or about 1, about 2 or about 3 conservative amino acid substitutions (see Simmons D and Seed B, 1988, Nature 333:568-570).

In a particular non-limiting embodiment, the GPI anchor acceptor peptide comprises the GPI anchor acceptor peptide sequence of CD16b comprising at least a portion, e.g., at least about 10 or at least about 20 or at least about 25 consecutive residues, of the sequence: VSTISSFSPPGYQVSFCLVMVLLFAVDTGLYFSVKTNI (SEQ ID NO:11) or that sequence bearing about 1 or about 2 amino acid substitutions, insertions or deletions, or about 1, about 2 or about 3 conservative amino acid substitutions (see Simmons D and Seed B, 1988, Nature 333:568-570). In certain non-limiting embodiments, the anchoring peptide does not act via GPI. In certain non-limiting embodiments, the anchoring peptide can anchor its attached protein to a cell membrane via fatty acid/diacylglycerol. In certain other non-limiting embodiments, the anchoring peptide comprises a region that can form a transmembrane domain, for example a substantially hydrophobic region and/or a region that is predicted to be a transmembrane domain by standard software, such as but not limited to TMpred. In certain embodiments, the anchoring peptide is a PD-L1 transmembrane domain.

In certain non-limiting embodiments, a nucleic acid encoding the immunomodulator molecule linked (optionally via a linker) to an anchoring peptide can be placed under the control of a promoter that is active or activatable in an oncolytic virus-infected cell, for example, a promoter of the oncolytic virus. The encoding nucleic acid can be DNA, RNA, or cDNA to conform to the nucleic acid of the viral genome into which it is inserted.

5.3.2.2. Linkers

In certain embodiments, the immunomodulator molecule can be linked directly to the anchoring peptide. Alternatively, the immunomodulator molecule can be linked to the anchoring peptide via a linker. In certain embodiments, the linker is selected from a cleavable linker, a non-cleavable linker, a peptide linker, a flexible linker, a rigid linker, a helical linker, a non-helical linker or a combination thereof. In certain embodiments, the immunomodulator molecule can be linked to the anchoring peptide via one or more linkers, e.g., two or more, three or more or four or more.

In certain embodiments, the linker is a peptide linker. In certain embodiments, the peptide linker comprises Gly and Ser. In certain embodiments, the peptide linker can, for example and not by way of limitation, be between about 1 and about 25 or between about 5 and about 20 or between about 5 and about 15 amino acids in length. Non-limiting examples of linkers for use in the presently disclosure subject matter are disclosed in International Patent Publication WO 2017/165464 (e.g., SEQ ID NOs:42, 44, 45, 75, 76, 77 and 78), the contents of which are incorporated by reference herein in its entirety.

In certain embodiments, the peptide linker comprises a flexible linker. In certain embodiments, the flexible linker can be (G4S)3, which corresponds to GGGGSGGGGSGGGGS (SEQ ID NO:12). In a particular non-limiting embodiment, the linker linked to the anchoring peptide can comprise the amino acid sequence GPAGGGGSGGGGSGGGGSVSTISSFSPPGYQVSF-CLVMV LLFAVDTGLYFSVKTNI (SEQ ID NO:16) or that sequence bearing about 1 or about 2 amino acid substitutions, insertions or deletions, or about 1, about 2 or about 3 conservative amino acid substitutions. Non-limiting examples of certain GPI-anchored cytokines are provided in United States Patent Application Publication No. US 2003/0105054 (e.g., paragraphs [0045] and [0075]) and U.S. Pat. No. 6,277,368, the contents of which are hereby incorporated by reference in their entireties.

In certain embodiments, the peptide linker comprises a rigid linker. In certain embodiments, the rigid linker can be (A(EA3K)4AAA) (SEQ ID NO: 36), which corresponds to AEAAAKEAAAKEAAAKEAAAKAAA. In certain embodiments, the linker comprises the amino acid sequence SEQ ID NO:36 or that sequence bearing about 1 or about 2 amino acid substitutions, insertions or deletions, or about 1, about 2 or about 3 conservative amino acid substitutions.

5.3.2.3. Non-Limiting Embodiments

In certain non-limiting embodiments, the presently disclosed subject matter provides for an oncolytic virus encoding a membrane-associated protein comprising an immunomodulator molecule as set forth above linked to an anchoring peptide, optionally, via a linker.

In certain embodiments, the oncolytic virus is a herpes simplex virus, a vaccinia virus, an adenovirus or a vesicular stomatitis virus. In certain embodiments, the immunomodulator molecule can be IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, CXCL11, CCL5, an IFN, IFN-alpha, IFN-alpha2, IFN-beta, IFN-gamma, a TNF, TNF-alpha, TNF-beta, GM-CSF or a combination thereof. In certain embodiments, the immunomodulator molecule is IL-2. In certain embodiments, the immunomodulator molecule is IL-23. In certain embodiments, the immunomodulator molecule is TNF-alpha.

In certain non-limiting embodiments, the anchoring peptide comprises at least a portion of any one of SEQ ID NOs:1-11, for example said portion comprising between at least about 10 or at least about 20 or at least about 25 consecutive amino acid residues. In a specific non-limiting embodiment, the anchoring peptide comprises the amino acid sequence of SEQ ID NO:11, or that sequence bearing about 1 or about 2 amino acid substitutions, insertions or deletions, or about 1, about 2 or about 3 conservative amino acid substitutions.

In certain non-limiting embodiments, the immunomodulator molecule is joined to the anchoring peptide by a peptide linker between about 1 and about 25 or between about 5 and about 15 amino acids in length. In certain non-limiting embodiments, the linker comprises at least a portion of any one of SEQ ID NOs:12 and 36, for example said portion comprising between at least about 10 or at least about 20 or at least about 25 consecutive amino acid residues. In certain non-limiting embodiments, the linker comprises the sequence (G4S)3 (SEQ ID NO:12) or conservative substitutions thereof. In certain non-limiting embodiments, the linker comprises the sequence (A(EA$_3$K)$_4$AAA) (SEQ ID NO: 36) or conservative substitutions thereof.

In certain embodiments, the oncolytic virus can comprise a gene encoding a membrane-associated fusion protein that includes an immunomodulator molecule fused to an anchoring peptide, e.g., a GPI anchor (e.g., a GPI-anchor acceptor sequence of human CD16b), via a rigid linker (alternatively referred to herein as "RGPI" or "RG"). In certain embodiments, the oncolytic virus can comprise a gene encoding a membrane-associated fusion protein that includes an immunomodulator molecule fused to an anchoring peptide, e.g., a GPI anchor (e.g., a GPI-anchor acceptor sequence of human CD16b), via a flexible linker (alternatively referred to herein as "FGPI" or "FG"). In certain embodiments the GPI anchor sequence can be replaced with a PD-L1 transmembrane domain.

In certain embodiments, the oncolytic virus can comprise a gene encoding a membrane-associated fusion protein that includes an immunomodulator fused to a PD-L1 transmembrane domain, via a rigid linker. In certain embodiments, the oncolytic virus can comprise a gene encoding a membrane-associated fusion protein that includes an immunomodulator fused to a PD-L1 transmembrane domain, via a (G4S)3 linker. In certain embodiments, the oncolytic virus can comprise a gene encoding a membrane-associated fusion protein that includes an immunomodulator fused to a PD-L1 transmembrane domain, via a flexible linker (alternatively referred to herein as "FPTM").

In certain embodiments, the presently disclosed subject matter provides for an oncolytic virus, e.g., a vaccinia virus, comprising, in its genome, a nucleic acid, which is a deoxyribose nucleic acid, encoding IL-2. In certain non-limiting embodiments, the IL-2 is human IL-2. In certain non-limiting embodiments, the human IL-2 comprises at least a portion of the amino acid sequence of SEQ ID NO:13 or conservative substitutions thereof, or said sequence having one amino acid or two amino acid variations. In certain embodiments, the IL-2 is linked to an anchoring peptide, optionally with a linker peptide between IL-2 and the anchoring peptide. In certain non-limiting embodiments, the anchoring peptide comprises at least a portion of any one of SEQ ID NOS: 1-11 and 17, for example said portion comprising between at least about 10 or at least about 20 or at least about 25 consecutive amino acid residues. In certain non-limiting embodiments, the IL-2 is joined to the anchoring peptide by a peptide linker between about 1 and about 25 or between about 5 and about 15 amino acids in length. In certain embodiments, the nucleic acid encoding IL-2 is operably linked to a promoter active or activatable in an oncolytic virus-infected cell, for example, an oncolytic virus promoter (e.g., a vaccinia virus promoter).

In certain non-limiting embodiments, the nucleic acid present in the genome of the oncolytic virus can encode human IL-2 (e.g., comprising the amino acid sequence of SEQ ID NO:13), linked to an anchoring peptide (e.g., comprising the amino acid sequence of SEQ ID NO:11) via a peptide linker (e.g., comprising the amino acid sequence of SEQ ID NO:12). For example, but not by way of limitation, the nucleic acid encodes APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLTGPAGGGGSGGGGSGGGGS VSTISSFSPPGYQVSFCLVMVLLFAVDTGLYFSVKTNI (SEQ ID NO:14) or that sequence bearing about 1 or about 2 amino acid substitutions, insertions or deletions, or about 1, about 2 or about 3 conservative amino acid substitutions. In certain non-limiting embodiments, said encoding nucleic acid can be operably linked to an oncolytic virus promoter. In certain embodiment, said encoding nucleic acid can be operably linked to a vaccinia promoter, for example the p7.5 e/l promoter, or the pSe/l promoter to generate a promoter/ANCHIM-encoding construct. In certain non-limiting embodiments, the promoter/ANCHIM-encoding construct can be inserted into the tk gene. In certain other non-limiting embodiments, the promoter/ANCHIM-encoding construct can be inserted into the vgf gene.

In certain non-limiting embodiments, the nucleic acid can encode human IL-2 (e.g., comprising the amino acid sequence of SEQ ID NO:13), linked to an anchoring peptide (e.g., comprising the amino acid sequence of SEQ ID NO: 11) via a peptide linker (e.g., comprising the amino acid sequence of SEQ ID NO: 12 and 36). In certain non-limiting embodiments, said encoding nucleic acid can be operably linked to a vaccinia promoter, for example the p7.5 e/l promoter, or the pSe/l promoter to generate a promoter/ANCHIM-encoding construct. In certain non-limiting embodiments, the promoter/ANCHIM-encoding construct can be inserted into the tk gene. In certain other non-limiting embodiments, the promoter/ANCHIM-encoding construct can be inserted into the vgf gene.

In certain non-limiting embodiments, the presently disclosed subject matter provides for an oncolytic vaccinia virus, comprising, in its genome, a nucleic acid, which is a deoxyribose nucleic acid, encoding TNF-alpha. In certain embodiments, TNF-alpha is linked to an anchoring peptide, optionally with a linker peptide between TNF-alpha and the anchoring peptide. In certain embodiments, the nucleic acid is operably linked to a promoter active or activatable in a vaccinia virus-infected cell, for example a vaccinia virus promoter. In certain non-limiting embodiments, the TNF-alpha is human TNF-alpha. In certain non-limiting embodiments, the human TNF-alpha comprises at least an immune-activating portion of SEQ ID NO:15, or said sequence having one or two amino acid variations. In certain non-limiting embodiments, the anchoring peptide comprises at least a portion of any one of SEQ ID NOS:1-11, for example said portion comprising at least between at least about 10 or at least about 20 or at least about 25 consecutive residues. In a specific non-limiting embodiment, the anchoring peptide comprises SEQ ID NO:11, or that sequence bearing about 1 or about 2 amino acid substitutions, insertions or deletions, or about 1, about 2 or about 3 conservative amino acid substitutions. In certain non-limiting embodiments, the TNF-alpha is joined to the anchoring peptide by a peptide linker between about 1 and about 25 or between about 5 and about 15 amino acids in length. In certain non-limiting embodiments, the linker comprises the sequence (G45)3 (SEQ ID NO:12). In certain non-limiting embodiments, said encoding nucleic acid can be operably linked to a vaccinia promoter, for example the p7.5 e/l promoter, or the pSE/L promoter, to generate a promoter/ANCHIM-encoding construct. In certain non-limiting embodiments, the promoter/ANCHIM-encoding construct can be inserted into the tk gene. In certain other non-limiting embodiments, the promoter/ANCHIM-encoding construct can be inserted into the vgf gene. In certain non-limiting embodiments, the linker comprises the sequence GGGGSGGGGSGGGGS (SEQ ID NO:12). In certain non-limiting embodiments, the linker comprises the sequence RIGID LINKER (SEQ ID NO:36).

In certain non-limiting embodiments, the presently disclosed subject matter provides for an oncolytic vaccinia virus, comprising, in its genome, a nucleic acid, which is a deoxyribose nucleic acid, encoding IL-23p19 and IL-23p40. In certain embodiments, the IL-23p19 and IL-23p40 are linked to an anchoring peptide, optionally with a linker peptide between IL-23p40 and the anchoring peptide. In certain embodiments, the nucleic acid encoding IL-23p19 is operably linked to a promoter active or activatable in a vaccinia virus-infected cell, for example, a vaccinia virus promoter. In certain non-limiting embodiments, the oncolytic vaccinia virus, comprising, in its genome, a nucleic acid, which is a deoxyribose nucleic acid, that encodes a human homologue of IL-23p19, e.g., IL-23A, and a human homologue of IL-23p40, e.g., IL-12B, to generate IL-23. In certain non-limiting embodiments, the human IL-23A protein comprises at least an immune-activating portion of the sequence SEQ ID NO:18 or said sequence having one amino acid variation.

In a specific, non-limiting embodiment, the nucleic acid can encode IL-23p19 or a human homologue thereof, for example IL-23A (e.g., comprising the amino acid sequence of SEQ ID NO: 18), and can further encode IL-23p40, or a human homologue thereof, for example IL-12B, linked to an anchoring peptide (e.g., comprising the amino acid sequence of SEQ ID NO: 11) via a peptide linker (e.g., comprising the amino acid sequence of SEQ ID NO:12 and 36). In certain non-limiting embodiments, said encoding nucleic acid can be operably linked to a vaccinia promoter, for example the p7.5 e/l promoter, or the pSe/l promoter to generate a promoter/ANCHIM-encoding construct. In certain non-limiting embodiments, the promoter/ANCHIM-encoding construct can be inserted into the tk gene. In certain other non-limiting embodiments, the promoter/ANCHIM-encoding construct can be inserted into the vgf gene.

In certain non-limiting embodiments, the presently disclosed subject matter provides for an oncolytic herpes simplex virus, comprising, in its genome, a nucleic acid, encoding an immunomodulator molecule linked to an anchoring peptide, optionally with a linker peptide between the immunomodulator molecule and the anchoring peptide, as described above. In certain embodiments, the nucleic acid encoding the immunomodulator molecule linked to an anchoring peptide, optionally with a linker peptide between the immunomodulator molecule and the anchoring peptide, can be placed under the control of a promoter that is active or activatable in an oncolytic herpes simplex virus infected cell, for example, a promoter of the oncolytic herpes simplex virus. The encoding nucleic acid linked to an anchoring peptide, optionally with a linker peptide between the immunomodulator molecule and the anchoring peptide can be DNA, RNA, or cDNA to conform to the nucleic acid of the viral genome into which it is inserted.

The presently disclosed subject matter further provides for pharmaceutical compositions comprising one or more of the above-described engineered (recombinant) oncolytic viruses, for example in a physiologic buffer, and for such therapeutic compositions in solid, liquid, frozen, or lyophilized form. The presently disclosed subject matter further provides for a delivery device, for example a syringe, containing a therapeutically effective amount of such a pharmaceutical composition. Non-limiting examples of pharmaceutical compositions comprising one or more oncolytic viruses described herein are disclosed in section 5.7 below.

5.4. Oncolytic Virus Administration

The oncolytic viruses disclosed herein, e.g., armed oncolytic viruses, can be administered according to any known method in the art. For example, but not by way of limitation, a method for the delivery of an oncolytic virus, e.g., a vaccinia virus, as described herein or a pharmaceutical composition thereof or compositions that include anti-tumor T cells isolated from cancer tissue, to cancer or tumor cells can be via intratumoral injection. In certain embodiments, alternate methods of administration can also be used, e.g., intravenous, via infusion, parenteral, intravenous, intradermal, intramuscular, transdermal, rectal, intraurethral, intravaginal, intranasal, intrathecal, or intraperitoneal. The routes of administration can vary with the location and nature of the tumor. In certain embodiments, the route of administration can be intradental, transdermal, parenteral, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. In certain embodiments, the modified virus can be administered to the patient from a source implanted in the patient.

In certain embodiments, administration of the modified virus can occur by continuous infusion over a selected period of time. In certain embodiments, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60 minutes, about 75 mins, about 90 mins, about 100 mins, or about 120 mins or longer.

The oncolytic vaccinia virus or the pharmaceutical composition of the present disclosure can be administered as a liquid dosage, wherein the total volume of administration is about 1 ml to about 5 ml, about 5 ml to 10 ml, about 15 ml to about 20 ml, about 25 ml to about 30 ml, about 30 ml to about 50 ml, about 50 ml to about 100 ml, about 100 ml to 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to 500 ml, about 500 ml to 750 ml or about 750 ml to 1000 ml.

In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified virus can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months).

The terms "therapeutically effective amount" or "effective amount," as used interchangeably herein, can refer to the amount of oncolytic virus that, when administered, can be sufficient to prevent development of, or alleviate to some extent, one or more of the symptoms of the disorder, disease, or condition being treated. The term "therapeutically effective amount" can also refer to the amount of oncolytic virus that is sufficient to elicit the biological or medical response of a cell, tissue, system, animal or human. An effective amount in such method can include an amount that reduces growth rate or spread of the cancer or that prolongs survival in the subject. This disclosure provides a method of reducing the growth of a tumor, which method can comprise administering, to the tumor, an effective amount of a modified virus as described above. In certain embodiments, an effective amount of a modified virus, or a pharmaceutical composition thereof, can include an amount sufficient to induce the slowing, inhibition or reduction in the growth or size of a tumor and can include the eradication of the tumor. Reducing the growth of a tumor can be manifested, for example, by reduced growth rate or a prolonged survival of a subject containing the tumor. In certain embodiments, a "therapeutically effective amount" or "effective amount" can include an amount sufficient to induce the infiltration of T cells into the tumor and/or cancer.

An effective amount of virus can be determined by methods known in the art. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor.

In certain embodiments, the amount of virus administered can be between about $1\times10^7$ and $1\times10^{10}$ infectious viral particles or plaque forming units (pfu), or between about $1\times10^7$ and $1\times10^9$ pfu/m$^2$ surface area of the subject to be treated. In certain embodiments, the virus can be administered at a dose that can comprise about $1\times10^8$ pfu. In certain embodiments, the amount of virus administered can be between about $1\times10^3$ and $1\times10^{12}$ viral particles or pfu, or between about $1\times10^5$ and $1\times10^{10}$ pfu, or between about $1\times10^5$ and $1\times10^8$ pfu, or between about $1\times10^8$ and $1\times10^{10}$ pfu. In certain embodiments, the virus can be administered at a dose that can comprise about $1\times10^3$ pfu/dose to about $1\times10^4$ pfu/dose, about $1\times10^4$ pfu/dose to about $1\times10^5$ pfu/dose, about $1\times10^5$ pfu/dose to about $1\times10^6$ pfu/dose, about $1\times10^7$ pfu/dose to about $1\times10^8$ pfu/dose, about $1\times10^9$ pfu/dose to about $1\times10^{10}$ pfu/dose, about $1\times10^{10}$ pfu/dose to about $1\times10^{11}$ pfu/dose, about $1\times10^{11}$ pfu/dose to about $1\times10^{12}$ pfu/dose, about $1\times10^{12}$ pfu/dose to about $1\times10^{13}$ pfu/dose, about $1\times10^{13}$ pfu/dose to about $1\times10^{14}$ pfu/dose, or about $1\times10^{14}$ pfu/dose to about $1\times10^{15}$ pfu/dose. In certain embodiments, an oncolytic vaccinia virus of the presently disclosed subject matter can be administered at a dose that can comprise about $1\times10^3$ viral particles/dose to about $1\times10^4$ viral particles/dose, about $1\times10^4$ viral particles/dose to about $1\times10^5$ viral particles/dose, about $1\times10^5$ viral particles/dose to about $1\times10^6$ viral particles/dose, about $1\times10^7$ viral particles/dose to about $1\times10^8$ viral particles/dose, about $1\times10^9$ viral particles/dose to about $1\times10^{10}$ viral particles/dose, about $1\times10^{10}$ viral particles/dose to about $1\times10^{11}$ viral particles/dose, about $1\times10^{11}$ viral particles/dose to about $1\times10^{12}$ viral particles/dose, about $1\times10^{12}$ viral particles/dose to about $1\times10^{13}$ viral particles/dose, about $1\times10^{13}$ viral particles/dose to about $1\times10^{14}$ viral particles/dose, or about $1\times10^{14}$ viral particles/dose to about $1\times10^{15}$ viral particles/dose.

5.5. Methods of Manufacture

5.5.1. Isolation and Preparation of Tumor Infiltrated T Cells—Induced by Oncolytic Virus ("OV-Induced T Cells")

In certain embodiments, the presently disclosed subject matter relates to oncolytic viruses that promotes the infiltration of immune cells into the tumor microenvironment, thus becoming tumor-infiltrated immune cells induced by oncolytic virus.

In certain embodiments, the presently disclosed subject matter relates to oncolytic viruses that elicit systemic and potent anti-tumor immune cells, wherein the anti-tumor cells can be isolated from tumor tissues, expanded ex vivo, and administered to cancer patients for cancer treatments, e.g., in the mode of adoptive T cell transfer.

In certain embodiments, the presently disclosed subject matter relates to oncolytic viruses that promote the infiltration of T cells into the tumor microenvironment, thus becoming OV-induced T cells (also referred to herein as "tumor-infiltrated T cells" or "TILs"). In certain embodiments, the oncolytic virus promotes infiltration of tumor-specific CD8+ and CD4+ T cells. In certain embodiments, the oncolytic virus promotes infiltration of activated innate immune cells. In embodiments, the activated innate immune cells comprise natural killer (NK) cells.

In certain embodiments, the presently disclosed subject matter relates to a method of making OV-induced T cells that comprises administering, to the subject, an effective amount of an oncolytic virus and inducing the elicitation and trafficking of T cells into the tumor tissue of the subject. Non-limiting examples of oncolytic viruses are disclosed above in section 5.1 and 5.3. In certain embodiments, the oncolytic virus can be a vaccinia virus. For example, but not by way of limitation, the vaccinia virus can be vvDD. In certain embodiments, the oncolytic virus (e.g., vvDD) encodes, in expressible form, an immunomodulator molecule. For example, but not by way of limitation, the immunomodulator molecule can be IL-2, IL-15, CXC11 and/or CCL5. In certain embodiments, the presently disclosed subject matter relates to oncolytic vaccinia viruses (e.g., vvDD) encoding, in expressible form, at least one secreted and/or at least one membrane-associated immunomodulator molecule, as described above. In certain non-limiting embodiments, the oncolytic virus encodes, in an expressible form, IL-2, e.g., secreted or membrane-associated IL-2.

In certain embodiments, the method of making OV-induced T cells, further comprises isolating OV-induced T cells from the subject, e.g., from the tumor of the subject. In certain embodiments, OV-induced T cells can be isolated from lymphoid and non-lymphoid tissues or from peripheral blood. In certain embodiments, OV-induced T cells can be isolated from cancer tissue. For example, the T cells can be isolated from tissue by digesting the tissue and using density gradient centrifugation, e.g., using a Percoll density gradient.

In certain embodiments, the method of making OV-induced T cells, further comprises expanding the isolated OV-induced T cells ex vivo. In certain embodiments, during ex vivo expansion, the isolated OV-induced T cells can be treated with one or more cytokines, lymphokines, and/or one or more agents, for example, IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, IFN-alpha, IFN-alpha2, IFN-beta, IFN-gamma, TNF-alpha, TNF-beta, GM-CSF or combinations thereof. For example, but not by way of limitation, the isolated OV-induced T cells can be treated with IL-7, IL-2 and/or a GSK3b inhibitor. In certain embodiments, the OV-induced T cells can be treated with IL-2. In certain embodiments, the OV-induced T cells can be treated with IL-7. In certain embodiments, the OV-induced T cells can be treated with IL-2 and IL-7. In certain, non-limiting examples the isolated T cells can be treated for about two to about 10 days, e.g., about three days.

In certain embodiments, the isolated OV-induced T cells are co-cultured with dendritic and cancer cells. In certain embodiments, the OV-induced T cells can be co-cultured with cancer cells that have been infected with an oncolytic virus, e.g., an oncolytic virus disclosed herein. In certain embodiments, the cancer cells can be infected with an oncolytic virus that is different than the oncolytic virus used to generate the OV-induced T cells. In certain embodiments, the isolated OV-induce T cells are co-cultured with dendritic cells and cancer cells for about two to about 10 days, e.g., about two days. In certain embodiments, the co-cultured T cells are then treated with one or more cytokines and/or one or more agents.

In certain embodiments, to quantify the ability of the oncolytic virus to promote T cell infiltration in the tumor microenvironment, isolated OV-induced T cells can be analyzed with antibodies against CD3, CD8, CD4, and 4-1BB. In certain embodiments, the oncolytic virus promotes an infiltration of $CD3^+$, $CD8^+$, $CD4^+$, and $4\text{-}1BB^+$ T cells in the tumor microenvironment. In certain embodiments, the isolated OV-induced T cells are $CD3^+$, $CD8^+$, $CD4^+$ and/or $4\text{-}1BB^+$. In certain embodiments, the OV-induced T cells are $CD3^+$. In certain embodiments, the OV-induced T cells are $CD3^+$. In certain embodiments, the OV-induced T cells are $CD4^+$. In certain embodiments, the OV-induced T cells are $CD8^+$. In certain embodiments, the OV-induced T cells are $CD4^+4\text{-}1BB^+$. In certain embodiments, the OV-induced T cells are $CD8^+4\text{-}1BB^+$.

In certain embodiments, the OV-induced T cells can be used for cancer therapy via adoptive T cell transfer, as described in section 5.6.1. below. In certain embodiments, the presently disclosed subject matter relates to adoptive immunotherapy, wherein the tumor-infiltrated T cells can be isolated from tumor tissues, expanded ex vivo, and administered to cancer patients for cancer treatments, e.g., in the mode of adoptive T cell transfer. In certain embodiments, the OV-induced T cells can exert their functions to kill cancer cells and associated stromal cells. In certain embodiments, the OV-induced T cells can be transferred to the subject from which the cells were isolated. Alternatively and/or additionally, the OV-induced T cells can be transferred to a different subject. In certain embodiments, the OV-induced T cells are allogeneic.

In certain embodiments, prior to transfer of the isolated OV-induced T cells to a subject, the isolated OV-induced T cells can be analyzed for tumor specificity in a co-culture assay. In certain embodiments, the isolated OV-induced T cells are co-cultured with target cancer cells, irrelevant cancer cells or splenocytes from for about one to about 10 days, e.g., about one day. In specific embodiments, the cancer cells are γ-irradiated. In certain embodiments, the isolated OV-induced T cells are co-cultured with target cancer cells, irrelevant cancer cells or splenocytes. In certain embodiments, the isolated OV-induced T cells for transfer can present specific reactivity against the target tumor cells. In certain embodiments, the specific reactivity comprises an increase in the IFN-γ expression by the isolated OV-induced T cells when they are co-cultured with target cancer cells, compared when co-cultured with irrelevant target cancer cells or splenocytes.

5.6. Methods of Treatment

The present disclosure provides methods for the treatment of subjects that have cancer. In particular, the present disclosure provides methods for the treatment of a subject that has cancer that includes administering isolated OV-induced T cells to the subject that has cancer as a mode of adoptive T cell immunotherapy. The present disclosure further provides methods for the treatment of a subject that has cancer, which includes the administration of oncolytic viruses that are armed with an immunomodulator molecule, e.g., secreted or membrane associated.

Non-limiting examples of oncolytic viruses for use in the presently disclosed methods are disclosed above in sections 5.1, 5.3 and 5.5 above. Methods of administering oncolytic viruses is disclosed above in section 5.4 above. A subject can be a human or a non-human subject. Non-limiting examples of non-human subjects include non-human primates, dogs, cats, horses, pigs, cows, mice, rats, hamsters and other rodents, rabbits, etc.

Non-limiting examples of cancers that can be treated by the disclosed methods include gastrointestinal cancer, colon carcinoma, colorectal cancer, ovarian carcinoma, mesothelioma, melanoma, breast cancer, brain cancer (e.g., glioblastoma), prostate cancer, cervical cancer, non-small cell lung cancer, renal carcinoma, hepatic cancer, pancreatic cancer, biliopancreatic cancer, adenocarcinoma of the liver, gastric cancer, liver cancer, peritoneal cancer, pleural cancer, hematopoietic cancer, and metastatic cancer.

In certain embodiments, treatment by administration of isolated OV-induced T cells or by using a modified virus can be used alone or in combination with one or immunomodulatory agents. An immunomodulatory agent can include any compound, molecule or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and IFNγ, and chemokines, such as MIP-1, MCP-1 and IL-8. In certain embodiments, the immunomodulatory agent includes immune checkpoint inhibitors such as, but not limited to, anti-CTLA4 antibodies, anti-PD-1 antibodies, anti-PDL1 antibodies and TLR agonists (e.g., Poly I:C). In certain embodiments, the checkpoint inhibitors can include molecules and/or compounds that inhibit and/or reduce PD-1, PD-L1 and/or CTLA4 activity and/or function. In certain embodiments, the immunomodulatory agent can be administered systemically or locally.

"In combination with," as used herein, means that a virus, such as an oncolytic vaccinia virus as described herein or a pharmaceutical composition thereof, and the additional therapy, are administered to a subject as part of a treatment regimen or plan. In certain embodiments, being used in combination does not require that the oncolytic virus and the one or more agents are physically combined prior to administration or that they be administered over the same time frame. For example, and not by way of limitation, the oncolytic virus and the one or more agents can be administered concurrently to the subject being treated, or can be administered at the same time or sequentially in any order or at different points in time. In certain embodiments, methods of the present disclosure can include the administration of immunomodulatory agent prior to administration of an oncolytic virus, e.g., an oncolytic virus that comprises a nucleic acid that encodes an immunomodulatory molecule, e.g., IL-2. For example, but not by way of limitation, the immunomodulatory agent can be IL-2, e.g., administered systemically or locally. In certain embodiments, the methods of the presently disclosed subject matter can include promoting an initial immune response in the subject to be treated by administering an oncolytic virus, disclosed herein, e.g., an oncolytic virus that comprises a nucleic acid that encodes an immunomodulatory molecule, e.g., IL-2, and/or the administration of immunomodulatory agent, e.g., IL-2.

In certain embodiments, the methods of the presently disclosed subject matter can comprise administering one or more isolated OV-induced T cells, a virus as disclosed herein or a pharmaceutical composition thereof, followed by, preceded by or in combination with one or more additional therapies. Non-limiting examples of the such therapies can include chemotherapy, radiation, oncolytic viral therapy with an additional virus, treatment with immunomodulatory proteins, an anti-cancer agent or any combinations thereof. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof.

Certain non-limiting embodiments of the presently disclosed subject matter provide for methods of treating cancer where the cancer is an early stage cancer. Certain non-limiting embodiments of the presently disclosed subject matter provide for methods of treating cancer as set forth above where the cancer is not an early stage cancer. For example, but not by way of limitation, the cancer can be a late stage cancer. In certain embodiments, late stage cancer can refer to a cancer that is no longer be limited to the organ of origin: e.g., it may have locally extended beyond the organ of origin or may have metastasized to another site in the body. In certain embodiments, a late stage cancer can be a Grade III cancer. In certain non-limiting embodiments, the presently disclosed subject matter can be used to treat locally invasive or metastatic forms of cancer.

In certain embodiments, the presently disclosed subject matter can be applied to treatment of colon cancer that is stage T3 or higher and/or M1 or higher. In certain embodiments, the presently disclosed subject matter can be applied to treatment of ovarian cancer that is stage 1C or higher. In another certain non-limiting embodiment, the presently disclosed subject matter can be applied to the treatment of mesothelioma that is stage 2 or stage 3 or higher. In certain embodiments, the presently disclosed subject matter can be applied to the treatment of melanoma that is Stage III or higher.

5.6.1. Adoptive T-Cell Immunotherapy

The presently disclosed subject matter provides for methods of treating a subject suffering from a cancer with isolated OV-induced T cells. In certain embodiments, the OV-induced T cells are produced as described above in section 5.5. above. In certain embodiments, the OV-induced T cells can be transferred to the subject from which the cells were isolated. Alternatively and/or additionally, the OV-induced T cells can be transferred to a different subject.

The presently disclosed subject matter provides for an adoptive T-cell immunotherapy, comprising isolating the OV-induced T cells, expanding them ex vivo, and transferring them back to a subject suffering from a cancer. Methods for adoptive T cell transfer are disclosed in US 2003/0170238, the contents of which are incorporated herein by reference.

In certain embodiments, the method of treating a subject suffering from a cancer comprises administering a therapeutically effective amount of OV-induced T cells to the subject. In certain embodiments, the OV-induced T cells were isolated from a different subject. In certain embodiments, the OV-induced T cells were isolated from the subject that is to be treated with the OV-induced T cells.

In certain embodiments, the method of treating a subject suffering from a cancer comprises administering, to the subject, an effective amount of an oncolytic virus, inducing the elicitation of potent antitumor T cells, promoting the trafficking of the induced potent antitumor T cells into the tumor tissues to generate OV-induced T cells, isolating the OV-induced T cells and administering the isolated OV-induced T cells to the subject.

In certain embodiments, the method of treating a subject suffering from a cancer comprises (a) administering, to the subject, an effective amount of an oncolytic virus; (b)

isolating OV-induced T cells; (c) expanding the tumor-infiltrated T cells; and (d) transferring the tumor-infiltrated T cells to the subject suffering from cancer.

In certain non-limiting embodiments, the isolated OV-induced T cells treated with one or more cytokines and/or one or more agents and expanded ex vivo, as described above, are then introduced, e.g., intraperitoneally (i.p.), into a cancer patient. In certain embodiments, the isolated OV-induced T cells are administered intratumorally in a cancer patient.

Non-limiting examples of oncolytic viruses for use in the disclosed methods are described above. For example, but not by way of limitation, the oncolytic virus can be a herpes simplex virus, a vaccinia virus, an adenovirus or a vesicular stomatitis virus. In certain embodiments, the oncolytic virus can be the Western Reserve strain of vaccinia virus. In certain embodiments, the oncolytic virus is the vvDD vaccinia virus. In certain embodiments, the oncolytic virus is a vaccinia virus, e.g., vvDD. In certain non-limiting embodiments, the oncolytic virus can comprise, in its genome, a nucleic acid, encoding an immunomodulator molecule. In certain embodiments, the presently disclosed subject matter relates to oncolytic vaccinia viruses encoding, in expressible form, at least one secreted and/or at least one membrane-associated immunomodulator molecule comprising an immunomodulator molecule linked to a membrane attachment domain, e.g., anchoring peptide, as described above. In certain embodiments, the immunomodulator molecule can be IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, CXCL11, CCL5, an IFN, IFN-alpha, IFN-alpha2, IFN-beta, IFN-gamma, a TNF, TNF-alpha, TNF-beta, GM-CSF or a combination thereof. In certain embodiments, the immunomodulator molecule is IL-2. In certain embodiments, the immunomodulator molecule is IL-23. In certain embodiments, the immunomodulator molecule is TNF-alpha. In certain embodiments, the immunomodulator molecule is CXC11. In certain embodiments, the immunomodulator molecule is CCL5. In certain embodiments, the immunomodulator molecule is IL-15. In certain embodiments, the oncolytic virus, e.g., vaccinia virus, can comprise a nucleic acid that encodes IL-2. In certain embodiments, the oncolytic virus is a Western Reserve strain of vaccinia virus that comprises a nucleic acid that encodes IL-2. In certain embodiments, the oncolytic virus is the vvDD vaccinia virus that comprises a nucleic acid that encodes IL-2. In certain embodiments, the oncolytic virus, e.g., vaccinia virus, can comprise a nucleic acid that encodes IL-2 linked to an anchoring peptide. In certain embodiments, the oncolytic virus is a Western Reserve strain of vaccinia virus that comprises a nucleic acid that encodes IL-2 linked to an anchoring peptide. In certain embodiments, the oncolytic virus is the vvDD vaccinia virus that comprises a nucleic acid that encodes IL-2 linked to an anchoring peptide. In certain embodiments, the IL-2 is linked to the anchoring peptide via a rigid linker. For example, and not by way of limitation, the oncolytic virus is a Western Reserve strain of vaccinia virus that comprises a nucleic acid that encodes IL-2 linked to an anchoring peptide via a rigid linker, e.g., a linker comprising the (A(EA$_3$K)$_4$AAA) linker. In certain embodiments, the oncolytic virus is the vvDD vaccinia virus that comprises a nucleic acid that encodes IL-2 linked to an anchoring peptide via a rigid linker, e.g., a linker comprising the (A(EA$_3$K)$_4$AAA) linker.

In certain non-limiting embodiments, prior to the T cell transfer, cancer patients can be administered another cancer therapy, disclosed above. In certain non-limiting embodiments, after to the T cell transfer, cancer patients can be administered another cancer therapy, disclosed above. For example, and not by way of limitation, the cancer therapies can include chemotherapy, biological therapy, radiotherapy, immunotherapy, hormone therapy, anti-vascular therapy, cryotherapy, toxin therapy and/or surgery or combinations thereof. In certain non-limiting embodiments, a cancer patient can be administered one or more exogenous cytokines and one or more agents, e.g., immunomodulatory agents, prior to the T-cell transfer. In certain non-limiting embodiments, a cancer patient can be administered one or more exogenous cytokines and one or more agents after the T-cell transfer. In certain embodiments, the cytokines and/or agents can be locally or systemically administered. In certain embodiments, the cytokines and/or agents are locally administered. For example, and not by way of limitation, a cancer patient can receive exogenous IL-2 before and/or after T cell transfer.

For example, and not by way of limitation, a cancer patient can receive exogenous IL-2 after T cell transfer.

In certain embodiments, the subject administered the OV-induced T cells of the presently disclosed subject matter can undergo radiation therapy prior and/or after to administration of the OV-induced T cells. For example, and not by way of limitation, the radiation dose can be about 100 Rads (1 Gy) to about 500 Rads (5 Gy), about 5,000 Rads (50 Gy) to about 100,000 Rads (1000 Gy), or about 50,000 Rads (500 Gy), or other appropriate doses within the recited ranges. "Gy" as used herein can refer to a unit for a specific absorbed dose of radiation equal to 100 Rads. Gy is the abbreviation for "Gray."

5.6.2. Treatment With Armed Oncolytic Viruses

The presently disclosed subject matter further provides for methods of treating a subject suffering from a cancer, comprising administering, to the subject, an effective amount of an oncolytic virus, e.g., an armed oncolytic virus, disclosed herein. Non-limiting examples of oncolytic viruses, e.g., armed oncolytic viruses, for use in the presently disclosed methods are disclosed above in sections 5.1., 5.3., and 5.5. above. Methods of administering oncolytic viruses is disclosed above in section 5.4 above.

In certain embodiments, the oncolytic virus can be a herpes simplex virus, a vaccinia virus, an adenovirus or a vesicular stomatitis virus that comprises, in its genome, a nucleic acid encoding an immunomodulator molecule as described herein. In certain embodiments, the oncolytic virus can be the Western Reserve strain of vaccinia virus that comprises, in its genome, a nucleic acid encoding an immunomodulator molecule as described herein. In certain embodiments, the oncolytic virus is the vvDD vaccinia virus that comprises, in its genome, a nucleic acid encoding an immunomodulator molecule as described herein. In certain embodiments, the oncolytic encodes, in expressible form, at least one secreted immunomodulator molecule and/or at least one membrane-associated immunomodulator molecule, as described above. In certain embodiments, the immunomodulator molecule can be IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, CXCL11, CCL5, an IFN, IFN-alpha, IFN-alpha2, IFN-beta, IFN-gamma, a TNF, TNF-alpha, TNF-beta, GM-CSF or a combination thereof. In certain embodiments, the immunomodulator molecule is IL-2. In certain embodiments, the immunomodulator molecule is IL-23. In certain embodiments, the immunomodulator molecule is TNF-alpha. In certain embodiments, the immunomodulator molecule is CXC11. In certain embodiments, the immunomodulator molecule is CCL5. In certain embodiments, the immunomodulator molecule is IL-15. In certain embodiments, the oncolytic virus, e.g., vaccinia virus, can comprise a nucleic acid that encodes IL-2. In certain embodiments, the oncolytic virus is a Western Reserve strain of vaccinia virus that comprises a nucleic acid that encodes IL-2. In certain embodiments, the vvDD vaccinia virus that comprises a nucleic acid that encodes IL-2. In certain embodiments, the oncolytic virus, e.g., vaccinia virus, can comprise a nucleic acid that encodes IL-2 linked to an anchoring peptide. In certain embodiments, the oncolytic virus is a Western Reserve strain of vaccinia virus that comprises a nucleic acid that encodes IL-2 linked to an anchoring peptide. In certain embodiments, the IL-2 is linked to the anchoring peptide via a rigid linker. For example, and not by way of limitation, the oncolytic virus is a Western Reserve strain of vaccinia virus that comprises a nucleic acid that encodes IL-2 linked to an anchoring peptide via a rigid linker, e.g., a linker comprising the (A (EA$_3$K)$_4$AAA) linker (SEQ ID NO:36). In certain embodiments, the oncolytic virus is the vvDD vaccinia virus that comprises a nucleic acid that encodes IL-2 linked to an anchoring peptide via a rigid linker, e.g., a linker comprising the (A(EA$_3$K)$_4$AAA) linker (SEQ ID NO:36).

The presently disclosed subject matter provides for methods of treating a subject suffering from a cancer, comprising administering, to the subject, an effective amount of an armed oncolytic virus, e.g., an oncolytic virus encoding, in expressible form, an immunomodulator molecule, as described above. In certain embodiments, the administration of the oncolytic virus results in the secretion of the immunomodulator molecule from cells infected with the virus. In certain embodiments, the immunomodulator molecule is IL-2.

The presently disclosed subject matter provides for methods of treating a subject suffering from a cancer, comprising administering, to the subject, an effective amount of an oncolytic virus encoding, in expressible form, a membrane-associated protein comprising an immunomodulator molecule linked to an anchoring peptide, as described above. In certain embodiments, the immunomodulator molecule is IL-2.

In certain embodiments, the presently disclosed subject matter provides methods of inhibiting the growth and/or proliferation of and/or promoting the death of a cancer cell of a subject comprising administering to the subject a therapeutically effective amount of an oncolytic vaccinia virus described herein.

In certain embodiments, the presently disclosed subject matter provides methods of inhibiting the growth of a tumor of a subject comprising administering to the subject a therapeutically effective amount of an oncolytic vaccinia virus described herein.

The present invention further provides a method of reducing or inhibiting the growth of a tumor comprising administering to the tumor and/or contacting the tumor with a therapeutically effective amount of an oncolytic vaccinia virus described herein.

In certain embodiments, the presently disclosed subject matter provides methods for lengthening the period of survival of a subject having a cancer comprising administering to the subject a therapeutically effective amount of an oncolytic vaccinia virus described herein. In certain embodiments, the period of survival of the subject having cancer is lengthened by about 1 month, about 2 months, about 4 months, about 6 months, about 8 months, about 10 months, about 12 months, about 14 months, about 18 months, about 20 months, about 2 years, about 3 years, about 5 years or more.

In certain embodiments, the presently disclosed subject matter further provides methods of treating a subject suffering from a cancer, comprising administering, to the subject, an effective amount of an oncolytic virus encoding, in expressible form, an immunomodulator molecule, which can be secreted from infected cells, and inducing the elicitation of potent antitumor T cells.

The presently disclosed subject matter also provides for methods of treating a subject suffering from a cancer, comprising administering, to the subject, an effective amount of an oncolytic virus encoding, in expressible form, a membrane-associated protein comprising an immunomodulator molecule linked to a heterologous anchoring peptide as described above, promoting the trafficking of the induced potent antitumor T cells into the tumor tissues where they would exert their cytotoxicity to cancer cells and associated stromal cells, thus displaying antitumor functions.

The presently disclosed subject matter also provides for methods of treating a subject suffering from a cancer, comprising administering, to the subject, an effective amount of an oncolytic virus encoding, in expressible form, a membrane-associated protein comprising an immunomodulator molecule linked to an anchoring peptide as described above, inducing the elicitation of potent antitumor T cells, and promoting the trafficking of the induced potent antitumor T cells into the tumor tissues where they would exert their cytotoxicity to cancer cells and associated stromal cells, thus displaying antitumor functions.

Certain non-limiting embodiments of the presently disclosed subject matter provide for methods of treating cancer as set forth above where the cancer is an early stage cancer. Certain non-limiting embodiments of the presently disclosed subject matter provide for methods of treating cancer as set forth above where the cancer is not an early stage cancer. Certain non-limiting embodiments of the presently disclosed subject matter provide for methods of treating cancer as set forth above where the cancer is a late stage cancer.

In certain embodiments, the presently disclosed subject matter provides for methods of treating cancer when there is increased tumor burden and/or edema in liver and/or kidneys, increased presence of immunosuppressive CD4$^+$ Foxp3$^+$, CD4$^+$PD-1$^+$ and CD8$^+$PD-1$^+$ T cells, G-MDSC and PD-L1$^+$ cells, and/or decreased presence of NK cells, or when there is increased PD-1, PD-L1, TGF-β and VEGF expression in the tumor microenvironment, compared with the early-stage cancer.

In certain embodiments, the administration of an effective amount of an oncolytic virus results in increased levels of IFN-γ, Granzyme B, perforin and TGF-β, IL-10 and/or decreased levels of angiogenesis markers, e.g., CD105 and VEGF, in tumors that received an oncolytic virus encoding, in expressible form, a membrane-associated protein comprising an immunomodulator molecule linked to an anchoring peptide as described above, compared with tumors received the oncolytic virus encoding, in expressible form, a membrane-associated protein comprising an immunomodulator molecule that can be secreted.

In certain embodiments, the recently disclosed subject matter provides for methods of treating a subject suffering from a cancer, comprising administering, to the subject, an effective amount of an oncolytic virus, described herein, optionally in combination with a checkpoint inhibitor, e.g., an anti-PD-1 antibody, an anti-PD-L1 antibody and/or an anti-CTLA-4 antibody.

In certain embodiments, the recently disclosed subject matter provides for methods of treating a subject suffering from a cancer, comprising administering, to the subject, an effective amount of an oncolytic virus, described herein, optionally in combination with an anti-PD-1 antibody, an anti-PD-L1 antibody and/or an anti-CTLA-4 antibody. For example, and not by way of limitation, a method disclosed herein can include administering, to the subject, an effective amount of an oncolytic virus that comprises a nucleic acid that encodes IL-2 in combination with an anti-PD-1 antibody or an anti-PD-L1 antibody. In certain embodiments, a method disclosed herein can include administering, to the subject, an effective amount of an oncolytic virus that comprises a nucleic acid that encodes IL-2 in combination with an anti-CTLA-4 antibody. In certain embodiments, the method of treating a subject suffering from a cancer, comprising administering, to the subject, an effective amount of a Western Reserve strain of vaccinia virus that comprises a nucleic acid that encodes IL-2, in combination with an anti-PD-1 antibody, an anti-PD-L1 antibody and/or an anti-CTLA-4 antibody.

In certain embodiments, the presently disclosed subject matter also provides for methods of treating a subject suffering from a cancer, comprising administering, to the subject, an effective amount of an oncolytic virus encoding, in expressible form, a membrane-associated protein comprising an immunomodulator molecule linked to an anchoring peptide as described above, in combination an anti-PD-1 antibody, an anti-PD-L1 antibody and/or an anti-CTLA-4 antibody. For example, and not by way of limitation, a method disclosed herein can include administering, to the subject, an effective amount of an oncolytic virus that comprises a nucleic acid encoding a membrane-associated protein comprising IL-2 linked to an anchoring peptide in combination with an anti-PD-1 antibody or an anti-PD-L1 antibody. In certain embodiments, a method disclosed herein can include administering, to the subject, an effective amount of an oncolytic virus that comprises a nucleic acid encoding a membrane-associated protein comprising IL-2 linked to an anchoring peptide in combination with an anti-CTLA-4 antibody. In certain embodiments, the method of treating a subject suffering from a cancer, comprising administering, to the subject, an effective amount of a Western Reserve strain of vaccinia virus that comprises a nucleic acid that encodes IL-2 linked to an anchoring peptide, in combination with an anti-PD-1 antibody, an anti-PD-L1 antibody and/or an anti-CTLA-4 antibody. In certain embodiments, the IL-2 is linked to the anchoring peptide via a rigid linker. For example, and not by way of limitation, the oncolytic virus is a Western Reserve strain of vaccinia virus that comprises a nucleic acid that encodes IL-2 linked to an anchoring peptide via a rigid linker, e.g., a linker comprising the (A(EA$_3$K)$_4$AAA) linker (SEQ ID NO:36).

In certain embodiments, methods of the presently disclosed subject matter can include depletion of Natural killer (NK) cells, CD8+ T cells and/or T cells. In certain embodiments, methods of the presently disclosed subject matter can include neutralization of circulating IFN-γ. For example, but not by way of limitation. a method of the presently disclosed subject matter can include administering to a subject an oncolytic virus, as disclosed herein, and the depletion of CD8$^+$ T cells, NK cells and/or CD4$^+$ T within the subject and/or the neutralization of circulating IFN-γ within the subject. In certain embodiments, depletion and/or neutralization can be obtained by using antibodies, e.g., antibodies to CD8, CD4, NK1.1 and/or IFN-γ. In certain embodiments, a method for treating a subject suffering from a cancer can comprise administering, to the subject, an effective amount of an oncolytic virus that comprises a nucleic acid that encodes IL-2 and the deletion of NK cells. For example, and not by way of limitation, the method can include administering, to the subject, an effective amount of a Western Reserve strain of vaccinia virus that comprises a nucleic acid that encodes IL-2 and the deletion of NK cells, e.g., by the administration of an anti-NK1.1 antibody. In certain embodiments, a method for treating a subject suffering from a cancer can comprise administering, to the subject, an effective amount of an oncolytic virus that comprises a nucleic acid encoding a membrane-associated protein comprising an immunomodulator linked to an anchoring peptide and the deletion of NK cells. In certain embodiments, a method disclosed herein can include administering, to the subject, an effective amount of an oncolytic virus that comprises a nucleic acid encoding a membrane-associated protein comprising IL-2 linked to an anchoring peptide and the deletion of NK cells. For example, and not by way of limitation, the method can include administering, to the subject, an effective amount of a Western Reserve strain of vaccinia virus that comprises a nucleic acid that encodes a membrane-associated protein comprising IL-2 linked to an anchoring peptide and the deletion of NK cells, e.g., by the administration of an anti-NK1.1 antibody.

In certain embodiments, the subject suffers from an early stage cancer. In certain embodiments, the cancer is not an early stage cancer. In certain embodiments, the subject suffers from a late stage cancer.

5.7. Pharmaceutical Compositions

The present disclosure further provides pharmaceutical compositions that include one or more isolated OV-induced T cells isolated from cancer tissue.

The present disclosure further provides pharmaceutical compositions comprising the modified viruses disclosed herein. In certain embodiments, the pharmaceutical compositions containing a modified virus, such as an oncolytic vaccinia virus, as described herein, can be prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

Pharmaceutical compositions are formulated relative to the particular administration route. For example, and not by way of limitation, pharmaceutical compositions that can be administered parenterally, intravenously, intradermally, intramuscularly, transdermally or intraperitoneally are described in U.S. Pat. Nos. 5,543,158, 5,641,515 and 5,399, 363, the contents of which are incorporated by reference herein in their entireties.

In certain embodiments, a pharmaceutical composition as described herein can comprise a pharmaceutically acceptable carrier, e.g., an excipient. "Pharmaceutically acceptable," as used herein, includes any carrier which does not interfere with the effectiveness of the biological activity of the active ingredients and/or that is not toxic to the patient to whom it is administered. an excipient. An excipient can be an excipient described in the Handbook of Pharmaceutical Excipients, American Pharmaceutical Association (1986).

Non-limiting examples of suitable excipients can include a buffering agent, a preservative, a stabilizer, a binder, a compaction agent, a lubricant, a chelator, a dispersion enhancer, a disintegration agent, a flavoring agent, a sweetener and a coloring agent.

In certain embodiments, an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

5.8 Kits

The present disclosure further provides kits that comprise one or more of the disclosed oncolytic viruses described herein. In embodiments, this disclosure provides for a kit for administering a modified virus as described herein. In certain embodiments, a kit of this disclosure can include a modified virus or a pharmaceutical composition comprising a modified virus as described above. In embodiments, this disclosure provides for a kit comprising one or more OV-induced T cells. In certain embodiments, a kit of this disclosure can further include one or more components such as instructions for use, devices and additional reagents, and components, such as tubes, containers and syringes for performing the methods disclosed above.

In certain embodiments, a kit of this disclosure can include instructions for use, a device for administering the modified virus to a subject, or a device for administering an additional agent or compound to a subject. For example, and not by way of limitation, the instructions can include a description of the modified virus and, optionally, other components included in the kit, and methods for administration, including methods for determining the proper state of the subject, the proper dosage amount and the proper administration method for administering the modified virus. Instructions can also include guidance for monitoring the subject over duration of the treatment time.

In certain embodiments, a kit of this disclosure can include a device for administering the modified virus to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, a modified virus to be delivered systemically, for example, by intravenous injection, can be included in a kit with a hypodermic needle and syringe.

In certain embodiments, this disclosure provides a kit for isolating tumor infiltrated T cells—induced by oncolytic virus ("OV-induced T cells") from a subject with cancer after administering a modified virus as described herein. The present disclosure further provides kits that comprise isolated OV-induced T cells expanded according to the methods described herein. In certain embodiments, the OV-induced T cells are cryogenically frozen. Alternatively and/or additionally, the OV-induced T cells are provided in culture medium. In certain embodiments, the kit can provide isolated T cells and further provide for dendritic cells and cancer cells, and/or one or more cytokines and/or one or more agents to treat T cells, including, for example, IL-1, IL-2, IL-3, IL-4, IL-5, IL-6, IL-7, IL-8, IL-9, IL-10, IL-11, IL-12, IL-13, IL-15, IL-17, IL-18, IL-21, IL-23, IL-24, IL-27, IFN-alpha, IFN-alpha2, IFN-beta, or IFN-gamma, TNF-alpha, TNF-beta, and GM-CSF.

In certain embodiments, a kit of the present disclosure can include one or more additional agents that can be administered in combination with an oncolytic virus and/or isolated OV-induced T cells. For example, but not by way of limitation, a kit can include a cytokine, e.g., IL-2, and/or an anti-PD-1 and/or an anti-PD-L1 antibody.

In certain embodiments, a kit of this disclosure can provide a device for isolating T cells from a subject after administering the modified virus to the subject, or a device for transferring the treated T cells into a subject. For example, and not by way of limitation, a kit of this disclosure can provide instructions including a description of isolating OV-induced T cells and methods for transferring the treated T cells into a patient, including methods for determining the proper state of the subject, the proper dosage amount and the proper administration method for transferring the treated T cells. In certain embodiments, a kit of this disclosure can include instructions for use, a device for administering the modified virus to a subject, and/or a device for administering an additional agent or compound to a subject, and/or a device for isolating the OV-induced T cells. For example, and not by way of limitation, the instructions can include a description of the modified virus and, optionally, other components included in the kit, and methods for administration, including methods for determining the proper state of the subject, the proper dosage amount and the proper administration method for administering the modified virus. Instructions can also include a description of isolating the OV-induced T cells, methods of treating the isolated T cells, and methods of transferring the treated T cells into a patient. Instructions can also include guidance for monitoring the subject over duration of the treatment time.

6. EXAMPLE 1: ONCOLYTIC VACCINIA VIRUS EXPRESSING MEMBRANE-ATTACHED IL-2 DISPLAYED POTENT ANTITUMOR EFFICACY AND REDUCED TOXICITY

An oncolytic vaccinia virus, vvDD (or VVDD), as described in U.S. Pat. No. 7,208,313, the disclosure of which is incorporated by reference herein in its entirety, was engineered to express murine IL-2 ("mIL-2") by inserting an mIL-2 encoding nucleic acid, under the control of the vaccinia p7.5 e/l promoter, in the viral tk gene, to produce virus denoted "vvDD-mIL-2," which results in the secretion of mIL-2 from infected cells. The antitumor efficacy of this IL-2-armed virus was tested in mouse models of colon cancer, ovarian cancer, and mesothelioma, created by inoculating mice with MC38-luc, ID8-luc, or AB12-luc tumor cells, respectively, where the cells are labeled with luciferase ("luc") to enable monitoring of tumor development. Using an experimental scheme shown in FIG. 1A, 5.0 e5 tumor cells were inoculated subcutaneously on day 0, and then, on day 5, mice were administered either PBS or 1.0 e8 pfu of vvDD-IL-2 or, as a control, vvDD unarmed with mIL-2. The number of mice in each test group was 10+/−4. Survival of the mice was monitored and the results are shown in FIGS. 1B-D; in each case vvDD-mIL-2 prolonged survival substantially relative to the controls.

However, if tumors were allowed to progress in the mice prior to virus treatment, survival of vvDD-mIL-2 treated mice was poorer than controls. As shown in FIG. 2A, when mIL-2-armed virus was administered nine days after MC38-luc (colon cancer) tumor cell inoculation, the recipient mice died within one week (FIG. 2B). As the tumor burden of these mice would be comparable to the control animals in this study, it is inferred that the animals died from toxic effects of secreted IL-2.

To mitigate the potential toxic effects of IL-2, an oncolytic vaccinia virus was engineered to express, in an infected tumor cell, membrane anchored IL-2. FIG. 3A shows a schematic diagram of a portion of the engineered vvDD virus, in which mIL-2 encoding nucleic acid, fused in-frame to nucleic acid encoding a (G45)3 linker and a GPI anchoring peptide having the sequence GPAGGGGSG-GGGSGGGGSVSTISSFSPPGYQVSFCLVMVLL-FAVDTGLYFSVKTN I (SEQ ID NO:16), all operably linked to the p7.5 e/l promoter, is inserted in the tk gene to produce virus denoted "vvDD-mIL-2-GPI". Also disrupting the tk gene is a gene encoding yellow fluorescent protein ("YFP") operably linked to the pSe/l promoter, and transcribed in the opposite direction as mIL-2, to aid in detecting virus-infected cells. When tested in MC38 colon cancer and B16 melanoma cell lines, vvDD-mIL-2-GPI expressed mIL-2 that was mostly retained on the membrane of infected cells, whereas mIL-2 expressed by vvDD-mIL-2 was not, as demonstrated by flow cytometry (FIGS. 4A-B). The infected cells were gated by YFP and then analyzed for IL-2 expression on the gated YFP+ cells. FIG. 5A-B presents the expression intensity of IL-2 on the cell membrane. These data clearly demonstrated that vvDD-mIL-2-GPI expressed a lot more membrane-anchored IL-2 on the infected cancer cells.

FIG. 6 shows the results of an experiment comparing "unarmed" vvDD (parental virus) with vvDD-mIL-2 and vvDD-mIL-2-GPI. Mice were administered either PBS or (unarmed) vvDD, vvDD-mIL-2, or vvDD-mIL-2-GPI (at a dose of 1.0 e8 pfu) 5 days after tumor cell inoculation. As shown in FIG. 6, PBS control-treated mice died within about 20 days after tumor cell inoculation and most mice treated with unarmed vvDD died within about 30 days of tumor inoculation (all mice in this group died by 43 days), but after 50 days all mice treated with vvDD-mIL-2 were still alive and more than 80 percent of mice treated with vvDD-mIL-2-GPI were alive, indicating that the "anchored" IL-2 retained beneficial IL-2 function (n=8).

FIG. 7 compares IL-2-related toxic effects in mice treated with 2.0 e8 pfu (2.0×10$^8$ pfu) of either vvDD-mIL-2 or vvDD-mIL-2-GPI 9 days after inoculation with MC38-luc cells. Five days after viral treatment, more than 80 percent of mice treated with vvDD-mIL-2 had died, whereas all vvDD-mIL-2-GPI-treated mice survived (n=13-15).

7. EXAMPLE 2: ADOPTIVE TRANSFER OF TUMOR INFILTRATED T CELLS—INDUCED BY ONCOLYTIC VIRUS ("OV-INDUCED T CELLS") LED TO SIGNIFICANT THERAPEUTIC EFFECTS IN SYNGENEIC C57BL/6 MICE BEARING PERITONEAL MC38 TUMOR

This Example provides studies of oncolytic vaccinia viruses expressing membrane-associated forms of immunostimulatory cytokines.

B6 mice were intraperitoneally inoculated with 5×10$^5$ MC38-luc cancer cells and divided into required groups according to tumor growth condition based on live animal IVIS imaging 7 days post tumor cell injection. Grouped mouse were intraperitoneally injected with 5×10$^6$ T cells per 100 μl or 100 μl PBS as a control. T cells were generated by intratumoral vvDD-IL-2-GPI (1.0 e8 pfu) injection into MC38 s.c. tumor bearing mouse. Ten days post virus-treatment tumors were harvested and T-cells were separated using CD90.2 beads (Miltenyi Biotec, CA, USA). T-cells were co-cultured with αDC-MC38 for 2 days. On day 2, IL-2 (4 ng/ml) and IL-7 (5 ng/ml) or additionally GSK3b-inhibitor (7 μM) were added. On day 5, T-cells have been transferred intraperitoneal (i.p.) injection into MC38-luc tumor bearing mouse. Prior to T cell transfer, treated mouse received 5Gy of sublethal irradiation to mimic lymphodepletion similar to clinical protocols. All treated mouse received exogenous cytokine support of IL-2 (100.000 IU/mouse i.p. for 3 days every 12 h). FIG. 8A shows the timeline of the experimental setup.

As shown in FIG. 8B, 100% of the tumor-bearing mice survived at least 100 days post-inoculation when administered OV-induced T cells that were treated ex vivo with IL-2, IL-7 and GSK3b-inhibitor and about 50% of the tumor-bearing mice survived at least 100 days post-inoculation when administered OV-induced T cells that were treated ex vivo with IL-2 and IL-7. Live images of the mice with MC38-luc tumors at day 21 post treatment are shown in FIG. 8C and at day 28 post treatment in FIG. 8D. As shown in FIG. 8, oncolytic vaccinia viruses expressing novel forms of immunostimulatory cytokines (such as membrane-associated) can induce potent tumor-specific T cells, and promote the trafficking of such T cells into tumor tissues where they exert their functions against tumor growth. In addition, OV-induced T cells can be isolated and expanded ex vivo under appropriate conditions. When these cultured and expanded tumor-specific T cells were infused back to a second tumor-bearing mice, they displayed potent anti-tumor activity in MC38 colon tumor model in syngeneic mice. The present approach demonstrated that oncolytic virus-elicited and enriched anti-tumor T cells can be utilized for cancer therapy.

8. EXAMPLE 3: DISPLAYING MEMBRANE ASSOCIATED INTERLEUKIN-2 RIGIDLY WITH POTENT EFFICACY AND HIGH SAFETY

8. 1. Introduction

Pleiotropic cytokine interleukin-2 (IL-2) is an established cancer therapeutic agent, whereas its clinical application has been limited for the severe life-threatening side effects followed by the systemic use of high dose of IL-2[1-4]. Considerable efforts have been devoted to developing IL-2 variants, such as IL-2-fusion proteins, IL-2/anti-IL-2 antibody complexes and "superkines," or chemical modified IL-2, to extend in vivo half-life and improve biological activity and safety[5-13]. The present Example discloses a new form of IL-2 immunotherapy through local delivery of a cell membrane associated IL-2 in tumor bed by tumor-targeted oncolytic vaccinia virus. Displaying IL-2 either flexibly or rigidly on the cell membrane cured mice with established early-stage peritoneal colon cancer, an effect similar to delivering secreted IL-2 by vaccinia virus. While secreted IL-2 delivered by vaccinia virus led to high mortality at the late-stage tumor model during the virus replication period, displaying IL-2 rigidly on cell membrane significantly enhanced the survival of mice with late-stage peritoneal colon cancer. Displaying IL-2 rigidly on the cell membrane led to profound changes in the immune status of tumor microenvironment, which made it feasible to combine anti-PD-1/PD-L1 Ab to cure most mice with late-stage peritoneal colon cancer. These findings show that the new form of IL-2 immunotherapy can be translatable to the clinic for cancer treatment.

Virus-delivered secreted IL-2 has been suggested to have the potential to treat established tumors in mouse models (FIG. 1)[14]. To reduce the severe toxic side effects caused by systemic use of high dose of IL-2 and to treat pleural, peritoneal, hematopoietic or metastatic cancer, oncolytic vaccinia virus vvDD was used. Treating pleural, peritoneal, hematopoietic or metastatic cancer by intratumoural virus injection can be difficult. Using oncolytic vaccinia virus which has been approved safe, to deliver membrane-associated IL-2 to treat peritoneal colon cancer, since membrane-associated cytokines have been suggested to retain on membrane without obvious compromised cytokine function[15-17]. An approach using oncolytic vaccinia virus vvDD can result in the use of fewer viruses and can cause less side effects.

8.2 Methods

Mice and Cell Lines.

Female C57BL/6 (B6 in short) and BALB/c mice were purchased from The Jackson Laboratory (Bar Harbor, ME) and housed in specific pathogen-free conditions in the University of Pittsburgh animal facility. All animal studies were approved by the Institutional Animal Care and Use Committee. Mouse colon cancer MC38-luc, ovarian cancer ID8-luc, mesothelioma AB12-luc were generated as described previously[31]. Mouse melanoma B16 was obtained from ATCC. All cell lines were grown in Dulbecco's modified Eagle's medium (DMEM) supplemented with 10% fetal bovine serum (FBS), 2 mL L-glutamine, penicillin/streptomycin (Invitrogen, Carlsbad, CA) in 37° C., 5% $CO_2$ incubator.

Virus Generation.

vSC20, a vgf gene-deleted Western Reserve (WR) strain VV was used as the parental virus for homologous recombination. The plasmid pCMS1-IRES carrying two multiple cloning sites separated with an IRES sequence from pLVX-IRES-ZsGreen was constructed by us from the shuttle plasmid pSEM-1[32]. pCMS1-IRES was then inserted with fragments containing flexible linker or rigid linker+GPI anchor sequence amplified form human CD16b by PCR, resulting plasmids pCMS1-IRES-FG or pCMS1-IRES-RG, respectively. Murine IL-2 cDNA was inserted into pCMS1-IRES, pCMS1-IRES-FG or pCMS1-IRES-RG to get shuttle plasmids pCMS1-IL-2, pCMS1-IL-2-FG or pCMS1-IL-2-RG. GPI anchor sequence in pCMS1-IL-2-FG was further replaced with murine PD-L1 transmembrane domain to get shuttle plasmid pCMS1-IL-2-FPTM. All these shuttle vectors were used for homologous recombination of murine IL-2 variants into the tk locus of vaccinia viral genome. The primers for plasmid cloning based on PCR were listed in Table 2.

TABLE 2

Primers for plasmid cloning based on PCR

| primer | PCR template | Resulted plasmid |
|---|---|---|
| p1:<br>5'gcgggtcgacatatggcgcc<br>atgcattataaggcgcgcccg<br>cccctctccctccc3'<br>(SEQ ID NO: 19) | pLVX-IRES-ZsGreen | pCMS1-IRES |
| p2:<br>5'ggccgttaacttaagagctc<br>atttaaatcctgcagggccggc<br>cattatcatcgtg3'<br>(SEQ ID NO: 20) | | |
| p3:<br>5'ggccggccggccggtggcgg<br>tgggagcggtggtggggg<br>ttccggaggcggaggg3'<br>(SEQ ID NO: 21) | Human CD16b cDNA | pCMS1-IRES-FGPI |
| p4:<br>5'ggttccggaggcggagggtc<br>ggtgtcaaccatctcatcattc<br>tc3'<br>(SEQ ID NO: 22) | | |
| p5:<br>5'gcgcgttaactcaaatgttt<br>gtcttcacagag3'<br>(SEQ ID NO: 23) | | |
| p6:<br>5'ggccggccggccgctgaagc<br>tgccgcaaaagaggccgctgc<br>gaaggaggccgcggctaag3'<br>(SEQ ID NO: 24) | Human CD16b cDNA | pCMS1-IRES-RGPI |
| p7:<br>5'gaggccgcggctaaggaggc<br>ggcagctaaagctgcagccgtg<br>tcaaccatctcatcattc3'<br>(SEQ ID NO: 25) | | |
| p5:<br>5'gcgcgttaactcaaatgttt<br>gtcttcacagag3'<br>(SEQ ID NO: 26) | | |
| p8:<br>5'ggcggtcgacatgtacagca<br>tgcagctcg3'<br>(SEQ ID NO: 27) | Murine IL-2 cDNA | pCMS1-IL-2-IRES |
| p9:<br>5'ccgcggcgcgccttattgag<br>ggcttgttgag3'<br>(SEQ ID NO: 28) | | |
| p8:<br>5'ggcggtcgacatgtacagca<br>tgcagctcg3'<br>(SEQ ID NO: 29) | Murine IL-2 cDNA | pCMS1-IL-2-FG |
| p10:<br>5'ccgcggccggcccttgaggg<br>cttgttgag3'<br>(SEQ ID NO: 30) | | |
| p8:<br>5'ggcggtcgacatgtacagca<br>tgcagctcg3'<br>(SEQ ID NO: 31) | Murine IL-2 cDNA | pCMS1-IL-2-RG |
| p10:<br>5'ccgcggccggcccttgaggg<br>cttgttgag3'<br>(SEQ ID NO: 32) | | |
| p3:<br>5'ggccggccggccggtggcgg<br>tgggagcggtggtggggg<br>ttccggaggcggaggg3'<br>(SEQ ID NO: 33) | Murine PD-L1 cDNA | pCMS1-IL-2-FPTM |

TABLE 2-continued

Primers for plasmid cloning based on PCR

| primer | PCR template | Resulted plasmid |
|---|---|---|
| p11:<br>5'ccggaggcggtgggtcgcac<br>tgggtgcttctgggatc3'<br>(SEQ ID NO: 34) | | |
| p12:<br>5'cgcgttaactaccccaagaa<br>gaggaggaccgtggacact<br>acaatgaggaacaacaggatg3'<br>(SEQ ID NO: 35) | | |

To make the new virus vvDD-IL-2, vvDD-IL-2-FG, vvDD-IL-2-RG and vvDD-IL-2-FPTM, CV-1 cells were infected with vSC20 at multiplicity of infection (MOI) of 0.1 and then transfected with the shuttle plasmids, resulting in viral seeds. Selection of the new recombinant viruses was based on expression of yellow fluorescent protein in CV1 cells 24 h post seed virus infection. vvDD-YFP, or vvDD in short, a double viral gene-deleted (tk- and vgf-) VV carrying yfp cDNA at the tk locus, is the control virus for this work.

Viral Replication Assays In Vitro.

Tumor cells were seeded at $1.0 \times 10^5$ per well in six-well plates and infected with indicated viruses next day at MOIs of 0.1, 1.0, or 10 in 1 ml medium containing 2% fetal bovine serum for 2 hours. Following infection, cells were added 3 mL medium containing 10% fetal bovine serum and cultured until harvesting at 24, 48, and 72 hours post viral infection. The cell pellet was homogenized using a FastPrep Cell Disrupter (Model FP120; Qbiogene, Carlsbad, CA) to release virions, and the resulting cell lysates were titered on CV-1 cells to determine viral load by plaque assay.

MTS Cytotoxicity Assay In Vitro.

Tumor cells were plated at $1.0 \times 10^4$ cells per well in 96-well plates and infected with indicated viruses next day at MOIs of 0.05, 0.1, 0.5, 1.0, and 5.0. Cell viability was determined at 48 and 72 hours after infection, by CellTiter 96 Aqueous Nonradioactive Cell Proliferation Assay, or MTS assay (Promega, Madison, MI).

Viral Delivered IL-2 Expression In Vitro.

MC38-luc ($3 \times 10^5$), B16 ($2 \times 10^5$) or AB12-luc ($3 \times 10^5$) cells were seeded in 24-well plates overnight and infected with vvDD, vvDD-IL-2, vvDD-IL-2-FG, vvDD-IL-2-RG or vvDD-IL-2-FPTM at MOI of 1 in 0.15 mL 2% FBS-containing-DMEM for 2 h. Cells were added 0.35 mL 10% FBS-containing-DMEM and cultured until harvesting at 24 h post viral infection. The culture supernatants were harvested for measuring IL-2 by ELISA (BD Bioscience, San Jose, CA) and the cell pellets were applied either to measure membrane-associated IL-2 by flow cytometry, or to extract RNA to measure IL-2 expression by RT-qPCR.

Rodent Tumor Models.

B6 mice were intraperitoneally inoculated with $5 \times 10^5$ MC38-luc, $3.5 \times 10^6$ ID8-luc cancer cells or BALB/c mice were intraperitoneally inoculated with $4 \times 10^5$ AB12-luc, respectively, and divided into required groups 5 days or 9 days post tumor cell inoculation according to tumor size based on live animal IVIS imaging, performed using a Xenogen IVIS 200 Optical In Vivo Imaging System (Caliper Life Sciences, Hopkinton, MA). Grouped mice were intraperitoneally injected with indicated viruses, antibodies, the combinations or PBS, respectively. In some experiments, α-CD8 Ab at 250 μg/injection (clone 53-6.7; Bio X Cell), α-CD4 Ab (clone GK1.5, Bio X Cell; 150 μg/injection), α-NK1.1 (clone PK136, Bio X Cell; 300 μg/injection) or α-IFN-γ Ab (clone XMG1.2, Bio X Cell; 200 μg/injection) were intraperitoneally injected into mice to deplete CD8$^+$ T cells, CD4$^+$ T cells, NK1.1$^+$ cells or neutralize circulating IFN-γ. In some experiments, mice were sacrificed to harvest tumor tissues and spleens at indicated time points.

MC38-luc-tumor-bearing B6 mice treated with indicated vaccinia viruses, which survived more than 60 days, were subcutaneously rechallenged with $5 \times 10^5$ MC38-luc cells per mouse. And naïve B6 mice received same dose tumor challenge as a control. The primary tumor size was measured using an electric caliper in two perpendicular diameters.

Assessment of Treatment-Related Toxicity.

Virus-treated mice were sacrificed 4 to 5 days post treatments for collection of blood, lungs, kidneys and spleens. Blood samples were kept for 2 hours at room temperature and separated sera by centrifugation for measuring IL-2 and TNF-α using commercialized kits (BD Biosciences and BioLegend, respectively), according to the vendors' instructions. Water content was used to monitor tissue edema. Briefly, wet tissue was weighed, and dehydrated overnight at 90° C. in chemical hood. The weight difference between wet tissues and dry tissues was calculated.

Flow Cytometry.

Collected tumor tissues were weighed and incubated in RPMI 1640 medium containing 2% FBS, 1 mg/ml collagenase, 0.1 mg hyaluronidase, and 200 U DNase I (All enzymes were from Sigma, St. Louis, MO) at 37° C. for 1-2 h to make single cells. In vitro virus-infected cells or single cells from tumor tissues were blocked with a-CD16/32 Ab (clone 93) and then stained with antibodies against mouse CD45 (APC or PerCP-Cy5.5, clone: 30-F11), CD11b (PE, clone: M1/70), Ly6G (APC, clone: 1A8), Ly6C (clone: HK1.4), F4/80 (FITC, clone: BM8, e-Bioscience), CD4 (APC or FITC, clone: RM4-5, BD Biosciences), Foxp3 (PE, clone: FJK-16s, e-Bioscience), CD8 (APC or PE, clone: 53-6.7), CD44 (FITC, clone: IM7), PD-1 (PE, clone: J43, e-Bioscience), IFN-γ (APC, clone: XMG1.2, e-Bioscience), CD3 (FITC, clone: 17A2, eBioscience), NK1.1 (PE, clone: PK136), PD-L1 (APC, clone: 10F.9G2), IL-2 (APC-SA+ Biotin-IL-2, clone:JES6-5H4). All antibodies without source mentioned were purchased from BioLegend. Samples were collected on BD Accuri C6 cytometer, and data were analyzed using BD Accuri C6 cytometer software.

RT-qPCR.

Total RNA was extracted from virus-infected cells or tumor tissues using the RNeasy Kit (Qiagen, Valencia, CA). One microgram of RNA was used for cDNA synthesis, and 25 to 50 ng of subsequent cDNA was used to conduct mRNA expression analysis by TaqMan analysis on the StepOnePlus system (Life Technologies, Grand Island, NY). All the primers for the analysis were purchased from Thermo Fisher Scientific (Waltham, MA). The gene expression was normalized to a house-keeping gene HPRT1 and expressed as fold increase ($2^{-\Delta CT}$), where $\Delta CT = CT_{(Target\ gene)} - CT_{(HPRT1)}$.

Statistics.

Statistical analyses were performed using Student's t test (GraphPad Prism version 7). Animal survival is presented using Kaplan-Meier survival curves and was statistically analyzed using log rank test (GraphPad Prism version 7). Value of P<0.05 is considered to be statistically significant, and all P values were two sided. In the figures, the standard symbols were used: * P<0.05;  P<0.01; * P<0.001; and **** P <0.0001.

8.3 Results

Viruses vvDD-IL-2, vvDD-IL-2-FPTM, vvDD-IL-2-FG and vvDD-IL-2-RG were generated based on vvDD (FIG. 9). In brief, vvDD-IL-2 produced secreted murine IL-2 and vVDD-IL-2-FPTM, vvDD-IL-2-FG and vvDD-IL-2-RG displayed murine IL-2 on cell membrane post infection. vvDD-IL-2-FPTM produced IL-2 fused with murine PD-L1 transmembrane domain and a flexible linker $(G_4S)_3$ (SEQ ID NO:12) in between. vvDD-IL-2-FG and vvDD-IL-2-RG produced IL-2 fused with glycoinositol phospholipid (GPI) anchor sequence of human CD16b, and a flexible linker $(G_4S)_3$ and a rigid linker $(A(EA_3K)_4AAA)$ (SEQ ID NO:36) in between, respectively. These four viruses have similar capacity of replication and cytotoxicity in tumor cells, compared with parental virus vvDD (FIG. 10). vvDD-IL-2 produced significantly more IL-2 in supernatant than others, but not membrane associated IL-2. vvDD-IL-2-FPTM, vvDD-IL-2-FG and vvDD-IL-2-RG produced few IL-2 in supernatant, but significantly more membrane-associated IL-2 than VVDD-IL-2. The amount of membrane associated IL-2 in vvDD-IL-2-RG was more than vvDD-IL-2-FG and the amount of membrane associated IL-2 in vvDD-IL-2-FG was more than vvDD-IL-2-FPTM (FIG. 11A).

Next, the mRNA levels of IL-2 and viral marker gene A34R were determined in tumor cell post virus infection in vitro. The data showed that viral gene A34R mRNA were similar, but IL-2 mRNA pattern was similar to the pattern of the membrane associated IL-2 amount described above. Without being bound to a particular theory, this shows that the precise component of chimeric proteins can impact the mRNA stability and further impact the amount of IL-2 displaying on cell membrane (FIG. 12).

To evaluate the antitumor efficacy of the four viruses, each virus was injected intraperitoneally at the dose of $2 \times 10^8$ PFU/mouse to treat B6 mice received murine colon cancer cell MC38-luc inoculation 5 days ago (early-stage tumor model). The survival results showed that vvDD-IL-2, vvDD-IL-2-FG and vvDD-IL-2-RG, but not vvDD-IL-2-FPTM, elicited more potent antitumor effects compared with PBS or vvDD (FIG. 11B). Without being bound to a particular theory, this can be explained by the low amount of IL-2 displayed on cell membrane post vvDD-IL-2-FPTM infection (FIG. 11A and FIG. 12). The mice treated with vvDD-IL-2 survived longer than those treated with vvDD-IL-2-FG, but not than those treated with vvDD-IL-2-RG (FIG. 11B).

All the mice that survived the vvDD-IL-2, vvDD-IL-2-FG and vvDD-IL-2-RG treatment rejected a subcutaneous tumor rechallenge, which showed that a systemic antitumor response was elicited (FIG. 13). A few mice died within one week post vvDD-IL-2 treatment (FIG. 11B). Without being bound to a particular theory, this could be a sign of IL-2-induced toxicity. To investigate if secreted IL-2 produced by vvDD-IL-2 treatment can induce systemic toxicity to some degree and be more toxic for mice with heavy tumor burden, the safety and antitumor efficacy of the viruses with the same virus dosage was assessed by switching from an 5-day-tumor-bearing mouse model (early-stage tumor model) to a 9-day-tumor-bearing mouse model (late-stage tumor model), a more immunosuppressive tumor model, in which the mouse has a higher tumor burden, more immunosuppressive CD4+Foxp3+, CD4+PD-1+ and CD8+PD-1+ T cells, G-MDSC and PD-L1+ cells, less NK cells and higher PD-1, PD-L1, TGF-β and VEGF expression in the tumor microenviroment, compared with the early-stage tumor model (FIGS. 14 and 15). The late-stage tumor mice also have increased severe edema in the livers and kidneys (FIG. 15), compared with the early-stage tumor model. The therapeutic results from the late-stage tumor model showed that the vvDD-IL-2 treatment led to a high mortality within one-week post treatment, whereas treatment with the other viruses were safe. The vvDD-IL-2-FG and vvDD-IL-2-RG treatments significantly extended the animal survival, compared with the vvDD treatment, however, the vvDD-IL-2-RG treatment elicited a significantly better survival (FIG. 11C and FIG. 16A).

To further investigate the toxicity induced by the viruses, IL-2 serum levels were measured and it was found that they were 100 times higher in the serum of mice treated with vvDD-IL-2, compared to the serum of mice treated with the other viruses and reached about 24950 pg/mL (FIG. 16B). Low levels of IL-2 were also detected in the serum of mice treated with vvDD-IL-2-FG and vvDD-IL-2-RG. Without being bound to any particular theory, this can be explained due to the more loose association of the GPI-anchored proteins with the cell membrane, compared to transmembrane proteins and could be spontaneously released from the cell membrane due to shedding or proteolytic cleavage and also because free GPI-anchored proteins could also transfer to cell membrane via a process termed "cell surface painting"[18].

To examine if IL-2 can induce an increase in the TNF-α serum levels[19] TNF-α serum levels were measured after vvDD-IL-2 treatment and it was found that vvDD-IL-2 treatment induced a significant increased in the TNF-α serum levels (FIG. 16C). Mice were also assessed for tissue edema, a hallmark for measuring IL-2 induced vascular leak syndrome[20]. Only vvDD-IL-2 treatment induced substantial more pulmonary and hepatic edema, as evidenced by the water content increase in lungs and livers (FIGS. 16D-16E). Tissue edema was also found. Additionally, increased IL-2 serum levels were found in vvDD-IL-2-treated mice, even on the early-stage tumor model (FIGS. 17A-17D). Taken together, these data showed that vvDD-IL-2-FG and vvDD-IL-2-RG treatments were safer than vvDD-IL-2.

Treatments with vvDD-IL-2-FG and vvDD-IL-2-RG have similar therapeutic efficacy in early-stage tumor model. However, only vvDD-IL-2-RG treatment resulted in a substantial better survival in late-stage tumor model, even though both treatments had a similar safety profile. To explore the reason behind this result, the immune cell profile in tumor microenvironment and spleens was investigated using a late-stage tumor model. The percentages of activated CD4+Foxp3− and CD8+IFN-γ+ T cells from tumors that received vvDD-IL-2-RG treatment were higher, compared to tumors that received other virus treatment (FIGS. 18A and 18B). To examine if memory CD8+ T cells and NK cell can readily respond to IL-2[21], memory CD8+CD44$^{hi}$ T cells and CD3−NK1.1+ cells were examined. The percentages of both types of cells from tumors post virus treatment had the same pattern with the activated T cells described above. Similar results were even observed in spleen (FIG. 18C and FIG. 19A-19C).

Figure 19A:
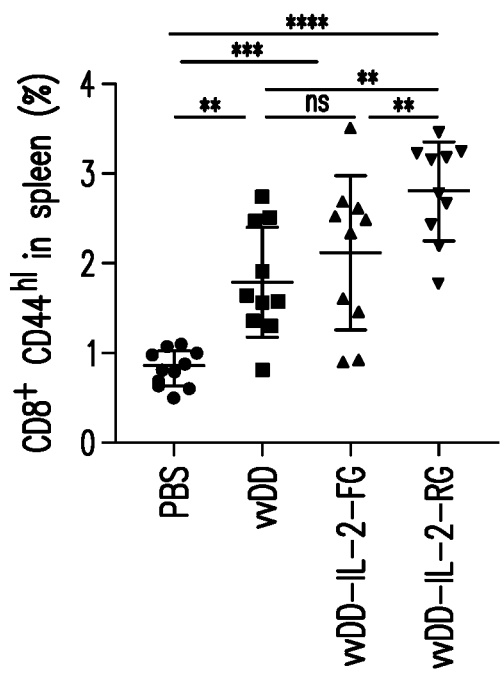
Figure 19B:
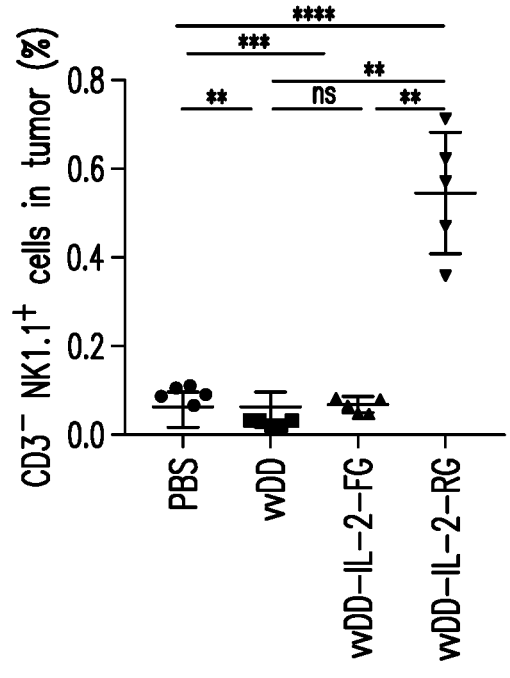
Figure 19C:
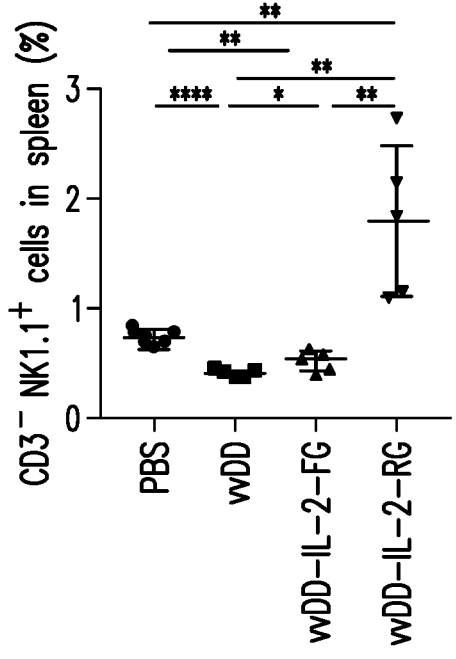
Figure 19D:
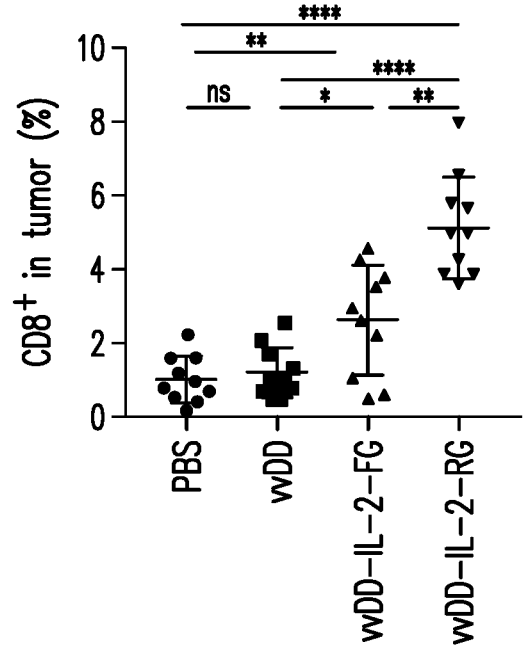

Further, the presence of CD4+Foxp3+ T cells in tumors that received virus treatment were examined. The percentages of CD4+ T regulatory cells in tumors were similar to the ones described above (FIG. 18D). Thus, the CD8+/Treg ratio in tumors that received vvDD-IL-2-RG treatment was significantly higher, since CD8+ T cells were elevated in tumor post vvDD-IL-2-RG treatment compared to tumors that received other virus treatment (FIG. 18E and FIG. 19D).

Next, the expression of protumoral and antitumoral factors was examined in tumors collected from the late-stage tumor model post virus treatment. There was an increased expression of IFN-γ, Granzyme B, perforin, and decreased expression of TGF-β and angiogenesis markers CD105 and VEGF in tumors that received vvDD-IL-2-RG treatment, compared to tumors that received the other virus treatments (FIGS. 18F-18K). Expression of IL-10 was also found to be significantly elevated in tumors received VVDD-IL-2-RG treatment (FIG. 18L). Without being bound to a particular theory, although IL-10 can function as both immune stimulation and immune suppression in cancer, here IL-10 can have an inhibitory effect on the expression TNF-α, which was elevated by IL-2 and recently suggested as a tumor growth factor for minimal residual tumor, thereby making VVDD-IL-2-RG treatment safer and more effective (FIG. 16C)[19,22-24].

To examine if the antitumor effect elicited by vvDD-IL-2-RG treatment was IFN-γ and CD8+ T cell dependent or CD4+ T cell dependent, IFN-γ, CD4+ and CD8+ T cells and NK1.1+ cells were depleted by antibodies post vvDD-IL-2-RG treatment. The results demonstrated that the antitumor effect elicited by vvDD-IL-2-RG treatment was IFN-γ and CD8+ T cell dependent, and not CD4+ T cell dependent (FIG. 18M). The results also demonstrated that the NK cell depletion led to a significantly better survival compared to the vvDD-IL-2-RG treatment alone. Without being bound to a particular theory, the reason could be that the NK cells could impede virotherapy via the natural cytotoxicity receptor NKP46. The expression of NKP46 was significantly increased by the vvDD-IL-2-RG treatment, thus, NK cell depletion could have removed this impediment (FIG. 20)[25].

Collectively, these data demonstrated that vvDD-IL-2-RG treatment turned the immune status in tumor-bearing mice from immune-suppressive to immune-favorable, which finally led to a better survival.

Figure 22A:
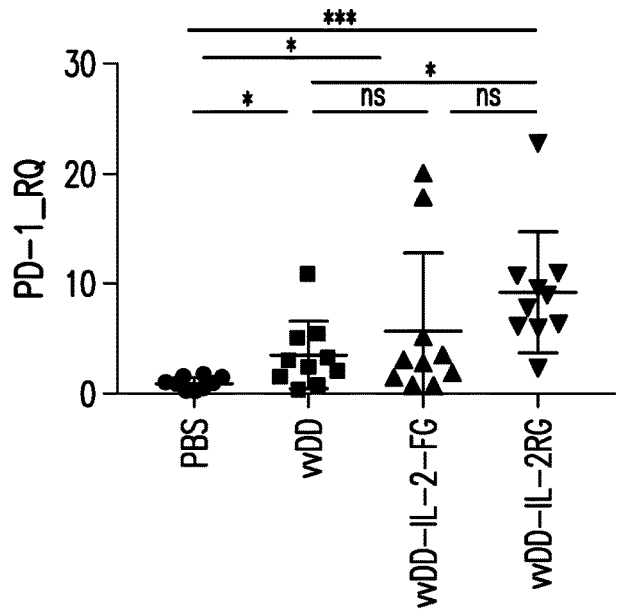
Figure 22B:
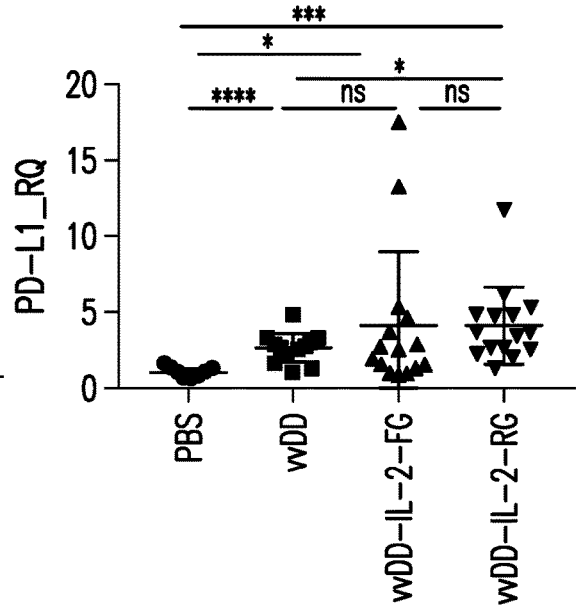
Figure 22C:
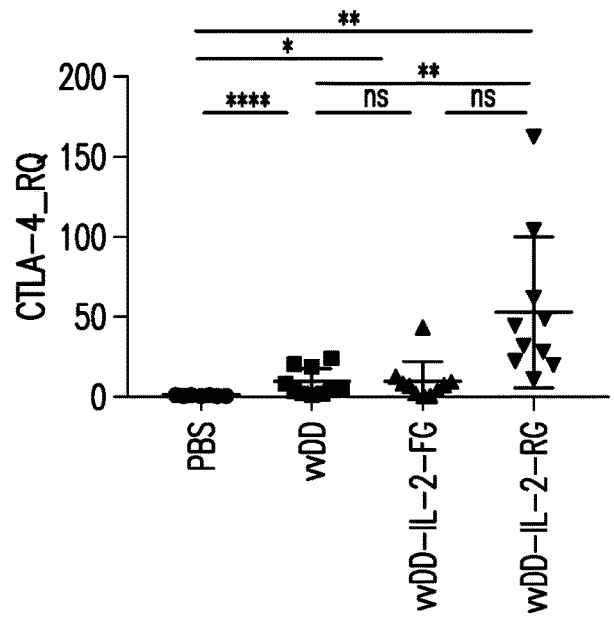
Figure 22E:
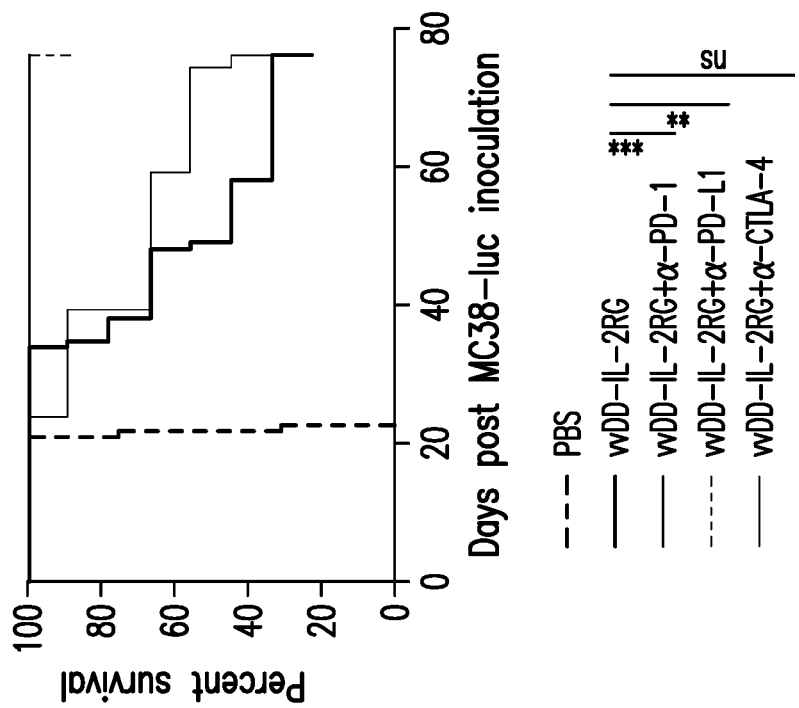
Figure 22D:
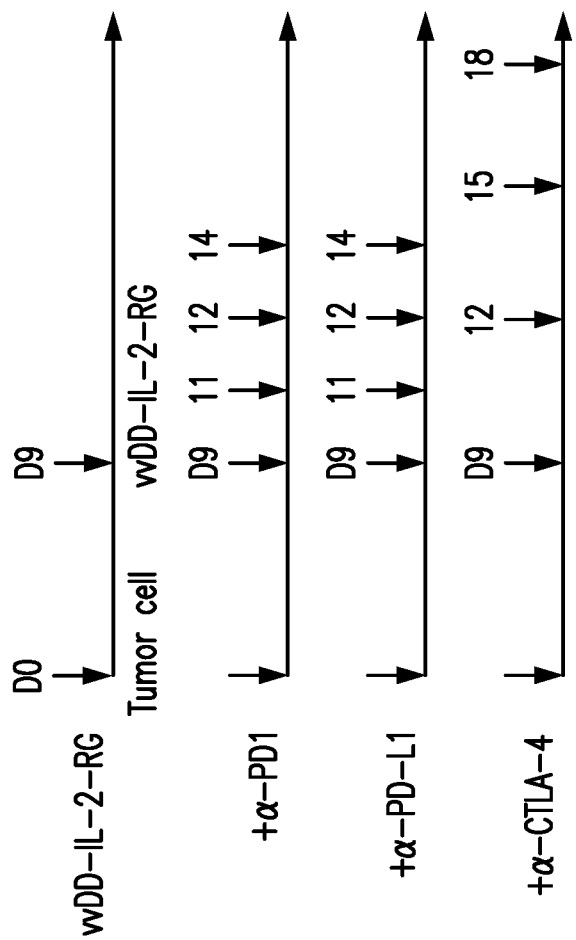

Combination of oncolytic vaccinia virus with an anti-PD-L1 antibody was previously suggested to work synergistically to enhance therapeutic efficacy on early-stage tumor model[26]. However, the combination of vvDD with the anti-PD-L1 antibody did not work in the late-stage tumor model (FIG. 21). Both vvDD-IL-2-FG and vvDD-IL-2-RG treatments elicited antitumor effects on the late-stage tumor model, and induced high PD-1, PD-L1 and CTLA-4 expression in tumors (FIG. 11C, FIGS. 22A-22C, and FIGS. 23A-23C). Therefore, combination of vvDD-IL-2-FG and vvDD-IL-2-RG and anti-PD-1/PD-L1 or anti-CTLA-4 antibodies was tested to investigate whether the combination could treat 9-day-tumour-bearing mice. The results showed that vvDD-IL-2-RG combined with an anti-PD-1/PD-L1 antibody, but not with an anti-CTLA-4 antibody, cured tumor-bearing mice (FIG. 22D). Without being bound to a particular theory, this could be attributed to the different mechanisms for anti-CTLA-4 and anti-PD-1/PD-L1 checkpoint blockade. Anti-CTLA-4 antibodies primarily affect CD4+ T cells at prime phase, while anti-PD-1/PD-L1 antibodies predominantly act on exhausted T cells within the tumor, which could important for overcoming the more immunosuppressive microenvironment in late-stage large solid tumors. The combination of VVDD-IL-2-FG with anti-PD-1/PD-L1 antibody did not improve the survival. Without being bound to a particular theory, this suggests that changes in immune status in tumor-bearing mice, especially in late-stage-tumor-bearing mice, was essential for the effectiveness of the monotherapy and the combination therapy. This could be evidenced by several recent reports showing the effectiveness of oncolytic viruses combined with immune checkpoint blockade in preclinical models and clinical trails (FIG. 22D and FIG. 24)[27-30].

In summary, the present Example demonstrated that vvDD-IL-2-RG treatment could effectively elicit antitumor immune status change in late-stage-tumor-bearing mice with significantly reduced systemic toxicity which was induced by IL-2 application, and finally led to a much better survival. The combination of vvDD-IL-2-RG with anti-PD-1 and PD-L1 antibodies can cure mice with late-stage-tumor. Thus, the present Example showed that vvDD-IL-2-RG treatment can be a new form of IL-2 immunotherapy that can be translatable to the clinic for cancers and immunosuppressive cancers.

8.4 References

1. Boyman, O. & Sprent, J. The role of interleukin-2 during homeostasis and activation of the immune system. Nat Rev Immunol 12, 180-190, doi:10.1038/nri3156 (2012).
2. Liao, W., Lin, J. X. & Leonard, W. J. Interleukin-2 at the crossroads of effector responses, tolerance, and immunotherapy. Immunity 38, 13-25, doi:10.1016/j.immuni.2013.01.004 (2013).
3. Lotze, M. T. et al. In vivo administration of purified human interleukin 2. II. Half life, immunologic effects, and expansion of peripheral lymphoid cells in vivo with recombinant IL 2. J Immunol 135, 2865-2875 (1985).
4. Yang, J. C. et al. Randomized study of high-dose and low-dose interleukin-2 in patients with metastatic renal cancer. J Clin Oncol 21, 3127-3132, doi:10.1200/JCO.2003.02.122 (2003).
5. Hu, P., Mizokami, M., Ruoff, G., Khawli, L. A. & Epstein, A. L. Generation of low-toxicity interleukin-2 fusion proteins devoid of vasopermeability activity. Blood 101, 4853-4861, doi:10.1182/blood-2002-10-3089 (2003).
6. Melder, R. J. et al. Pharmacokinetics and in vitro and in vivo anti-tumor response of an interleukin-2-human serum albumin fusion protein in mice. Cancer Immunol Immunother 54, 535-547, doi:10.1007/s00262-004-0624-7 (2005).
7. Puskas, J. et al. Development of an attenuated interleukin-2 fusion protein that can be activated by tumour-expressed proteases. Immunology 133, 206-220, doi:10.1111/j.1365-2567.2011.03428.x (2011).
8. Vazquez-Lombardi, R. et al. Potent antitumour activity of interleukin-2-Fc fusion proteins requires Fc-mediated depletion of regulatory T-cells. Nat Commun 8, 15373, doi:10.1038/ncomms15373 (2017).
9. Lazear, E. et al. Targeting of IL-2 to cytotoxic lymphocytes as an improved method of cytokine-driven immunotherapy. Oncoimmunology 6, e1265721, doi:10.1080/2162402X.2016.1265721 (2017).
10. Boyman, O., Surh, C. D. & Sprent, J. Potential use of IL-2/anti-IL-2 antibody immune complexes for the treatment of cancer and autoimmune disease. Expert OpinBiol Ther 6, 1323-1331, doi:10.1517/14712598.6.12.1323 (2006).
11. Letourneau, S. et al. IL-2/anti-IL-2 antibody complexes show strong biological activity by avoiding interaction with IL-2 receptor alpha subunit CD25. Proc Natl Acad Sci USA 107, 2171-2176, doi:10.1073/pnas.0909384107 (2010).
12. Levin, A. M. et al. Exploiting a natural conformational switch to engineer an interleukin-2 'superkine'. Nature 484, 529-533, doi:10.1038/nature10975 (2012).
13. Katre, N. V., Knauf, M. J. & Laird, W. J. Chemical modification of recombinant interleukin 2 by polyethylene glycol increases its potency in the murine Meth A sarcoma model. Proc Natl Acad Sci USA 84, 1487-1491 (1987).
14. Qin, H. et al. Gene therapy for head and neck cancer using vaccinia virus expressing IL-2 in a murine model, with evidence of immune suppression. Mol Ther 4, 551-558, doi:10.1006/mthe.2001.0493 (2001).
15. Zeh, H. J. et al. First-in-human study of Western Reserve Strain oncolytic vaccinia virus: safety, systemic spread ad anti-tumor activity. Mol Ther (In press) (2014).
16. Pan, W. Y. et al. Cancer immunotherapy using a membrane-bound interleukin-12 with B7-1 transmembrane and cytoplasmic domains. Mol Ther 20, 927-937, doi: 10.1038/mt.2012.10 (2012).
17. Ji, J. et al. Glycoinositol phospholipid-anchored interleukin 2 but not secreted interleukin 2 inhibits melanoma tumor growth in mice. Mol Cancer Ther 1, 1019-1024 (2002).
18. Paulick, M. G. & Bertozzi, C. R. The glycosylphosphatidylinositol anchor: a complex membrane-anchoring structure for proteins. Biochemistry 47, 6991-7000, doi: 10.1021/bi8006324 (2008).
19. Baluna, R. & Vitetta, E. S. Vascular leak syndrome: a side effect of immunotherapy. Immunopharmacology 37, 117-132 (1997).
20. Rosenstein, M., Ettinghausen, S. E. & Rosenberg, S. A. Extravasation of intravascular fluid mediated by the systemic administration of recombinant interleukin 2. J Immunol 137, 1735-1742 (1986).
21. Boyman, O., Kovar, M., Rubinstein, M. P., Surh, C. D. & Sprent, J. Selective stimulation of T cell subsets with antibody-cytokine immune complexes. Science 311, 1924-1927, doi:10.1126/science.1122927 (2006).
22. Dennis, K. L., Blatner, N. R., Gounari, F. & Khazaie, K. Current status of interleukin-10 and regulatory T-cells in cancer. Curr Opin Oncol 25, 637-645, doi:10.1097/CCO.0000000000000006 (2013).
23. Lentsch, A. B. et al. Interleukin-10 inhibits interleukin-2-induced tumor necrosis factor production but does not reduce toxicity in C3H/HeN mice. J Leukoc Biol 60, 51-57 (1996).
24. Kottke, T. et al. Subversion of NK-cell and TNFalpha Immune Surveillance Drives Tumor Recurrence. Cancer Immunol Res 5, 1029-1045, doi:10.1158/2326-6066.CIR-17-0175 (2017).
25. Alvarez-Breckenridge, C. A. et al. NK cells impede glioblastoma virotherapy through NKp30 and NKp46 natural cytotoxicity receptors. Nat Med 18, 1827-1834, doi:10.1038/nm.3013 (2012).
26. Liu, Z., Ravindranathan, R., Kalinski, P., Guo, Z. S. & Bartlett, D. L. Rational combination of oncolytic vaccinia virus and PD-L1 blockade works synergistically to enhance therapeutic efficacy. Nat Commun 8, 14754, doi:10.1038/ncomms14754 (2017).
27. Saha, D., Martuza, R. L. & Rabkin, S. D. Macrophage Polarization Contributes to Glioblastoma Eradication by Combination Immunovirotherapy and Immune Checkpoint Blockade. Cancer Cell 32, 253-267 e255, doi: 10.1016/j.ccell.2017.07.006 (2017).
28. Samson, A. et al. Intravenous delivery of oncolytic reovirus to brain tumor patients immunologically primes for subsequent checkpoint blockade. Sci Transl Med 10, doi:10.1126/scitranslmed.aam7577 (2018).
29. Bourgeois-Daigneault, M. C. et al. Neoadjuvant oncolytic virotherapy before surgery sensitizes triple-negative breast cancer to immune checkpoint therapy. Sci Transl Med 10, doi:10.1126/scitranslmed.aao1641 (2018).
30. Ribas, A. et al. Oncolytic Virotherapy Promotes Intratumoral T Cell Infiltration and Improves Anti-PD-1 Immunotherapy. Cell 170, 1109-1119 e1110, doi:10.1016/j.cell.2017.08.027 (2017).
31. Liu, Z. et al. CXCL11-Armed oncolytic poxvirus elicits potent antitumor immunity and shows enhanced therapeutic efficacy. OncoImmunology 5 (2016).
32. Rintoul, J. L. et al. A selectable and excisable marker system for the rapid creation of recombinant poxviruses. PloS one 6, e24643, doi:10.1371/journal.pone.0024643 (2011).

9. EXAMPLE 4: ADOPTIVE TRANSFER OF TUMOR-SPECIFIC TUMOR-INFILTRATED T CELLS LED TO SIGNIFICANT THERAPEUTIC EFFECTS IN SYNGENEIC C57BL/6 MICE BEARING PERITONEAL MC38 TUMOR

9.1 Introduction

Immunotherapy is rapidly evolving and fighting cancer by re-activating the patient immune system presents an attractive therapeutic strategy for gastrointestinal cancer besides standard treatments as surgery, chemotherapy and radiotherapy. Gastrointestinal cancer including colorectal, gastric, liver and biliopancreatic cancer belong to the ten most frequent malignancies worldwide (1). Immune infiltration impacts tumor progression and patient survival and that a strong lymphocyte infiltration has been reported to be associated with an antitumor response and improved clinical outcome in several GI adenocarcinomas (2-9). Different immunotherapeutic strategies as cancer vaccines, adoptive T cell transfer of autologous T cells or checkpoint blockade have been developed but are still not available for a wide range of GI tumors due to tumor heterogeneity and poor immune infiltration. Tumor cells develop immune escape mechanism modulating the immune system to avoid detection by effector cells. This includes cell surface expression of immune system checkpoint ligands such as programmed death ligand 1(PD-L1) (10,11), secretion of soluble immunosuppressive factors such as transforming growth factor beta (TGF-B), vascular endothelian growth factor (VEGF), interleukin-10 (Il-10), galectin-1, indoleamine 2,3-dehydrogenase (12-14), and down-regulation of major histocompatibility complex (MHC) class I expression; overexpression of receptors such as C—X—C chemokine receptor type 4 (CXCR4), basic fibroblast growth factor and epidermal growth factor (15,16).

The immunosuppressive tumor microenvironment presents optimal conditions for the recruitment of immunosuppressive macrophages, MDSCs and Tregs interfering with an efficient anti-tumor T cell response. Inhibitory checkpoint molecules as CTL-4, PD-1, TIM3, LAG3, upregulated in chronically stimulated T cells, promoting even further T cell anergy. A strategy to reverse the immunosuppressive tumor microenvironment (TME) and break immune tolerance is presented by oncolytic virotherapy. After selectively infecting and replicating in cancer cells and associated endothelial cells they kill these cells in cancerous tissue while leaving unaffected, healthy tissue unharmed (17,18). Immunogenic cell death (ICD) of stromal cells and cancer cells induced by OV exposes a natural repertoire of tumor-associated antigens (TAAs) in conjunction with danger signals (damage associated molecular pattern (DAMPs)) and OV-derived pathogen-associated molecular pattern (PAMP) molecules and inflammatory cytokines to elicit anti-tumor immunity (19-21). In a randomized phase II clinical trial in patients with advanced hepatocellular carcinoma, an oncolytic vaccinia virus armed with GM-CSF (Pexa-Vec) was associated with a 15% objective response rate (22). In a phase I clinical trial, an oncolytic vaccinia virus (Western Reserve Strain) vvDD was shown to be tumor selective and to promote anti-tumor response (23,24). To improve the immune response various oncolytic VV were engineered to express tumor antigens, T-cell co-stimulatory molecules and inflammatory cytokines (25). Their efficacy and safety have been demonstrated in preclinical studies (26-30). The present Example showed for the first time that oncolytic vaccinia virus-induced tumor infiltrating T cells (OV-induced T cells) (also referred to herein as "tumor-infiltrated T cells" or "TILs") can be used for ex vivo expansion and adoptive T cell transfer as new immunotherapeutic approach.

9.2 Methods

Mice and Cell Lines.

Female C57BL/6 mice were obtained from The Jackson Laboratory (Bar, Harbor, ME, USA) and housed in specific pathogen-free conditions in the University of Pittsburgh animal facility. All animal studies were approved by the Institutional Animal Care and Use Committee of the University. Murine colon cancer cell lines MC38 and B16 were obtained from ATCC. Mouse colon cancer MC38-luc was generated as described previously. All cell lines were grown in Dulbecco's modified Eagle's medium (DMEM) supplemented with 10% fetal bovine serum (FBS), 2 mM L-glutamine, and 1×penicillin/streptomycin solution (Invitrogen, Carlsbad, CA) in 37° C., 5% CO2 incubator.

Viruses.

Recombinant vaccinia virus (Western Reserve strain) vvDD, vvDD-CCL5 (31) and vvDD-CXC11 (32) were previously described. In the presently disclosed subject matter newly developed vvDD-IL-15 and vvDD-IL-2 are also provided. Virus has been purified in HeLa cells. Virus titer has been defined in CV-1 cells using plaque assay. For intratumoral virus application 1 e8 pfu per mouse have been used.

Rodent Tumor Models.

For subcutaneous (s.c.) tumor model, B6 mice were subcutaneously inoculated with 5×10⁵ MC38 cancer cells. vvDD-IL-2, vvDD-IL-15, vvDD-CXC11, vvDD-CCL5, vvDD or PBS was intratumorally injected at 1 e8 pfu/tumor when the s.c. tumor area reached 5×5 mm². In some experiments IL-2 was administered intratumoral with 1×10⁶ IU per tumor (Prometheus, San Diego, CA). The primary tumor size was measured using an electric caliper in two perpendicular diameters followed by every other day measurement. 10 days post virus treatment tumor tissue or spleen has been collected and proceed to single cell suspension for T cell separation and further analysis. For peritoneal (i.p.) tumor models, B6 mice were intraperitoneally inoculated with 5×10⁵ MC38-luc cells and randomized according to tumor size based on live animal IVIS imaging 7 days post tumor cell injection using a Xenogen IVIS 200 Optival In Vivo Imaging System (Caliber Life Sciences, Hoptikon, MA).

Generation of Tumor Reactive T-Cells for Adoptive Transfer.

B6 mice were s.c. inoculated with 5×10⁵ MC38 cancer cells. When the tumor area reached 5×5 mm² vvDD-IL-2 (1 e⁸ pfu per tumor) was intratumorally injected. 10 days later tumors have been collected and were incubated at 37° C. in digestion buffer (Miltenyi Biotec, San Diego, CA) before being mashed over a 100 μM tissue strainer. Lysis of red blood cell was performed using ACK Lysing buffer (Thermo Fisher Scientific, Waltham, MA). For Leukocyte separation Percoll (GE, Healthcare Life Science, Marlborough, MA) gradient centrifuge was used adapted from the protocol by Liu et al (Liu, Y., Chen, K., Wang, C., Gong, W., Yoshimura, T., Wang, J. M. and Liu, M. (2013). Isolation of Mouse Tumor-Infiltrating Leukocytes by Percoll Gradient Centrifugation. *Bio-protocol* 3(17): e892. DOI: 10.21769/BioProtoc.892). Leucocytes collected at the interface between 40% and 80% discontinuous Percoll gradient followed by magnetic separation (CD90.2 beads, Miltenyl Biotec, San Diego, CA). T cells have been cultured in 24-well plates in a concentration with 1×10⁶ per well in RPMI complete media with 30 IU/ml IL-2 (Miltenyi Biotec, San Diego, CA) and 5 ng/ml IL-7 (Biolegend, San Diego, CA) over 4 days. As control T cells, spleens from non-tumor bearing untreated mouse have been harvested and proceed to single cell suspension followed by magnetic separation (CD90.2 beads). The naïve T cells have been cultured under the same conditions as the virus induced T cells. Prior to adoptive T cell transfer, T cells have been analyzed for tumor specificity in a co-culture assay. T cells (2×10⁴ per well) were either left unstimulated (medium) or challenged with γ-irradiated MC38 tumor cells (2×10⁴ per well, 96-well plate) or irrelevant target cells as γ-irradiated B16 tumor cells (2×10⁴ per well) or naïve splenocytes (2×10⁴ per well) from non-tumor-bearing B6 mouse in duplicate for 24 h. The plate setup has been used for IFN-γ ELISPOT or Flow cytometry analysis as described above.

Adoptive Cell Transfer and Cytokine Administration.

B6 mice were intraperitoneally inoculated with 5×10⁵ MC38-luc cancer cells and divided into required groups according to tumor growth condition based on live animal IVIS imaging 7 days post tumor cell injection. Grouped mouse received 1×10⁶ vvDD-IL-2 induced T cells, naïve T cells or PBS. All treatment mouse received 5 Gy of sublethal irradiation to mimic lymphodepletion according to clinical protocols prior to cell transfer and exogenous cytokine support of IL-2 (100.000 IU/mouse i.p. for 3 days post transfer every 12 h) (Prometheus, San Diego, CA).

Flow Cytometry.

Post 24 h co-culture assay was performed as described above. T cells were stained using Zombi aqua (Biolegend, San Diego, CA) followed by staining with antibodies against mouse CD3, CD8, CD4, 4-1BB (Biolegend, San Diego, CA). Samples were collected by BD Bioscience LSRII Fortessa. Data were analyzed by BD FACS Diva software and FlowJo software (Tree Star Inc., Ashland, OR).

IFN-γ ELISPOT.

Collected tumor tissues were incubated at 37° C. in digestion buffer (Miltenyi Biotec, San Diego, CA) before being mashed over a 100 μM tissue strainer. Lysis of red blood cell was performed using ACK Lysing buffer (Thermo Fisher Scientific, Waltham, MA) and single cell suspension was proceeded by straining cell suspension over 40 μM filter. Isolation of CD8⁺ T cells was performed using negative a-mouse CD8 microbeads isolation protocol (Miltenl Biotec, San Diego, CA). 96 well Plates (MAHAS4510, Millipore, Burlington, MA) were coated with anti-mouse IFN-γ mAb 15 mg/ml (clone AN18, Mabtech Inc., Cincinnati, OH). T cells (2×10⁴ per well) were either left unstimulated (medium) or challenged with γ-irradiated MC38 tumor cells (2×10⁴ per well, 96-well plate) or irrelevant target cells as γ-irradiated B16 tumor cells (2×10⁴ per well) or naïve splenocytes (2×10⁴ per well) from non-tumor-bearing B6 mouse in duplicate for 24 h.

After appropriate washes, biotylated secondary antibody (clone R4-6A2-biotin, Mabtech, Inc) was added and incubated at room temperature for 2 h. Spot development followed using Vectastain Elite ABC and AEC Peroxidase substrate (SK-4200) kits (Vector Laboratories, Inc. Burlingame, CA). Number of IFN-γ spots were analyzed by ImmunoSpot™ (Cellular Technology, Ltd., Shaker Heights, OH).

Long-Term Survival of Mice.

The health and survival of treated mice was closely monitored. All mice bearing subcutaneous or peritoneal tumors were monitored via caliper measurements for changes in tumor size or abdominal girth. Mice died naturally due to the disease or sacrificed when their subcutaneous tumor size exceeded 20 mm in diameter or when abdominal girth exceeded 1.5×the original measurement.

Statistics.

Statistical analyses were performed using Student's t test (GraphPad Prism version 5). Animal survival is presented using Kaplan-Meier survival curves and was statistically analyzed using log rank test (GraphPad Prism version 5). Value of p<0.05 is considered to be statistically significant, and all p values were two sided. In the figures, the standard symbols were used: * p<0.05;  p<0.01; * p<0.001; and NS: not significant.

9.3 Results vvDD-IL-2 is a Potent Modulator of the TME Attracting High Numbers of Tumor Reactive T Cells.

To test if the different vaccinia virus constructs enhance the anti-tumor immune response and attract T cells into the TME, the T cell immune response in the TME of MC38 s.c. tumor bearing mouse was tested 10 days post intratumoral virus treatment with vvDD, vvDD-CXC11, vvDD-CCL5, vvDD-IL-15, vvDD-IL-2 or PBS. CD8+ T cells from virus-treated tumors were analyzed for IFN-γ response by ELISPOT. Compared to PBS control, all virus-treated tumors presented a significant increase in reactive CD8+ T cells when tested against γ-irradiated MC38 tumor cells. vvDD-IL-2 treated tumors presented the highest level of reactive CD8+ T cells compared to vvDD or vvDD-IL-15 treated tumors (FIG. 25A).

To investigate whether virus-induced CD8+ T cells are tumor specific, the IFN-γ response of CD8+ T cells from vvDD-IL-2, vvDD or PBS treated tumors was measured post co-culture with irrelevant target cells, e.g., γ-irradiated B16 tumor cells, naïve splenocytes from non-tumor-bearing B6 mouse and γ-irradiated MC38 tumor cells. Virus-treated tumors presented a significant increase in MC38-reactive CD8+ T cells compared to PBS control. vvDD-IL-2 induced CD8+ T cells exhibited highly specific reactivity against MC38 tumor cells compared to irrelevant target cells, e.g., B16 and naïve splenocytes. The vvDD induced T cells presented similar levels of MC38 reactivity compared to vvDD-IL-2, but exhibited higher background reactivity against the unspecific control cells as B16 and naïve splenocytes compared to vvDD-IL-2 (FIG. 25B). In summary, the vvDD-IL-2 induced T cells are highly MC38 specific.

Virally Expressed IL-2 Promotes a Strong Infiltration of Tumor Reactive CD8+ T Cells in the TME Compared to Single IL-2 Treatment.

To study the ability of the single IL-2 treatment to attract T cells into the TME in comparison to the IL-2-armed virus therapy, MC38 s.c. tumor bearing mouse were treated intratumorally with IL-2, vvDD-IL-2, vvDD or PBS. 10 days later, tumor infiltrating CD8+ T cells were analyzed for IFN-γ response by ELISPOT. The IFN-γ response of vvDD-IL-2 induced CD8+ T cells was prior compared to IL-2 treatment, control virus or PBS (FIG. 26).

vvDD-IL-2 Promotes T Cell Infiltration in the ME of MC38 Tumor Bearing Mouse.

To quantify the ability of vvDD-IL-2 to promote T cell infiltration in the TME, treated tumors were analyzed by immunofluorescence staining for total CD3+ infiltrating cells and CD3+CD8+ and CD3+CD4+ T cells (FIGS. 27 and 28). Both virus constructs promote significant increase of total CD3+ cells and CD8+ T cell infiltration in the TME compared to PBS control. Virus treatment presented an increase in CD4+ T cell infiltration compared to PBS samples. Similar results were observed in other experimental setups, when T cells were purified from tumor tissue and quantified per gram tumor (FIG. 28).

Vvdd-IL-2 Induced Tumor Infiltrating t Cells can be Expanded and Keep their Tumor specificity.

To test if vaccinia virus induced T cells can present a new strategy for adoptive T cell transfer, an ex vivo culture protocol of the tumor infiltrating T cells was established for T cell induction in MC38 s.c. tumor bearing mouse that were treated with vvDD-IL-2, vvDD or PBS (FIG. 29A). 10 days later tumors were harvested and infiltrating CD8+ T cells and CD4+ T cells from each tumor were cultured in the presence of IL-2 and IL-7 in RPMI complete media.

To test if the cultured T cells kept their tumor specificity, the T cells were tested for their tumor recognition using a co-culture assay, including relevant target cells (irradiated MC38 tumor cells) and irrelevant target cells as γ-irradiated B16 tumor cells or naïve splenocytes from non-tumor-bearing B6 mouse. After 24 h, the cells were analyzed for tumor specificity using IFN-γ ELISPOT or 4-1BB expression by flow cytometry. According to the IFN-γ ELISPOT, T cells from vvDD-IL-2, vvDD or PBS treated tumors presented tumor specific IFN-γ secretion compared to irrelevant target cells, e.g., B16 or naïve splenocytes (FIG. 29B).

To distinguish between CD8+ and CD4+ tumor specific T cell response flow cytometry results from each sample were summarized in FIG. 29C. vvDD-IL-2 induced T cells presented highly tumor specific CD8+ and CD4+ T cells with less unspecific reactivity against irrelevant target cells when compared to vvDD or PBS group (FIG. 29C). Representative flow cytometry plot of CD8$^+$4-1BB$^+$ and CD4$^+$4-1BB$^+$ T cells of one sample from each group is shown in FIG. 30.

vvDD-IL-2 Generated Tumor Reactive T Cells Present a New Strategy for Adoptive T Cell Transfer.

The newly developed approach of oncolytic virus induced T cells for ΔCT has been tested in MC38 i.p. tumor bearing mouse. Prior to T cell transfer, treated mouse received 5 Gy of sublethal irradiation to mimic lymphodepletion similar to clinical protocols. Grouped mouse were intraperitoneally injected with vvDD-IL-2-induced T cells, naïve T cells or PBS. All treated mouse received exogenous cytokine support of IL-2. The therapeutic response was monitored by live animal bioluminescence imaging to monitor the kinetics of tumor growth over time (FIG. 33C). Mouse that received vvDD-IL-2 induced T cells presented the strongest tumor regression compared to control mouse. In terms of animal survival, the virus-generated T cells led to the best overall survival compared to mice that received naïve T cells or only irradiation with IL-2 or PBS (FIG. 33C). Imaging Day 17 post ΔCT is shown in FIG. 34.

In summary, in the presently disclosed pre-clinical model the virus induced T cells present a therapeutic potential. To explore the tumor specificity of the transferred T cells, prior to ΔCT the established co-culture assay was performed (FIG. 31). Representative flow cytometry plot of CD8$^+$4-

1BB+ and CD4+4-1BB+ T cells of one sample from each group is shown in FIG. 32. T cells were analyzed for 4-1BB expression by flow cytometry and IFN-γ secretion by ELISPOT. Virus derived T cells presented tumor specific IFN-γ spots with nearly no reactivity against irrelevant target cells compared to naïve T cells (FIGS. 31B AND 31C). When the T cells from the same samples as used for ELISPOT were analyzed for 4-1BB expression, only the virus induced T cells presented significant tumor specific CD8+4-1BB+ and CD4+4-1BB expression when compared to control group.

9.4 Discussion

The present Example shows that cytokine-armed oncolytic vaccinia virus can promote intratumoral T cell infiltration and generates tumor specific T cells (OV-induced T cells) for adoptive T cell transfer.

A strong lymphocyte infiltration has been reported to be associated with an antitumor response and improved clinical outcome. But the majority of patients with gastrointestinal malignancies present pure immune cell infiltrated tumors with a highly immunosuppressive microenvironment. The application of oncolytic vaccinia virus with induction of immunogenic cell death offers an effective strategy to overcome less immunogenic tumors. Viral mediated cell death results in the release of potent danger signals and cross presentation of tumor-associated antigens, resulting in antitumor innate and adaptive immunity. In the present Example, the use of vaccinia virus induced tumor infiltrating T cells for ex vivo expansion and adoptive T cell transfer in a pre-clinical murine colon cancer model was demonstrated. Intratumoral application of cytokine-armed oncolytic vaccinia virus promotes T cell infiltration into the TME. The virus induced T cells were highly tumor specific and kept their therapeutic potential when expanded ex vivo and transferred into tumor bearing mouse. The present Example presents a strategy to promote intratumoral T cell infiltration and to generate tumor specific T cells in the tumor microenvironment for adoptive T cell transfer.

9.4. References

1. Siegel R, Ma J, Zou Z, Jemal A. Cancer statistics, 2014. CA Cancer J Clin 2014; 64(1):9-29 doi 10.3322/caac.21208.
2. Fridman W H, Pages F, Sautes-Fridman C, Galon J. The immune contexture in human tumours: impact on clinical outcome. Nat Rev Cancer 2012; 12(4):298-306 doi 10.1038/nrc3245.
3. Galon J, Costes A, Sanchez-Cabo F, Kirilovsky A, Mlecnik B, Lagorce-Pagès C, et al. Type, density, and location of immune cells within human colorectal tumors predict clinical outcome. Science 2006; 313(5795):1960-4 doi 10.1126/science.1129139.
4. Pagès F, Berger A, Camus M, Sanchez-Cabo F, Costes A, Molidor R, et al. Effector memory T cells, early metastasis, and survival in colorectal cancer. N Engl J Med 2005; 353(25):2654-66 doi 10.1056/NEJMoa051424.
5. Nakakubo Y, Miyamoto M, Cho Y, Hida Y, Oshikiri T, Suzuoki M, et al. Clinical significance of immune cell infiltration within gallbladder cancer. Br J Cancer 2003; 89(9):1736-42 doi 10.1038/sj.bjc.6601331.
6. Takagi S, Miyagawa S, Ichikawa E, Soeda J, Miwa S, Miyagawa Y, et al. Dendritic cells, T-cell infiltration, and Grp94 expression in cholangiocellular carcinoma. Hum Pathol 2004; 35(7):881-6.
7. Gao Q, Qiu S J, Fan J, Zhou J, Wang X Y, Xiao Y S, et al. Intratumoral balance of regulatory and cytotoxic T cells is associated with prognosis of hepatocellular carcinoma after resection. J Clin Oncol 2007; 25(18):2586-93 doi 10.1200/JCO.2006.09.4565.
8. Fukunaga A, Miyamoto M, Cho Y, Murakami S, Kawarada Y, Oshikiri T, et al. CD8+ tumor-infiltrating lymphocytes together with CD4+ tumor-infiltrating lymphocytes and dendritic cells improve the prognosis of patients with pancreatic adenocarcinoma. Pancreas 2004; 28(1):e26-31.
9. Lee H E, Chae S W, Lee Y J, Kim M A, Lee H S, Lee B L, et al. Prognostic implications of type and density of tumour-infiltrating lymphocytes in gastric cancer. Br J Cancer 2008; 99(10):1704-11 doi 10.1038/sj.bjc.6604738.
10. Nomi T, Sho M, Akahori T, Hamada K, Kubo A, Kanehiro H, et al. Clinical significance and therapeutic potential of the programmed death-1 ligand/programmed death-1 pathway in human pancreatic cancer. Clin Cancer Res 2007; 13(7):2151-7 doi 10.1158/1078-0432.CCR-06-2746.
11. Gao Q, Wang X Y, Qiu S J, Yamato I, Sho M, Nakajima Y, et al. Overexpression of PD-L1 significantly associates with tumor aggressiveness and postoperative recurrence in human hepatocellular carcinoma. Clin Cancer Res 2009; 15(3):971-9 doi 10.1158/1078-0432.CCR-08-1608.
12. Martinez-Bosch N, Fernandez-Barrena M G, Moreno M, Ortiz-Zapater E, Munné-Collado J, Iglesias M, et al. Galectin-1 drives pancreatic carcinogenesis through stroma remodeling and Hedgehog signaling activation. Cancer Res 2014; 74(13):3512-24 doi 10.1158/0008-5472.CAN-13-3013.
13. Kobayashi N, Kubota K, Kato S, Watanabe S, Shimamura T, Kirikoshi H, et al. FOXP3+ regulatory T cells and tumoral indoleamine 2,3-dioxygenase expression predicts the carcinogenesis of intraductal papillary mucinous neoplasms of the pancreas. Pancreatology 2010; 10(5):631-40 doi 10.1159/000308966.
14. Brandacher G, Perathoner A, Ladurner R, Schneeberger S, Obrist P, Winkler C, et al. Prognostic value of indoleamine 2,3-dioxygenase expression in colorectal cancer: effect on tumor-infiltrating T cells. Clin Cancer Res 2006; 12(4):1144-51 doi 10.1158/1078-0432.CCR-05-1966.
15. Feig C, Jones J O, Kraman M, Wells R J, Deonarine A, Chan D S, et al. Targeting CXCL12 from FAP-expressing carcinoma-associated fibroblasts synergizes with anti-PD-L1 immunotherapy in pancreatic cancer. Proc Natl Acad Sci USA 2013; 110(50):20212-7 doi 10.1073/pnas.1320318110.
16. Chatterjee S, Behnam Azad B, Nimmagadda S. The intricate role of CXCR4 in cancer. Adv Cancer Res 2014; 124:31-82 doi 10.1016/B978-0-12-411638-2.00002-1.
17. Russell S J, Peng K W, Bell J C. Oncolytic virotherapy. Nat Biotechnol 2012; 30(7):658-70 doi 10.1038/nbt.2287.
18. Guo Z S, Thorne S H, Bartlett D L. Oncolytic virotherapy: molecular targets in tumor-selective replication and carrier cell-mediated delivery of oncolytic viruses. Biochim Biophys Acta 2008; 1785(2):217-31 doi 10.1016/j.bbcan.2008.02.001.
19. Tang D, Kang R, Coyne C B, Zeh H J, Lotze M T. PAMPs and DAMPs: signal 0s that spur autophagy and immunity. Immunol Rev 2012; 249(1):158-75 doi 10.1111/j.1600-065X.2012.01146.x.

20. Medzhitov R, Janeway C A. Decoding the patterns of self and nonself by the innate immune system. Science 2002; 296(5566):298-300 doi 10.1126/science.1068883.
21. Matzinger P. The danger model: a renewed sense of self. Science 2002; 296(5566):301-5 doi 10.1126/science.1071059.
22. Heo J, Reid T, Ruo L, Breitbach C J, Rose S, Bloomston M, et al. Randomized dose-finding clinical trial of oncolytic immunotherapeutic vaccinia JX-594 in liver cancer. Nat Med 2013; 19(3):329-36 doi 10.1038/nm.3089.
23. Zeh H J, Downs-Canner S, McCart J A, Guo Z S, Rao U N, Ramalingam L, et al. First-in-man study of western reserve strain oncolytic vaccinia virus: safety, systemic spread, and antitumor activity. Mol Ther 2015; 23(1):202-14 doi 10.1038/mt.2014.194.
24. Downs-Canner S, Guo Z S, Ravindranathan R, Breitbach C J, O'Malley M E, Jones H L, et al. Phase 1 Study of Intravenous Oncolytic Poxvirus (vvDD) in Patients With Advanced Solid Cancers. Mol Ther 2016; 24(8):1492-501 doi 10.1038/mt.2016.101.
25. Kaufman H L, Kohlhapp F J, Zloza A. Oncolytic viruses: a new class of immunotherapy drugs. Nat Rev Drug Discov 2015; 14(9):642-62 doi 10.1038/nrd4663.
26. McCart J A, Ward J M, Lee J, Hu Y, Alexander H R, Libutti S K, et al. Systemic cancer therapy with a tumor-selective vaccinia virus mutant lacking thymidine kinase and vaccinia growth factor genes. Cancer Res 2001; 61(24):8751-7.
27. Guo Z S, Naik A, O'Malley M E, Popovic P, Demarco R, Hu Y, et al. The enhanced tumor selectivity of an oncolytic vaccinia lacking the host range and antiapoptosis genes SPI-1 and SPI-2. Cancer Res 2005; 65(21): 9991-8 doi 10.1158/0008-5472.CAN-05-1630.
28. Zhang Q, Yu Y A, Wang E, Chen N, Danner R L, Munson P J, et al. Eradication of solid human breast tumors in nude mice with an intravenously injected light-emitting oncolytic vaccinia virus. Cancer Res 2007; 67(20):10038-46 doi 10.1158/0008-5472.CAN-07-0146.
29. Kirn D H, Wang Y, Liang W, Contag C H, Thorne S H. Enhancing poxvirus oncolytic effects through increased spread and immune evasion. Cancer Res 2008; 68(7): 2071-5 doi 10.1158/0008-5472.CAN-07-6515.
30. Sathaiah M, Thirunavukkarasu P, O'Malley M E, Kavanagh M A, Ravindranathan R, Austin F, et al. Oncolytic poxvirus armed with Fas ligand leads to induction of cellular Fas receptor and selective viral replication in FasR-negative cancer. Cancer Gene Ther 2012; 19(3): 192-201 doi 10.1038/cgt.2011.77.
31. Li J, O'Malley M, Urban J, Sampath P, Guo Z S, Kalinski P, Thorne S H, Bartlett D L. Chemokine expression from oncolytic vaccinia virus enhances vaccine therapies of cancer. Mol Ther. 2011 April; 19(4):650-7. doi: 10.1038/mt.2010.312.
32. Liu Z, Ravindranathan R, Li J, Kalinski P, Guo Z S, Bartlett D L. CXCL11-Armed oncolytic poxvirus elicits potent antitumor immunity and shows enhanced therapeutic efficacy. Oncoimmunology. 2015 Oct. 29; 5(3): e1091554.

10. REFERENCES

1. U.S. Pat. No. 6,277,368.
2. U.S. Pat. No. 7,208,313.
3. U.S. Pat. No. 7,264,820.
4. U.S. Pat. No. 8,506,947
5. United States Patent Application Publication No. 2003/0031681.
6. United States Patent Application Publication No. 2003/0105054
7. United States Patent Application Publication No. 2007/0154458
8. International Patent Application Publication no. WO 1999006544.
9. International Patent Application Publication No. WO 2003017944.
10. Bartlett D L et al., 2013, Oncolytic viruses as therapeutic cancer vaccines, Molecular Cancer 12:103-120.
11. Chiocca E A and Rabkin S D, 2014, Cancer Immunol Res; 2(4); 295-300.
12. Ferguson et al., "Chapter 11: Glycosylphosphatidyl Anchors" in Glycobiology, 2nd Edition, Varki et al., editors, Cold Spring Harbor Press, 2009.
13. Galian C et al., 2012, J Biol. Chem. 287 (2)):16399-16409.
14. Kaufman H L et al., 2015, Nature Reviews Drug Discovery 14:642-662.
15. Mayor S and Riezman H, 2004, Nature Reviews Molecular Cell Biology 5, 110-120.
16. McCart et al., 2001, Cancer Research 61:8751-8757.
17. Simmons D and Seed B, 1988, Nature 333:568-570.
18. Thorne S et al., 2007, J. Clin. Invest. 117:3350-3358.
19. Guo Z S, Liu Z, Bartlett D L. Oncolytic immunotherapy: dying the right way is a key to eliciting potent antitumor immunity. Front Oncol (2014) 4:74. DOI: 10.3389/fonc.2014.00074.
20. Guo Z S, Liu Z, Kowalsky S, Feist M, Kalinski P, Lu B, et al. Oncolytic immunotherapy: conceptual evolution, current strategies, and future perspectives. Front Immunol (2017) 8:555. DOI: 10.3389/fimmu.2017.00555.
21. Andtbacka R H, Kaufman H L, Collichio F, Amatruda T, Senzer N, Chesney J, et al. Talimogene laherparepvec improves durable response rate in patients with advanced melanoma. J Clin Oncol (2015) 33:2780-8. DOI: 10.1200/JCO.2014.58.3377.
22. Zou W. Immunosuppressive networks in the tumour environment and their therapeutic relevance. Nat Rev Cancer (2005) 5:263-74. DOI: nrc1586 [pii] 10.1038/nrc1586.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various references, patents and patent applications are cited herein, the contents of which are hereby incorporated by reference herein in their entireties.

We claim:

1. An oncolytic virus comprising, in its genome, a nucleic acid encoding a membrane-associated fusion protein comprising an immunomodulator molecule directly linked to an anchoring peptide via a rigid linker, wherein:
   the immunomodulator molecule comprises SEQ ID NO: 13 or SEQ ID NO: 13 with one or two amino acid variations;
   the oncolytic virus is a vaccinia virus;
   the nucleic acid is operably linked to an oncolytic virus promoter;
   the rigid linker is a peptide linker between 1 and 25 amino acids in length; and
   the anchoring peptide comprises a GPI-anchor acceptor peptide.

2. The oncolytic virus of claim 1, wherein said rigid linker comprises SEQ ID NO:36.

3. The oncolytic virus of claim 1, wherein the oncolytic virus is a recombinant vaccinia virus with an inactivating mutation of its thymidine kinase gene, vaccinia growth factor gene, or both.

4. The oncolytic virus of claim 1, wherein said GPI-anchor acceptor peptide comprises SEQ ID NO: 11.

* * * * *

SEQUENCE LISTING

<160> NUMBER OF SEQ ID NOS: 36

<210> SEQ ID NO 1
<211> LENGTH: 34
<212> TYPE: PRT
<213> ORGANISM: Homo sapiens

<400> SEQUENCE: 1

Ser Ser Phe Ser Pro Pro Gly Tyr Gln Val Ser Phe Cys Leu Val Met
1               5                   10                  15

Val Leu Leu Phe Ala Val Asp Thr Gly Leu Tyr Phe Ser Val Lys Thr
            20                  25                  30

Asn Ile

<210> SEQ ID NO 2
<211> LENGTH: 22
<212> TYPE: PRT
<213> ORGANISM: Homo sapiens

<400> SEQUENCE: 2

Gly Gly Ala Leu Gln Ser Thr Ala Ser Leu Phe Val Val Ser Leu Ser
1               5                   10                  15

Leu Leu His Leu Tyr Ser
            20

<210> SEQ ID NO 3
<211> LENGTH: 24
<212> TYPE: PRT
<213> ORGANISM: Homo sapiens

<400> SEQUENCE: 3

Asn Asn Ser Cys Ser Ser Pro Gly Gly Cys Arg Leu Phe Leu Ser Thr
1               5                   10                  15

Ile Pro Val Leu Trp Thr Leu Leu
            20

<210> SEQ ID NO 4
<211> LENGTH: 28
<212> TYPE: PRT
<213> ORGANISM: Homo sapiens

<400> SEQUENCE: 4

Asp Ala Ala His Pro Gly Arg Ser Val Val Pro Ala Leu Leu Pro Leu
1               5                   10                  15

Leu Ala Gly Thr Leu Leu Leu Glu Thr Ala Thr
            20                  25

<210> SEQ ID NO 5
<211> LENGTH: 23
<212> TYPE: PRT
<213> ORGANISM: Homo sapiens

<400> SEQUENCE: 5

Ser Ala Ala Pro Arg Leu Phe Pro Leu Ala Trp Thr Val Leu Leu Leu
1               5                   10                  15

Pro Leu Leu Leu Leu Gln Thr
            20

<210> SEQ ID NO 6
<211> LENGTH: 24
<212> TYPE: PRT
<213> ORGANISM: Homo sapiens

```
<400> SEQUENCE: 6

Asn Gly Ser Ile Ser Leu Ala Val Pro Leu Trp Leu Leu Ala Ala Ser
1               5                   10                  15

Leu Leu Cys Leu Leu Ser Cys Lys
            20

<210> SEQ ID NO 7
<211> LENGTH: 26
<212> TYPE: PRT
<213> ORGANISM: Homo sapiens

<400> SEQUENCE: 7

Ser Gly Ala Pro Thr Leu Ser Pro Ser Leu Leu Gly Leu Leu Leu Pro
1               5                   10                  15

Ala Phe Gly Ile Leu Val Tyr Leu Glu Phe
            20                  25

<210> SEQ ID NO 8
<211> LENGTH: 24
<212> TYPE: PRT
<213> ORGANISM: Rattus sp.

<400> SEQUENCE: 8

Asn Gly Thr Ser Arg Arg Ala Gly Cys Ile Trp Leu Leu Pro Leu Leu
1               5                   10                  15

Val Leu His Leu Leu Leu Lys Phe
            20

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Ser Thr Gly Ser Gly Ser Ser Gly Ser Ala Ala Ala Ala Val Ala
1               5                   10                  15

Ala Ala Ala Val Ala Ala Ala Ala Val Ala Ala Ala Ala
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Ser Thr Gly Ser Gly Ser Ser Gly Ser Ala Ala Ala Ala Val Val
1               5                   10                  15

Phe Val Phe Val Phe Val Phe Val Val Ala Ala Ala Ala
            20                  25

<210> SEQ ID NO 11
<211> LENGTH: 38
<212> TYPE: PRT
<213> ORGANISM: Homo sapiens

<400> SEQUENCE: 11
```

Val Ser Thr Ile Ser Ser Phe Ser Pro Pro Gly Tyr Gln Val Ser Phe
1               5                   10                  15

Cys Leu Val Met Val Leu Leu Phe Ala Val Asp Thr Gly Leu Tyr Phe
                20                  25                  30

Ser Val Lys Thr Asn Ile
            35

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Ser Gly Gly Gly Gly Ser
1               5                   10                  15

<210> SEQ ID NO 13
<211> LENGTH: 133
<212> TYPE: PRT
<213> ORGANISM: Homo sapiens

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
    115                 120                 125

Ile Ser Thr Leu Thr
        130

<210> SEQ ID NO 14
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys

```
            50                 55                  60
Pro Leu Glu Glu Val Leu Asn Leu Ala Gln Ser Lys Asn Phe His Leu
 65              70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Pro Ala Gly Gly Gly Ser Gly Gly Gly
130                 135                 140

Gly Ser Gly Gly Gly Ser Val Ser Thr Ile Ser Ser Phe Ser Pro
145                 150                 155                 160

Pro Gly Tyr Gln Val Ser Phe Cys Leu Val Met Val Leu Leu Phe Ala
                165                 170                 175

Val Asp Thr Gly Leu Tyr Phe Ser Val Lys Thr Asn Ile
                180                 185

<210> SEQ ID NO 15
<211> LENGTH: 233
<212> TYPE: PRT
<213> ORGANISM: Homo sapiens

<400> SEQUENCE: 15

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
                 20                  25                  30

Leu Ser Leu Phe Ser Phe Leu Ile Val Ala Gly Ala Thr Thr Leu Phe
             35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230
```

```
<210> SEQ ID NO 16
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Pro Ala Gly Gly Gly Ser Gly Gly Gly Ser Gly Gly
1               5                   10                  15

Gly Ser Val Ser Thr Ile Ser Ser Phe Ser Pro Pro Gly Tyr Gln Val
            20                  25                  30

Ser Phe Cys Leu Val Met Val Leu Phe Ala Val Asp Thr Gly Leu
        35                  40                  45

Tyr Phe Ser Val Lys Thr Asn Ile
    50                  55

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Ser Thr Gly Ser Gly Ser Ser Gly Ser
1               5                   10

<210> SEQ ID NO 18
<211> LENGTH: 189
<212> TYPE: PRT
<213> ORGANISM: Homo sapiens

<400> SEQUENCE: 18

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 19
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcgggtcgac atatggcgcc atgcattata aggcgcgccc gcccctctcc ctccc          55

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggccgttaac ttaagagctc atttaaatcc tgcagggccg gccattatca tcgtg          55

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggccggccgg ccggtggcgg tgggagcggt ggtgggggtt ccggaggcgg aggg           54

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggttccggag gcggagggtc ggtgtcaacc atctcatcat tctc                      44

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcgcgttaac tcaaatgttt gtcttcacag ag                                   32

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggccggccgg ccgctgaagc tgccgcaaaa gaggccgctg cgaaggaggc cgcggctaag     60

```
<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaggccgcgg ctaaggaggc ggcagctaaa gctgcagccg tgtcaaccat ctcatcattc    60

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgcgttaac tcaaatgttt gtcttcacag ag                                  32

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcggtcgac atgtacagca tgcagctcg                                      29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgcggcgcg ccttattgag ggcttgttga g                                   31

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggcggtcgac atgtacagca tgcagctcg                                      29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgcggccgg cccttgaggg cttgttgag                                      29
```

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggcggtcgac atgtacagca tgcagctcg                                29

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgcggccgg cccttgaggg cttgttgag                                29

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggccggccgg ccggtggcgg tgggagcggt ggtgggggtt ccggaggcgg aggg    54

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccggaggcgg tgggtcgcac tgggtgcttc tgggatc                       37

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgcgttaact accccaagaa gaggaggacc gtggacacta caatgaggaa caacaggatg    60

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 36

Ala Glu Ala Ala Ala Lys Glu Ala Ala Lys Glu Ala Ala Lys
1               5                   10                  15

Glu Ala Ala Ala Lys Ala Ala Ala
            20
```